US007724257B2

(12) United States Patent
Smith et al.

(10) Patent No.: US 7,724,257 B2
(45) Date of Patent: *May 25, 2010

(54) SYSTEMS, METHODS AND COMPUTER PROGRAM PRODUCTS FOR DETERMINING PARAMETERS FOR CHEMICAL SYNTHESIS

(75) Inventors: Robin Young Smith, San Jose, CA (US); William Brian Ballard, Durham, NC (US); David Albert Coleman, San Francisco, CA (US)

(73) Assignee: Symyx Solutions, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/780,299

(22) Filed: Jul. 19, 2007

(65) Prior Publication Data

US 2008/0015837 A1 Jan. 17, 2008

Related U.S. Application Data

(63) Continuation of application No. 10/395,713, filed on Mar. 24, 2003, now Pat. No. 7,250,950, which is a continuation-in-part of application No. 10/059,818, filed on Jan. 29, 2002, now abandoned, which is a continuation-in-part of application No. 09/772,229, filed on Jan. 29, 2001, now abandoned.

(60) Provisional application No. 60/367,993, filed on Mar. 25, 2002.

(51) Int. Cl.
*G06T 11/20* (2006.01)
(52) U.S. Cl. .................. 345/440; 700/266; 700/268
(58) Field of Classification Search .................. 345/440; 700/266, 268
See application file for complete search history.

(56) References Cited

U.S. PATENT DOCUMENTS 4,982,338 A * 1/1991 Fujita ........................... 703/12
5,047,929 A * 9/1991 Fujita ........................... 703/6

(Continued)

FOREIGN PATENT DOCUMENTS

WO WO 00/23921 4/2000

OTHER PUBLICATIONS

Backofen, R., et al., "Application of constraint programming techniques for structure prediction of lattice proteins with extended alphabets", (Feb. 1999), 17 pages.

(Continued)

*Primary Examiner*—M Good Johnson
(74) *Attorney, Agent, or Firm*—McDermott Will & Emery LLP

(57) ABSTRACT

The database is populated with target chemicals, corresponding listings of reagent chemicals, corresponding listings of equipment and corresponding listings of procedures. The database is then searched in response to user identification of a target chemical. In response, a listing is displayed of reagent chemicals that are used to synthesize the target chemical, equipment that is used to synthesize the target chemical, and a procedure that is used to synthesize the target chemical by reacting the reagent chemicals in the equipment according to the procedure. An icon-based reaction editor and/or context-sensitive Boolean query option generators may be provided. A reaction template may be used to perform predictive chemistry. A reaction relay may be used to graphically display related chemicals and procedures using a hub and spoke arrangement.

33 Claims, 46 Drawing Sheets

U.S. PATENT DOCUMENTS

| | | | |
|---|---|---|---|
| 5,056,035 A * | 10/1991 | Fujita | 703/12 |
| 5,574,656 A * | 11/1996 | Agrafiotis et al. | 506/5 |
| 5,708,806 A | 1/1998 | DeRose et al. | |
| 5,848,415 A | 12/1998 | Guck | |
| 5,962,013 A | 10/1999 | Wong et al. | |
| 5,980,096 A * | 11/1999 | Thalhammer-Reyero | 707/100 |
| 6,030,917 A | 2/2000 | Weinberg et al. | |
| 6,410,331 B1 | 6/2002 | Schultz et al. | |
| 6,415,276 B1 | 7/2002 | Heger et al. | |
| 6,618,852 B1 | 9/2003 | Van Eikeren et al. | |
| 6,658,429 B2 * | 12/2003 | Dorsett, Jr. | 707/104.1 |
| 6,738,529 B1 | 5/2004 | Crevier et al. | |
| 6,947,953 B2 | 9/2005 | Herzenberg et al. | |
| 6,968,536 B2 | 11/2005 | Jazdzewski | |
| 6,983,227 B1 * | 1/2006 | Thalhammer-Reyero | 703/2 |
| 7,188,055 B2 * | 3/2007 | Agrafiotis et al. | 703/2 |
| 7,199,809 B1 * | 4/2007 | Lacy et al. | 715/700 |
| 7,308,363 B2 * | 12/2007 | Eker et al. | 702/19 |
| 7,478,337 B2 | 1/2009 | Kodosky et al. | |
| 2001/0047398 A1 * | 11/2001 | Rubenstein | 709/218 |
| 2002/0049548 A1 * | 4/2002 | Bunin | 702/32 |
| 2004/0044990 A1 | 3/2004 | Schloegel et al. | |
| 2004/0221260 A1 | 11/2004 | Martin et al. | |
| 2005/0130229 A1 | 6/2005 | Dorsett, Jr. | |
| 2005/0267721 A1 * | 12/2005 | Thalhammer-reyero | 703/11 |
| 2005/0273305 A1 * | 12/2005 | Thalhammer-Reyero | 703/11 |
| 2006/0064674 A1 | 3/2006 | Olson, Jr. et al. | |
| 2006/0168515 A1 | 7/2006 | Dorsett, Jr. | |
| 2006/0277201 A1 | 12/2006 | Dorsett, Jr. | |
| 2007/0050092 A1 | 3/2007 | Kenyon et al. | |
| 2007/0143240 A1 | 6/2007 | Goldwasser et al. | |
| 2007/0185657 A1 | 8/2007 | Lacy et al. | |
| 2007/0203951 A1 | 8/2007 | Dorsett, Jr. | |
| 2007/0214101 A1 | 9/2007 | Wang et al. | |

OTHER PUBLICATIONS

Barr, R.S., et al., "Designing and reporting on computational experiments with heuristic methods", Journal of Heuristics Kluwer Academic Publishers Netherlands, vol. 1, No. 1 (Sep. 1995), pp. 9-32.

Raynor, W., The International Dictionary of Artificial Intelligence, (1999), p. 63 and cover.

Shaheen, M., et al., "Remote Laboratory Experimentation", Proceedings of the American Control Conference, Philadelphia, PA, (Jun. 1998), pp. 1326-1329.

U.S. Appl. No. 12/482,353, filed Jun. 10, 2009, Barstow.

U.S. Appl. No. 11/325,267, filed Jan. 3, 2006, Falcioni et al.

U.S. Appl. No. 09/174,856, filed Oct. 19, 1998, Lacy et al.

Thayer, A., "Combinatorial Chemistry Becoming Core Technology at Drug Discovery Companies", Chem Eng. News, (Feb. 12, 1996), pp. 57-64.

Umetrics AB, Modde 4-0 Users Guide, Copyright 1992-1997, pp. 1-1 to 14-2 (229 pages) "Graphical Software for Design of Experiments".

Zou, J. et al., "Statistical Theory of Combinatorial Libraries of Folding Proteins: Energetic Discrimination of a Target Structure", J Mol Biol, vol. 296 (2009), pp. 281-294.

* cited by examiner

| | Synthematix Protocol Manager ver. 0.90q | | _ □ X |
|---|---|---|---|
| File Apparatus Atmosphere Operations | | | |

Name | CAS | Formula | Weight
6-(alkamino)-5-amino-4-chloropyrimidine | R00-02-3 | C7H9N4Cl | 184.83

Reagents benzene  Lookup

Starting Flask
Round bottom 3-neck flask ▷
Equipped with:
▷
▷
▷
▷
▷
▷
▷
▷
▷
▷

| | CAS | Name | Weight | Amount(g) |
|---|---|---|---|---|
| 1. | R00-02-4 | 5-amino-4,6-dichloropyrimidine | 163.99 | 50 |
| 2. | 107-11-9 | 2-Propen-1-amine | 57.09 | 100 |
| 3. | 64-17-5 | Ethanol | 46.07 | 100 |
| 4. | 71-43-2 | Benzene | 78.11 | 3146.4 |
| 5. | | | | |
| 6. | | | | |
| 7. | | | | |
| 8. | | | | |
| 9. | | | | |
| 10. | | | | |

Procedure
Previous Next

Step 1

Into a round bottom 3-neck flask was added
<GN0> grams (<MN0> mol) of 5-amino-4,6-
dichloropyrimidine Info    New
Properties    Save
Reference
Extra Equip    Update

FIG. 11

Synthematix Protocol Manager ver. 0.90q  
File  Apparatus  Atmosphere  Operations Name: 6-(allylamino)-5-amino-4-chloropyrimidine   CAS: R00-02-3   Formula: C7H9N4Cl   Weight: 184.83

Reagents: benzene   [Lookup]

☐ Enter procedure by hand

| # | CAS | Name | Weight | Amount(g) |
|---|---|---|---|---|
| 1. | R00-02-4 | 5-amino-4,6-dichloropyrimidine | 163.99 | 50 |
| 2. | 107-11-9 | 2-Propen-1-amine | 57.09 | 100 |
| 3. | 64-17-5 | Ethanol | 46.07 | 100 |
| 4. | 71-43-2 | Benzene | 78.11 | 3146.4 |
| 5. | | | | |
| 6. | | | | |
| 7. | | | | |
| 8. | | | | |
| 9. | | | | |
| 10. | | | | |

Action: [▷]  
- The aqueous phase  
- The organic phase  
- The reaction mixture  
- The solids  
- The solvent  
- To the flask  
- To the stirring mixture Qualifier:  
Action:  
Reagent:  
Time: [▷]

[Reset]   [Add To Procedure]

Procedure

Step 7

[Previous] [Next]

[Info]       [New]
[Properties] [Save]
[Reference]
[Extra Equip] [Update]

FIG. 12

| Synthematix Protocol Manager ver. 0.90q | | | | | — □ X |
|---|---|---|---|---|---|
| File Apparatus Atmosphere Operations | | | | | |

Name | | CAS | Formula | | Weight
---|---|---|---|---|---
6-(alkamino)-5-amino-4-chloropyrimidine | | R00-02-3 | C7H9N4Cl | | 184.83

Reagents | benzene | Lookup |

☐ Enter procedure by hand

| | CAS | Name | Weight Amount(g) | |
|---|---|---|---|---|
| 1. | R00-02-4 | 5-amino-4,6-dichloropyrimidine | 163.99 | 50 |
| 2. | 107-11-9 | 2-Propen-1-amine | 57.09 | 100 |
| 3. | 64-17-5 | Ethanol | 46.07 | 100 |
| 4. | 71-43-2 | Benzene | 78.11 | 3146.4 |
| 5. | | | | |
| 6. | | | | |
| 7. | | | | |
| 8. | | | | |
| 9. | | | | |
| 10. | | | | |

Action: | To the flask ▷
Qualifier: | was ▷
Action: | added ▷
Reagent: | Reagent 2 ▷
Time: | ▷
Reset | Add To Procedure Procedure Previous | Next Step 2

To the flask was added <GN1> grams (<MN1> mol)
of 2-Propen-1-amine and <GN2> grams (<MN2>mol)
of Ethanol New | Info
Save | Properties
 | Reference
Update | Extra Equip

FIG. 13

| Synthematix Protocol Manager ver. 0.90q | | | | |
|---|---|---|---|---|
| File Apparatus Atmosphere Operations | | | | |

Name: 6-(aIIyIamino)-5-amino-4-chloropyrimidine  CAS: R00-02-3  Formula: C7H9N4Cl  Weight: 184.83

Reagents: benzene  [Lookup]

| | CAS | Name | Weight | Amount(g) |
|---|---|---|---|---|
| 1. | R00-02-4 | 5-amino-4,6-dichloropyrimidine | 163.99 | 50 |
| 2. | 107-11-9 | 2-Propen-1-amine | 57.09 | 100 |
| 3. | 64-17-5 | Ethanol | 46.07 | 100 |
| 4. | 71-43-2 | Benzene | 78.11 | 3146.4 |
| 5. | | | | |
| 6. | | | | |
| 7. | | | | |
| 8. | | | | |
| 9. | | | | |
| 10. | | | | |

☐ Enter procedure by hand

Action: ▷
Qualifier: ▷
Action: ▷
Reagent: ▷
Time: ▷

[Reset]   [Add To Procedure]

[Info]   [New]
[Properties]   [Save]
[Reference]
[Extra Equip]   [Update]

Procedure
[Previous] [Next]   Step 2

To the flask was added <GN1> grams (<MN1> mol) of 2-Propen-1-amine and <GN2> grams (<MN2>mol) of Ethanol

```
Synthematix: Search Results - Netscape                                    _□X
File Edit View Go Communicator Help
```

SYNTHEMATIX
Powered by Scientists™

Chemical Procedures

Search for:
Chemical procedures
Access our database of over
10,000 chemical procedures

Equipment
Shop for lab equipment

Raw Materials

Glassware
Stock and custom glassware

Publications
Access scientific papers
published online with
Synthematix

Advanced
Enter an advanced site-wide
search query

Synthematix: Search Results

Number of matches: 7 alpha-bromo-p-toluene boronic acid

N-butyl-2-bromopropionate (6-Bromo-2,2-diphenylbenzo[1,3]dioxol-5-yl)methanol (6-Bromo-2,2-dimethylbenzo[1,3]dioxol-5-yl)methanol 6-bromo-2,2-diphenylbenzo[1,3]dioxole-5-carbaldehyde 6-bromo-3,4-[(diphenylmethylene)dioxy]benzaldehyde ethanediyl acetal 1Benzhydryl-3-bromoazetidine

---

Synthematix: Powered by Scientists home | about | chemical procedures | equipment | glassware | raw materials privacy policy | submit publication | submit news | advertising Copyright 2000 Synthematix. All trademarks and copyright on
this page are owned by their respective companies.
Comments are owned by the Poster.

FIG. 20B

| | | | 0.0000 | |
|---|---|---|---|---|
| Dowex 50W4-200 | 3.68 | 1 | 0.0000 | |
| Water | 18 | 1 | 0.0000 | 0.0000 |

Equipment needed

2030

| Qty | Equipment |
|---|---|
| 1 | Round bottom 3-neck flask |
| 1 | Overhead Stirrer |
| 1 | Dean Stark Trap |
| 1 | Condenser, Allihn, Drip tip |
| 1 | Heating mantle |
| 1 | Recirculating Chiller |
| 1 | Heavy duty distillation head |
| 1 | Fraction Cutter |
| 4 | 500 ml round bottom flask |
| 2 | Variac |
| 3 | Tubing (ft.) |

FIG. 20C

Procedure

2040

1. Into a 3 Neck Flask equipped with an overhead stirrer, Dean stark collector, condenser, and heating mantle was placed [0.0000] grams( [0.0000] mol) of 2-Bromopropionic acid.

2. To the 2-Bromopropionic acid was added [0.0000] grams ( [0.0000] mol) of Butanol.

3. To the 2-Bromopropionic acid/butanol mix was added [0.0000] grams ( [0.0000] mol) of Hexane.

4. To the flask is added [0.0000] grams of Dowex resin to facilitate the esterification. The resin is previously dried and has an activity of 3.68 grams/mol.

5. Two variacs are attached to the heating mantle and a setting of 50% power is used for heating to rapid reflux.

6. The reaction is monitored for water generation. After collecting [0.0000] grams ( [0.0000] mol) of water the reaction is complete.

7. Hexane is then removed by continuous draining of the dean stark collector.

8. The reaction is then cooled to room temperature and filtered through a fritted glass funnel to remove the Dowex resin.

9. The crude n-butyl-2-bromopropionate is then purified via vacuum distillation. [The vacuum distillation procedure is below]

Vacuum distillation

- The product is placed into a 5L round bottom and connected to the pilot scale distillation head equipped with a vigreux column. The material is heated in a 5L mantle set to 40-45% power with a variac.

- The product is collected at a head temp of 40-45 C. The material rapidly condenses once the apparatus is heated up. Total time for distillation is approx. 5 hours.

2050 — References

FIG. 21B

| | | | |
|---|---|---|---|
| Dowex 50W4-200 | 3.68 | 1 | 12.0000 | 44.1600 |
| Water | 18 | 1 | 12.0000 | 216.0000 |

2030 — Equipment needed

| Qty | Equipment |
|---|---|
| 1 | Round bottom 3-neck flask |
| 1 | Overhead Stirrer |
| 1 | Dean Stark Trap |
| 1 | Condenser, Allihn, Drip tip |
| 1 | Heating mantle |
| 1 | Recirculating Chiller |
| 1 | Heavy duty distillation head |
| 1 | Fraction Cutter |
| 4 | 500 ml round bottom flask |
| 2 | Variac |
| 3 | Tubing (ft.) |

FIG. 21C

Procedure 2040
1. Into a 3 Neck Flask equipped with an overhead stirrer, Dean stark collector, condenser, and heating mantle was placed [1835.7600] grams ([12.0000] mol) of 2-Bromopropionic acid.
2. To the 2-Bromopropionic acid was added [889.4401] grams ([12.0000] mol) of Butanol.
3. To the 2-Bromopropionic acid/butanol mix was added [1034.1600] grams ([12.0000] mol) of Hexane.
4. To the flask is added [44.1600] grams of Dowex resin to facilitate the esterification. The resin is previously dried and has an activity of 3.68 grams/mol.
5. Two variacs are attached to the heating mantle and a setting of 50% power is used for heating to rapid reflux.
6. The reaction is monitored for water generation. After collecting [216.0000] grams ([12.0000] mol) of water the reaction is complete.
7. Hexane is then removed by continuous draining of the dean stark collector.
8. The reaction is then cooled to room temperature and filtered through a fritted glass funnel to remove the Dowex resin.
9. The crude n-butyl-2-bromopropionate is then purified via vacuum distillation. [The vacuum distillation procedure is below]

Vacuum distillation
- The product is placed into a 5L round bottom and connected to the pilot scale distillation head equipped with a vigreux column. The material is heated in a 5L mantle set to 40-45% power with a variac.
- The product is collected at a head temp of 40-45C. The material rapidly condenses once the apparatus is heated up. Total time for distillation is approx. 5 hours.

2050
References

FIG. 27

Home > Search > Search Results — 2710

| | No. of Protocols |
|---|---|
| back next | |
| Displaying hits 1 - 20 of 255 | |
| Phthalaldehyde | 1 |
| Benzaldehyde | 34 |
| 4-Methoxybenzaldehyde | 7 |
| 3,4-Dihydroxybenzaldehyde | 2 |
| 4-Chlorobenzaldehyde | 7 |
| 3-Nitrobenzaldehyde | 4 |
| Benzaldehyde,3-hydroxy- | 4 |
| 2-Chlorobenzaldehyde | 2 |
| Benzaldehyde,2-hydroxy- | 3 |
| 2,4-Dihydroxybenzaldehyde | 1 |
| 2-Furancarboxaldehyde | 2 |
| Benzaldehyde,4-(dimethylamine)- | 1 |
| 3,4-Dimethoxybenzaldehyde | 3 |
| 4-Hydroxybenzaldehyde | 4 |
| Benzaldehyde,2-methoxy- | 3 |
| 2-Methylbenzaldehyde | 7 |
| 2-Nitrobenzaldehyde | 4 |
| Benzaldehyde,4-nitro- | 6 |
| Benzaldehyde,3-chloro- | 2 |

— 2720

Prev...Next    3 of 7  — 2730

Product: 4-Chlorobenzaldehyde
Yield: 98.09%  — 2740

Rxn View

Other Reagents
Silica gel; Water;methylene chloride;
Sulfuryl chloride;Methylene chloride;
Dispotassium carbonate;

Bibliographic Reference
Hojo, M.Masuda, R.Synthes/s, (1976)
Volume,Page: 678-680

FIG. 31
1. Query reactants
A) 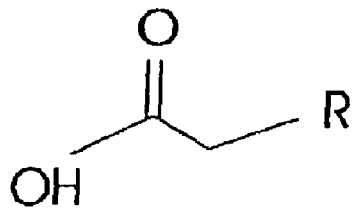
    1. Facturing by functional groups ⟶ Carboxylic acid
    2. Exact matches in dB?
B) 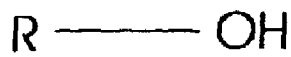
    1. Facturing by functional groups ⟶ alcohol
    2. Exact matches in dB?
2. Query products
C) 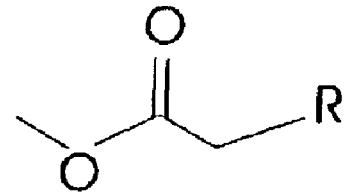
    1. Facturing by functional groups ⟶ Ester
    2. Exact matches in dB?
Carboxylic acid + alcohol ⟶ ester = esterification

SYSTEMS, METHODS AND COMPUTER PROGRAM PRODUCTS FOR DETERMINING PARAMETERS FOR CHEMICAL SYNTHESIS

CROSS-REFERENCE TO RELATED APPLICATIONS

This application is a continuation of application Ser. No. 10/395,713 filed Mar. 24, 2003, now issued as U.S. Pat. No. 7,250,950, which itself is a continuation-in-part of application Ser. No. 10/059,818, filed Jan. 29, 2002, entitled Systems, Methods and Computer Program Products for Determining Parameters for Chemical Synthesis and for Supplying the Reagents, Equipment and/or Chemicals Synthesized Thereby, which itself is a continuation-in-part of application Ser. No. 09/772,229, filed Jan. 29, 2001, entitled Systems, Methods and Computer Program Products for Determining Parameters for Chemical Synthesis and/or Supplying the Reagents, Equipment and/or Chemicals Synthesized Thereby, each of which are assigned to the assignee of the present invention, the disclosures of each of which are hereby incorporated herein by reference in their entirety as if set forth fully herein. Application Ser. No. 10/395,713 also claims priority from Provisional Application Ser. No. 60/367,993, filed Mar. 25, 2002, entitled Systems, Methods and Computer Program Products for Determining Parameters for Chemical Synthesis and for Supplying the Reagents, Equipment and/or Chemicals Synthesized Thereby, which is also assigned to the assignee of the present invention, the disclosure of which is hereby incorporated herein by reference in its entirety as if set forth fully herein.

FIELD OF THE INVENTION

This invention relates to data processing systems, methods and computer program products, and more particularly to systems, methods and computer program products for chemical synthesis.

BACKGROUND OF THE INVENTION

Chemicals are synthesized for various applications in commercial and academic environments. In chemical synthesis, a plurality of reagent chemicals are used to synthesize a target chemical, by reacting the reagent chemicals in predefined equipment according to a predefined procedure. The reagent chemicals, the target chemical, the equipment and the procedure provide the parameters for chemical synthesis.

The identification of the reagent chemicals, the equipment and the procedures to synthesize the target chemical may be contained within laboratory notebooks that are maintained by a commercial or academic organization. Moreover, the open literature also contains many references that can identify reagent chemicals, equipment and procedures that can be used to synthesize a target chemical. As one example, see Wolfe et al., *Highly Active Palladium Catalysts for Suzuki Coupling Reaction*, J. Am. Chem. Soc., Vol. 121, 1999, pp. 9550-9561. In the "Experimental Section" of this publication, various procedures are described for synthesizing aryl halides.

Unfortunately, it may be difficult to find an appropriate procedure for synthesizing a desired target chemical, and it also may be difficult and/or time consuming to identify and procure the reagent chemicals and/or equipment that are used to synthesize the desired target chemical.

SUMMARY OF THE INVENTION

Embodiments of the present invention provide systems, methods and computer program products for determining parameters for chemical synthesis in response to a user query that identifies a target chemical. In response to the user identification of the target chemical, a listing is displayed of reagent chemicals that are used to synthesize the target chemical. A listing also is displayed of equipment that is used to synthesize the target chemical. A listing also is displayed of a procedure that is used to synthesize the target chemical by reacting the reagent chemicals in the equipment according to the procedure.

Prior to accepting a user identification of a target chemical, a database is populated with a plurality of target chemicals, a plurality of corresponding listings of reagent chemicals, a plurality of corresponding listings of equipment and a plurality of corresponding listings of procedures. The database then is searched in response to a user identification of a target chemical. Thus, in embodiments of the present invention, target chemicals, their reagent chemicals, their equipment and their synthesis procedures may be entered into a database and may be queried by a user.

Some embodiments of the present invention provide a reaction editor for entering the data into the database. The reaction editor includes a plurality of icons that correspond to a plurality of operations that may be selectively used to generate a procedure that is used to synthesize the target chemical by reacting the corresponding reagent chemicals in the corresponding equipment according to the procedure. User entry of selected ones of the icons from the reaction editor is sequentially accepted to build the procedure. In some embodiments, the plurality of icons further correspond to at least one of flasks, atmospheres, time or temperature, that may be selectively used to generate a procedure that is used to synthesize a target chemical by reacting the corresponding reagent chemicals in the corresponding equipment according to the procedure. In other embodiments, the plurality of icons that correspond to a plurality of operations comprise icons for at least some of the following operations: add, mix, dissolve, degas, evacuate, heat, cool, reflux, stir, shake, extract, wash, distill, dry, filter, recrystallize, concentrate, chromatograph, titrate, titurate, and rotovap. Accordingly, a reaction editor can facilitate entry of the procedure in some embodiments of the present invention.

Other embodiments of the present invention provide a context-sensitive Boolean query option generator that is used to generate a user query of the database to identify the target chemical. In particular, in some embodiments, a user criterion is accepted for identifying a target material. Boolean query options that apply to the user criterion that was accepted are displayed to the user. The accepting of a user criterion and the displaying of the Boolean query options is repeated, to build a user query of the database. The user query then may be run on the database to identify one or more target chemicals.

Yet other embodiments of the invention allow searching for similar reactions and/or predictive chemistry that can identify reactions based upon similar known reactions. In particular, in some embodiments, the target chemical is not one of the plurality of target chemicals in the database. Accordingly, in response to a query, a display is provided that comprises a listing of reagent chemicals that are predicted to synthesize the target chemical, a listing of equipment that is predicted to be used to synthesize the target chemical, and a listing of a procedure that is predicted to be used to synthesize the target chemical by reacting the predicted reagent chemicals in the predicted equipment according to the predicted procedure. In some embodiments, after accepting a user identification of a target chemical, a determination is made that a procedure is not available for synthesizing the target chemical. A procedure is identified that may be used to synthesize a constituent part of the target chemical and/or a chemical that is similar to the target chemical. The procedure that is identified is modified to obtain a predicted procedure that may be used to synthesize the target chemical. A listing of predicted reagent chemicals that may be used to synthesize the target chemical, a listing of predicted equipment that may be used to synthesize the target chemical and a listing of the predicted procedure that may be used to synthesize the target chemical by reacting the predicted reagent chemicals in the predicted equipment according to the predicted procedure may be displayed in response to the user identification of the target chemical.

Still other embodiments of the present invention display the target chemical as a hub, reagent chemicals that are used to synthesize the target chemical as spokes leading to the hub and additional chemicals in which the target chemical is a reagent chemical as spokes emerging from the hub. In other embodiments, additional reagent chemicals that are used to synthesize the reagent chemicals are further displayed as spokes leading to the reagent chemicals, and chemicals in which the additional chemicals are reagent chemicals are further displayed as spokes emerging from the additional chemicals. Accordingly, a "reaction relay" display may be provided.

Moreover, in other embodiments, a user input of one of the reagent chemicals that are used to synthesize the target chemical or one of the additional chemicals in which the target chemical is a reagent chemical is accepted from the user, to provide a new target chemical. The new target chemical is displayed as a hub, with reagent chemicals that are used to synthesize the new target chemical are displayed as spokes leading to the hub and additional chemicals in which the new target chemical is a reagent chemical are displayed as spokes emerging from the hub. Moreover, in other embodiments, after displaying the target chemicals as a hub, and reagent chemicals and additional chemicals as spokes, a user input, may be accepted of one of the reagent chemicals that are used to synthesize the target chemical or one of the additional chemicals in which the target chemical is a reagent chemical, to define a new target chemical. A reaction flowchart then is displayed to indicate connected chemistries to the new target chemical, as will now be described.

In particular, these embodiments can display a flowchart that graphically indicates first reagent chemicals that are used to synthesize the new target chemical, second reagent chemicals that are used to synthesize the first reagent chemicals, third reagent chemicals that are used to synthesize the second reagent chemicals, etc. The flowchart also graphically indicates procedures that are used to synthesize the second reagent chemicals from the third reagent chemicals, the first reagent chemicals from the second reagent chemicals and the new target chemical from the first reagent chemicals, etc.

In some embodiments, the flowchart comprises a plurality of nodes that are linked by branches. A respective node corresponds to the new target chemical, a first reagent chemical, a second reagent chemical, a third reagent chemical, etc. A respective branch corresponds to a procedure that is used to synthesize the new target chemical, the first reagent chemical, the second reagent chemical, the third reagent chemical, etc., which corresponds to a node that is linked to the respective branch. In other embodiments, a respective branch corresponds to the new target chemical, a first reagent chemical, a second reagent chemical, a third reagent chemical, etc. A respective node corresponds to a procedure that is used to synthesize the new target chemical, the first reagent chemical, the second reagent chemical, the third reagent chemical, etc., which corresponds to a branch that is linked to the respective node. Accordingly, connected chemistries may be graphically illustrated.

BRIEF DESCRIPTION OF THE DRAWINGS

FIGS. 4-14 illustrate displays that may be used for data entry according to embodiments of the present invention.

FIG. 16 illustrates a display that may be used to enter a reference according to embodiments of the present invention.

FIGS. 18 and 19 illustrate displays that may be used for performing queries according to embodiments of the present invention.

FIG. 27 is a flowchart that may be used to perform reaction triage according to embodiments of the present invention.

FIGS. 30A-30C and 31 are examples of predictive chemistry according to embodiments of the present invention.

DETAILED DESCRIPTION OF PREFERRED EMBODIMENTS

Figure 1A:
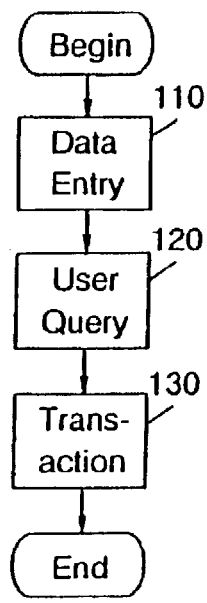
FIG. 1A-1G are block diagrams of systems, methods and/or computer program products according to embodiments of the present invention.

The present invention now is described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout the description of the drawings.

As also will be appreciated by one of skill in the art, the present invention may be embodied as methods, data processing systems, and/or computer program products. Accordingly, the present invention may take the form of an entirely hardware embodiment, an entirely software embodiment running on general purpose hardware or an embodiment combining software and hardware aspects. Furthermore, the present invention may take the form of a computer program product on a computer-usable storage medium having computer-usable program code embodied in the medium. Any suitable computer readable medium may be utilized including hard disks, CD-ROMs, optical storage devices, or magnetic storage devices.

Computer program code for carrying out operations of the present invention may be written in an object oriented programming language such as JAVA®, Smalltalk or C++. The computer program code for carrying out operations of the present invention may also be written in a conventional procedural programming language, such as "C". Microsoft Active Server Pages (ASP) technology and Java Server Pages (JSP) technology may be utilized. Software embodiments of the present invention do not depend on implementation with a particular programming language. The program code may execute entirely on one or more Web servers and/or application servers, or it may execute partly on one or more Web servers and/or application servers and partly on a remote computer (i.e., a user's Web client), or as a proxy server at an intermediate point in a network. In the latter scenario, the remote computer may be connected to the Web server through a LAN or a WAN (e.g., an intranet), or the connection may be made through the Internet (e.g., via an Internet Service Provider).

The present invention is described below with reference to block diagram and flowchart illustrations of methods, apparatus (systems) and computer program products according to embodiments of the invention. It will be understood that each block of the block diagrams and/or flowchart illustrations, and combinations of blocks, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create structures for implementing the functions specified in the block diagram and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function specified in the block diagram and/or flowchart block or blocks.

The computer program instructions may also be loaded onto a computer or other programmable data processing apparatus to cause a series of operational steps to be performed on the computer or other programmable apparatus to produce a computer implemented process or method such that the instructions which execute on the computer or other programmable apparatus provide steps for implementing the functions specified in the block diagram and/or flowchart block or blocks.

In order to provide a complete description of preferred embodiments of the invention in a systematic manner, an overview first will be provided. Detailed embodiments of the invention then will be described.

Overview

Referring now to FIGS. 1A-1G, block diagrams of systems, methods and/or computer program products according to embodiments of the present invention are shown. In embodiments of FIG. 1A, data entry 110 is provided, wherein a plurality of target chemicals, a plurality of corresponding listings of reagent chemicals that are used to synthesize the plurality of target chemicals, a plurality of corresponding listings of equipment that is used to synthesize the plurality of target chemicals and a plurality of corresponding listings of procedures that are used to synthesize the plurality of target chemicals by reacting the corresponding reagent chemicals in the corresponding equipment according to the corresponding procedure, are entered into a database. At Block 120, a user query that identifies a target chemical is accepted, and a listing of reagent chemicals that are used to synthesize the target chemical, a listing of equipment that is used to synthesize the target chemical, and a listing of the procedure that is used to synthesize the target chemical by reacting the reagent chemicals in the equipment according to the procedure, is displayed in response to the user identification of the target chemical. Finally, at Block 130, a transaction accepts a user input to electronically order the reagent chemicals that are used to synthesize the target chemical, the target chemical itself and/or the equipment that is used to synthesize the target chemical, and the reagent chemicals, target chemical and/or the equipment is electronically ordered in response to the user input.

Figure 1B:
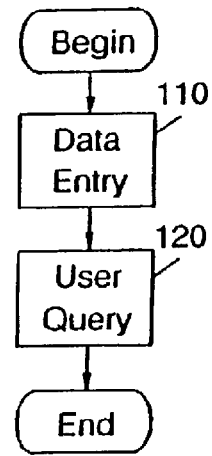
Figure 1C:
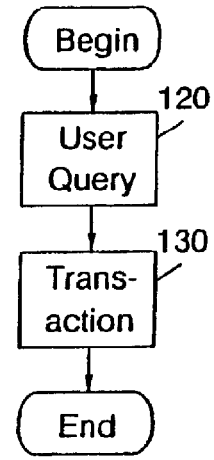
Figure 1D:
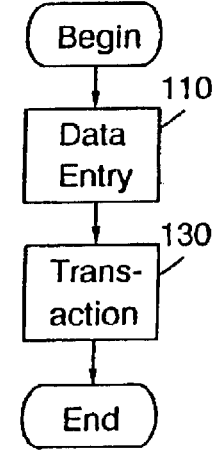

As shown in FIGS. 1B-1D, various combinations of data entry 110, user query 120 and transactions 130 may be provided according to embodiments of the present invention. Thus, for example, in FIG. 1B, data entry 110 is provided to enter into a database, a plurality of target chemicals, a plurality of corresponding listings of reagent chemicals, a plurality of corresponding listings of equipment, and a plurality of corresponding listings of procedures. A user query 120 then may be performed by accepting a user identification of a target chemical, and displaying the corresponding listing of reagent chemicals, equipment and procedure. In embodiments of FIG. 1B, transactions need not be performed electronically. Moreover, in FIG. 1C, a user query 120 of a preexisting database may be provided wherein, in response to a user identification of a target chemical, a display of a listing of reagent chemicals, a listing of equipment and a listing of a procedure is provided. At Block 130, a transaction then may be performed to electronically order the reagent chemicals, the target chemical, and/or the equipment. Finally, in Figure lD, data entry 110 is provided to enter into a database target chemicals, corresponding reagent chemicals, corresponding equipment and corresponding procedures, and then a transaction 130 may be performed from the database without a query.

Figure 1E:
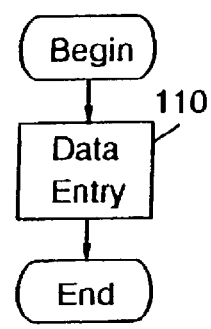
Figure 1F:
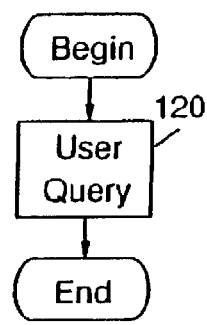
Figure 1G:
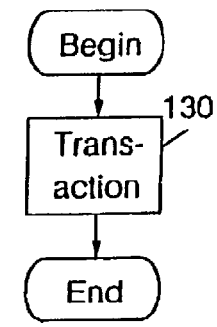

As also shown in FIG. 1E-1G, data entry 110, user query 120 and transactions 130 may be used separately according to embodiments of the present invention. Thus, in FIG. 1E, data entry 110 may be used to populate a database of a plurality of target chemicals, a plurality of corresponding listings of reagent chemicals, a plurality of corresponding listings of equipment and a plurality of corresponding listings of procedures. This database may include three related databases: a chemical database, an equipment database and a supplier database. As part of a data entry, a plurality of target chemicals, a plurality of first pointers to a corresponding plurality of listings of reagent chemicals in the chemical database, a plurality of second pointers to a corresponding plurality of listings of equipment in the equipment database, and a plurality of corresponding listings of procedures are entered into the chemical database. The plurality of listings of equipment are entered into the equipment database, along with a plurality of third pointers to a corresponding plurality of listings of equipment suppliers in the supplier database. The listings of equipment suppliers are entered into the supplier database. This database or databases may be used as was described in FIGS. 1A, 1B and 1D, and/or for other purposes, such as archival purposes.

As part of data entry, a narrative description of steps of the corresponding procedure may be interactively generated and entered into a database, using the corresponding listing of the reagent chemicals and the corresponding listing of equipment. In particular, user entry of a listing of reagent chemicals that are used in a next step of a procedure to synthesize a target chemical, user entry of a listing of corresponding equipment that is used in the next step, and user entry of the next step may be accepted in response to user indication that the next step is present in the procedure. The target chemical, reagent chemicals, equipment and procedures may be obtained from a publication related to synthesis of the target chemical and/or from proprietary data related to synthesis of the target chemical, for example in lab notebooks.

Moreover, as shown in FIG. 1F, user queries 120 of preexisting databases may be performed to accept a user identification of a target chemical and display a corresponding listing of reagent chemicals, equipment and a procedure. In embodiments of user queries, the user may identify the target chemical by formula, chemical structure, chemical compound name and/or CAS number. Moreover, in response to a user query, a listing of target chemicals that match the user query may be displayed, and a user selection of a target chemical from the listing of target chemicals may be accepted. The listing of target chemicals may be prioritized, based, for example, on the extent of match to the user query. The listings of reagent chemicals, equipment and procedures corresponding to the user-selected target chemical then may be displayed. In yet other embodiments, a user identification of a reaction type may be accepted, and a listing of target chemicals that are synthesized using the reaction type may be displayed. A user selection of a target chemical then may be accepted from the listing of target chemicals.

In yet other query embodiments, backward searching may be performed. In particular, a listing of procedures that can be used to synthesize a target chemical may be displayed in response to a user identification of the target chemical. A user selection of a procedure from the listing of procedures may be accepted, and the listing of reagent chemicals, equipment and the procedure may be displayed in response to the user selection of the procedure. In other query embodiments, forward searching may be performed. In particular, a listing of procedures is displayed that use the target chemical as a reagent chemical, in response to user identification of the target chemical. A user selection of a procedure is accepted. In still other query embodiments, after accepting a user identification of a target chemical, a user selection of a desired quantity of the target chemical is accepted. The listing of the reagent chemicals then is scaled, so as to synthesize the desired quantity of the target chemical. Then, a scaled listing of reagent chemicals, a listing of equipment that is used to synthesize the desired quantity of the target chemical and the listing of the procedure that is used to synthesize the desired quantity of the target chemical is displayed.

Finally, referring to FIG. 1G, transactions 130 may be performed independently by electronically ordering the target chemicals, reagent chemicals that are used to synthesize the target chemical and/or equipment that is used to synthesize the target chemical from an electronically displayed listing of the reagent chemicals, of the equipment and of a procedure, in response to user input. In some embodiments of transactions 130, a kit of reagent chemicals that are used to synthesize the target chemical is ordered. In other embodiments, a kit of the equipment that is used to synthesize the target chemical is ordered. Both kits also may be ordered. In yet other embodiments, the target chemical itself is ordered.

Detailed Embodiments

Some embodiments of the present invention may be practiced on a single computer, for example using a client-server architecture. However, because other embodiments of the present invention may involve storage and/or searching of large numbers of target chemicals and their corresponding reagent chemicals, equipment and procedures, embodiments of the present invention may be implemented on a client-server system, wherein at least one client computer and at least one server computer are connected over a network, such as the Internet.

The Internet is a worldwide decentralized network of computers having the ability to communicate with each other. The Internet has gained broad recognition as a viable medium for communicating and for conducting business. The World-Wide Web (Web) was created in the early 1990's, and is comprised of server-hosting computers (Web servers) connected to the Internet that have hypertext documents (referred to as Web pages) stored therewithin. Web pages are accessible by client programs (e.g., Web browsers) utilizing the Hypertext Transfer Protocol (HTTP) via a Transmission Control Protocol/Internet Protocol (TCP/IP) connection between a client-hosting device and a server-hosting device. While HTTP and Web pages are the prevalent forms for the Web, the Web itself refers to a wide range of protocols including Secure Hypertext Transfer Protocol (HTTPS), File Transfer Protocol (FTP), and Gopher, and Web content formats including plain text, HyperText Markup Language (HTML), Extensible Markup Language (XML), as well as image formats such as Graphics Interchange Format (GIF) and Joint Photographic Experts Group (JPEG).

A Web site generally comprises a related collection of Web files that includes a beginning file called a "home" page. From the home page, a visitor can access other files and applications at a Web site. A large Web site may utilize a number of servers, which may or may not be different and which may or may not be geographically-dispersed. For example, the Web site of the International Business Machines Corporation (www.ibm.com) includes thousands of Web pages and files spread out over multiple Web servers in locations world-wide.

A Web server (also referred to as an HTTP server) is a computer program that generally utilizes HTTP to serve files that form Web pages to requesting Web clients. Exemplary Web servers include International Business Machines Corporation's family of Lotus Domino® servers, the Apache server (available from www.apache.org), and Microsoft's Internet Information Server (IIS), available from Microsoft Corporation, Redmond, Wash. A Web client is a requesting program that also generally utilizes HTTP. A browser is an exemplary Web client for use in requesting Web pages and files from Web servers. A Web server waits for a Web client, such as a browser, to open a connection and to request a specific Web page or application. The Web server then sends a copy of the requested item to the Web client, closes the connection with the Web client, and waits for the next connection.

HTTP allows a browser to request a specific item, which a Web server then returns and the browser renders. To ensure that browsers and Web servers can interoperate unambiguously, HTTP defines the exact format of requests (HTTP requests) sent from a browser to a Web server as well as the format of responses (HTTP responses) that a Web server returns to a browser. Exemplary browsers that can be utilized with the present invention include, but are not limited to, Netscape Navigator® (America Online, Inc., Dulles, Va.) and Internet Explorer™ (Microsoft Corporation, Redmond, Wash.). Browsers typically provide a graphical user interface for retrieving and viewing Web pages, applications, and other resources served by Web servers.

As is known to those skilled in this art, a Web page is conventionally formatted via a standard page description language such as HTML, which typically contains text and can reference graphics, sound, animation, and video data. HTML provides for basic document formatting and allows a Web content provider to specify anchors or hypertext links (typically manifested as highlighted text) to other servers. When a user selects a particular hypertext link, a browser running on the user's client device reads and interprets an address, called a Uniform Resource Locator (URL) associated with the link, connects the browser with a Web server at that address, and makes a request (e.g., an HTTP request) for the file identified in the link. The Web server then sends the requested file to the client device which the browser interprets and renders within a display screen.

Figure 2:
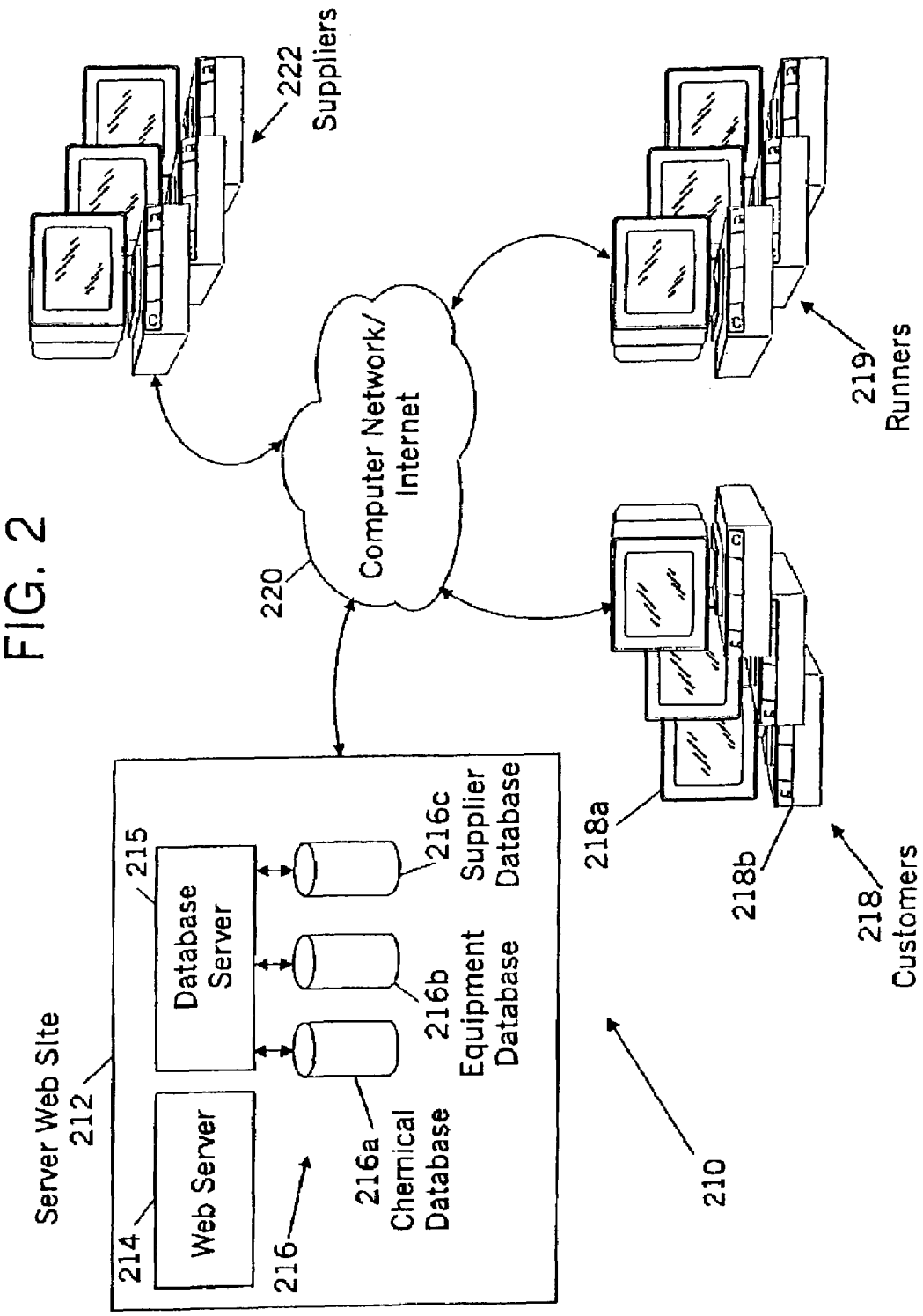
FIG. 2 is a diagram of computer systems that can practice methods and/or include computer program products according to embodiments of the present invention.

Referring now to FIG. 2, a computer system 210 that can practice methods and/or include computer program products according to embodiments of the present invention, is schematically illustrated. The illustrated system 210 includes a server Web site 212 and a plurality of users, also referred to herein as "customers", who can perform user queries 120 of FIG. 1A-1G and/or perform transactions 130 of FIGS. 1A-1G, and who communicate with the server Web site 212 from customer sites 218 over a computer network, such as the Internet 220. Customer sites 218 may include a computer display 218a and a computer 218b. A pointing device such as a mouse also may be included.

The server Web site 212 includes a Web server 214, such as a Java Web server, a database server 215 and one or more databases 216. As shown in FIG. 2, the databases 216 may include a chemical database 216a, an equipment database 216b and a supplier database 216c. Other databases also may be provided. Although a single Web server 214 and database server 215 are illustrated, it will be understood that multiple Web servers and multiple database servers (including other application servers) may be utilized according to embodiments of the present invention.

The Web server 214 is the "front end" component of the Web site 212, and is configured to handle requests from customer sites 218 that access the Web site 212. The Web server 214 can include program code, logic and graphics, to interface with the customer sites 218. Exemplary commercial Web servers that may be utilized as a Web server 214 in the illustrated system 210 are Apache, available from the Apache Server Project, http://www.apache.org; Microsoft's Internet Information Server (IIS), available from Microsoft Corporation, Redmond, Wash.; and Netscape's FastTrack®) and Enterprise™ servers, available from America Online, Inc., Dulles, Va. Other Web servers that may be utilized include Novell's Web Server for users of its NetWare® operating system, available from Novell, Inc., San Jose, Calif.; and IBM's family of Lotus Domino® servers, available from International Business Machines Corporation, Armonk, N.Y.

As is known by those of skill in the art, a database is a collection of data that is organized in tables or other conventional forms of organization. A database typically includes a database manager and/or database server 215 that facilitates accessing, managing, and updating data within the various tables of a database. Exemplary types of databases that can be used to implement the chemical database 216a, equipment database 216b, and supplier database 216c of the present invention include relational databases, distributed databases (databases that are dispersed or replicated among different points in a network), and object-oriented databases. Relational, distributed, and object-oriented databases are well understood by those of skill in the art and need not be discussed further herein.

The database server 215 operates as a "middleman" server between the Web server 214 and the plurality of databases 216a-216c. The database server 215 generally includes program code and logic for retrieving data from the databases 216a-216c (and from sources external to the Web site 212) in response to requests from the Web server 214. Commercial database servers that may be utilized as a database server 214 in the illustrated system 210 include Microsoft's SQL server, IBM DB2® Universal Database server, the latter being available from International Business Machines Corporation, Armonk, N.Y.

FIG. 2 illustrates a plurality of databases 216 including a chemical database 216a, an equipment database 216b and a supplier database 216c. However, it will be understood that one or more of these databases may be combined into a single database and that other databases also may be provided at the server Web site 212.

Data structures of the databases 216a-216c according to embodiments of the invention now will be described. In embodiments of the invention, the chemical database 216a includes listings of a plurality of target chemicals, a plurality of first pointers to a corresponding plurality of listings of reagent chemicals in the chemicals database 216a that are used to synthesize the plurality of target chemicals, a plurality of second pointers to a corresponding plurality of listings of equipment in the equipment database 216b, and a plurality of corresponding listings of procedures that are used to synthesize the plurality of target chemicals by reacting the corresponding reagent chemicals in corresponding equipment according to the corresponding procedure. Table 1 provides an example of an architecture of a chemical database 216a according to embodiments of the present invention.

TABLE 1

Chemical Database 216a

| ATTRIBUTE | TYPE | DESCRIPTION |
|---|---|---|
| name | text | the compound name such as 4-Acetylbiphenyl |
| id | integer | unique identifier within Table 1 |
| entered_by | text | the runner who input the data |
| first_entered | timestamp | date/time entry was first entered |
| modified_by | text | name of last person who modified this record |
| last_modified | timestamp | date/time entry was last modified |
| ref | text | the journal references |
| image_url | text | pointer to the graphic for this compound which is stored on the web server 214 |
| recipe | text | the protocol text |
| chemicals | integer[ ] | first pointers (using the 'id' field) to reagents needed. Points to other records in the chemical database 216a |
| equipment | integer[ ] | second pointers to records in the equipment database 216b |
| cas | text | the CAS number |
| formula | text | the formula |
| mweight | float8 | molecular weight |
| quantity | float8[ ] | arrays of integers corresponding to quantity of each equipment |
| equivalent | float8[ ] | equivalent of this compound |
| yield | float8 | the yield for this protocol |
| flask_name | text | the name of the flask used |
| info | text | keywords |
| density | float8 | density of this compound |
| bplo | float8 | boil point range, low end |
| pbhi | float8 | boil point range; high end |
| fp | float8 | flash point |
| vp | text | vapor pressure |
| mplo | float8 | melting point, low end |
| mphi | float8 | melting point, high end |
| beilstein | text | beilstein reference |
| other_names | text | other names |
| reagents | text | list of the reagents cas#s |
| smiles | text | structure description |
| reagent smiles | text | semicolon separated structure descriptions for the reagents |
| incompatible | text | semicolon separated incompatible chemicals |

The equipment database 216b contains a plurality of listings of equipment that can be used to synthesize various target chemicals. Table 2 illustrates an architecture of an equipment database 216b according to embodiments of the present invention.

TABLE 2

Equipment Database 216b

| ATTRIBUTE | TYPE | DESCRIPTION |
|---|---|---|
| name | text | name of equipment |
| id | integer | unique record identifier |
| suppliers | integer[ ] | third pointers ('id' value) into the supplier database 216c |
| unit | text | measured unit (ml, L, etc.) |
| our_price | money | our price per unit |
| om_price | money | average price for outside supplier |
| size | integer | volume (for flasks) |
| category | integer | integer describing type of item |

1 = flask
2 = additional equipment
3 = flask equipment

The supplier database 216c contains a listing of suppliers of reagent chemicals and/or equipment. Table 3 is an architecture of a supplier database 216c according to embodiments of the invention.

TABLE 3

Supplier Database 216c

| ATTRIBUTE | TYPE | DESCRIPTION |
|---|---|---|
| name | text | supplier name (company name) |
| id | integer | unique record identifier |
| address1 | text | |
| address2 | text | |
| city | text | |
| state | text | |
| website | text | |
| phone | text | |
| Index: supplier_id_key | integer | unique record identifier |

The server Web site 212 is accessible to customer sites 218 via a computer network such as the Internet 220. Customers can access the server Web site 212 via a client program, such as a browser and/or a custom software application, running on a client device, such as a personal computer 218b including a display 218a. However, it will be understood that other electronic devices such as personal digital assistants (PDAs), hand-held computers, Internet-ready phones, and WebTVs, may be utilized as client devices for accessing the Web site 212 in accordance with embodiments of the present invention.

The Web server 214 also is configured to communicate with various third parties according to embodiments of the present invention. As will be described below, the Web server 214 is configured to communicate with other users, often referred to as "runners", at runner sites 219, who perform data entry (Block 110 of FIGS. 1A-1B and 1D-1E) according to embodiments of the present invention. When using public domain sources, an "Experimental Section" may be the source of data entry as was described above with reference to the Wolfe et al. publication.

Moreover, in other embodiments, data entry may be performed within an entity, such as a corporation or university, using proprietary data that may be contained, for example, in lab notebooks. This can provide institutional memory archiving systems, methods and computer program products that can be used, for example, by large corporations or universities, to archive the results of many chemical synthesis experiments that are contained in lab notebooks. In yet other alternatives, a scientist who is involved in chemical synthesis can archive data that is being generated by the scientist during the course of chemical synthesis. Accordingly, in some embodiments, the customer sites 218 and the runner sites 219 may be combined into a single station.

Finally, the customer sites 218 may communicate with suppliers of chemicals and/or equipment at supplier sites 222, in performing a transaction 130 of FIGS. 1A, 1C-1D and 1G, via the Internet 220 and preferably through the Web server 214. Communications between the customer sites 218, runner sites 219, the server Web site 212 and supplier sites 222 are preferably established via the Internet 220. However, other communication methods and networks may be utilized, including direct-dial access and telephonic communications. Wireless or wire communications maybe used.

Figure 3:
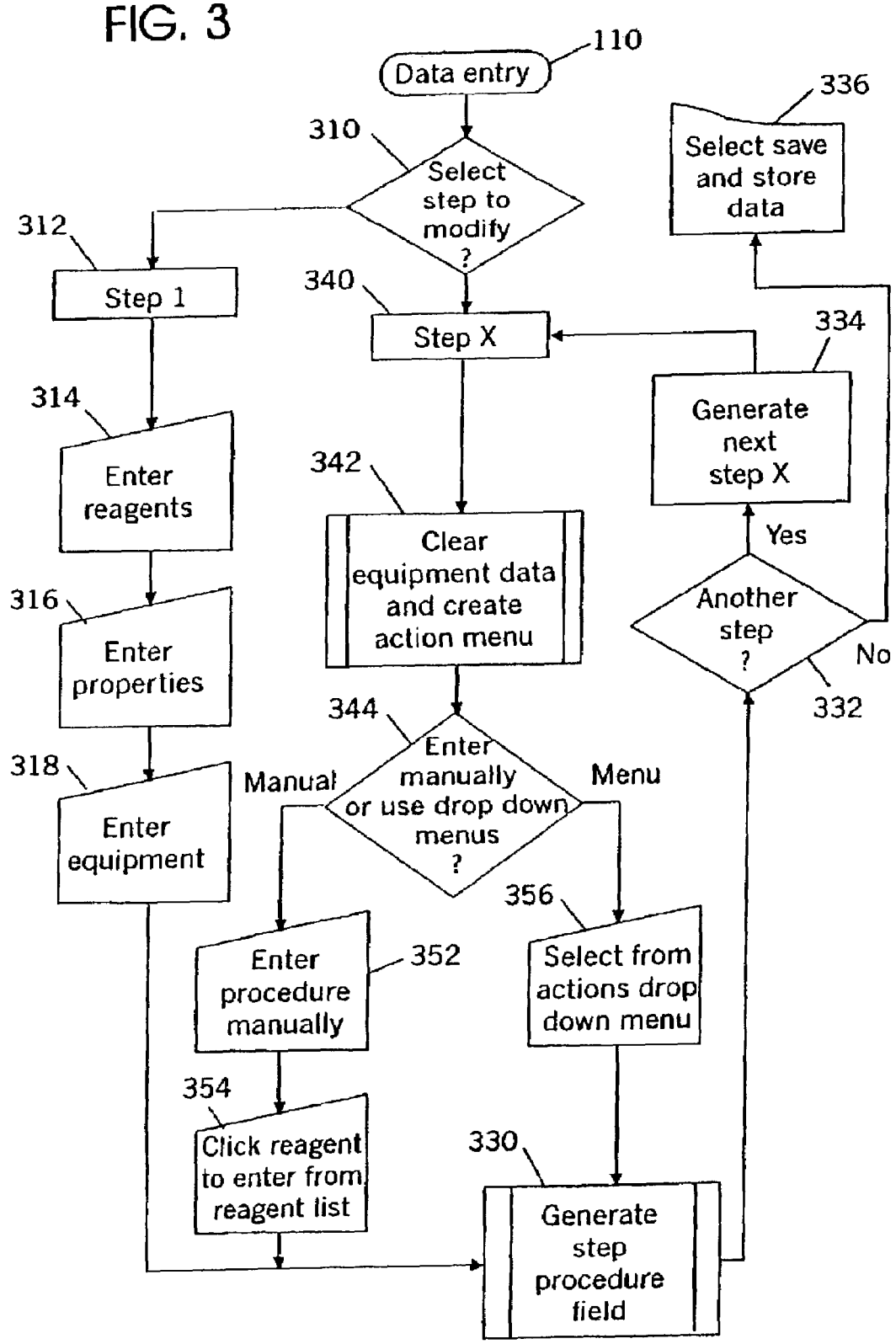
FIG. 3 is a flowchart of data entry according to embodiments of the present invention.

Referring now to FIG. 3, detailed operations for data entry (Block 110 of FIGS. 1A-1B and 1D-1E) now will be described. As was described above, data entry may be performed by users, also referred to herein as "runners" who may be tasked with a list of target chemicals for which to research public domain synthesis procedures and to enter these procedures in a data entry operation. The target chemicals may be derived from a list of target chemicals that are widely used in industrial and/or academic application. Target chemicals also may be identified based on user queries in a user query operation 120 of FIGS. 1A-1C and 1F, for which no target chemicals were identified. Other techniques for identifying target chemicals for database entry also may be used. Data entry operations 110 of FIG. 3 can facilitate the manual, semiautomatic or automatic entry of narrative procedures, reagent chemicals and equipment that is used to synthesize a target chemical by reacting the reagent chemicals in the equipment according to the procedure.

Figure 4:
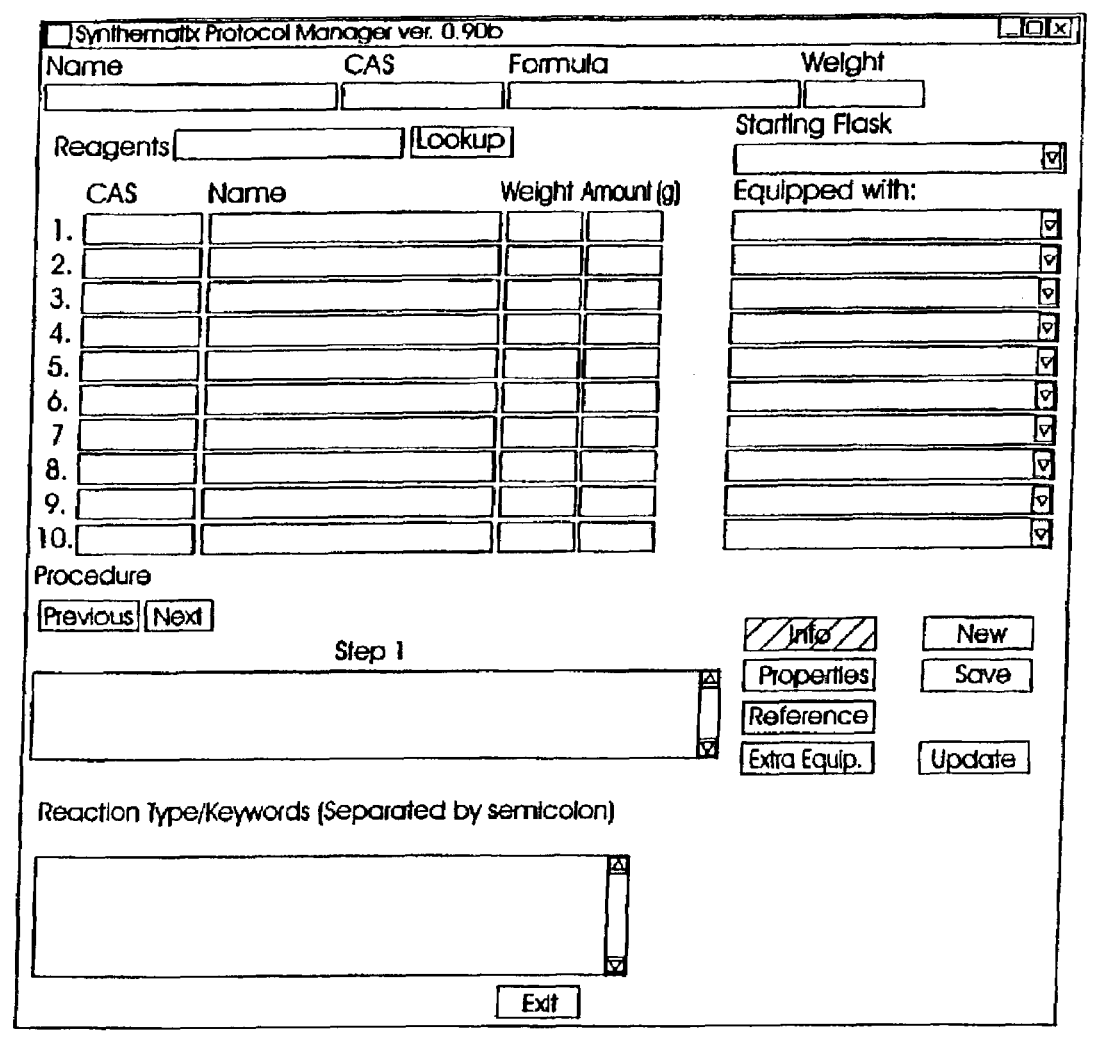

Referring now to FIG. 3, operations begin at Block 310, where the runner selects a step to modify. Thus, when entering data for a new procedure, Step 1 is selected at Block 312, for example by selecting the New button of the data entry display of FIG. 4.

Figure 5:
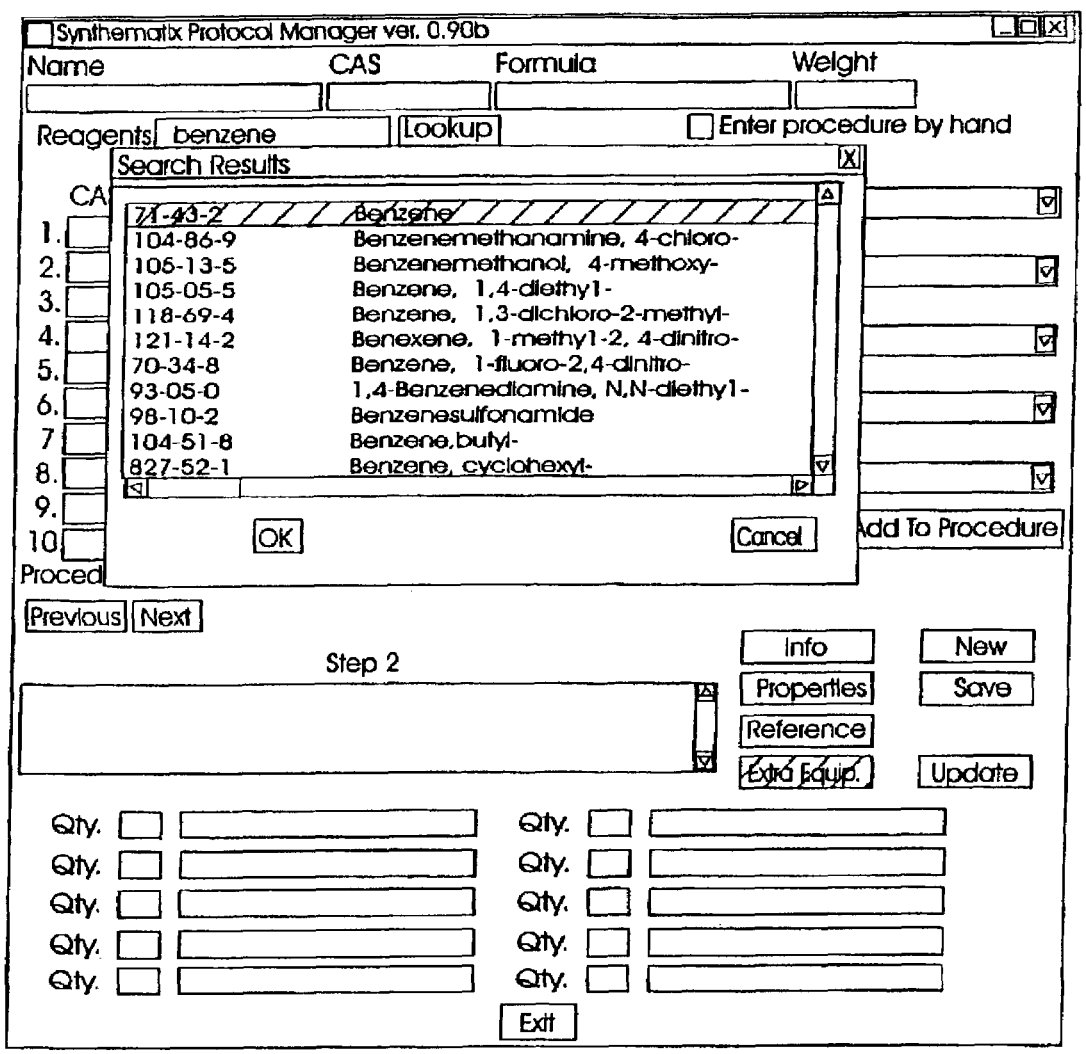
Figure 6:
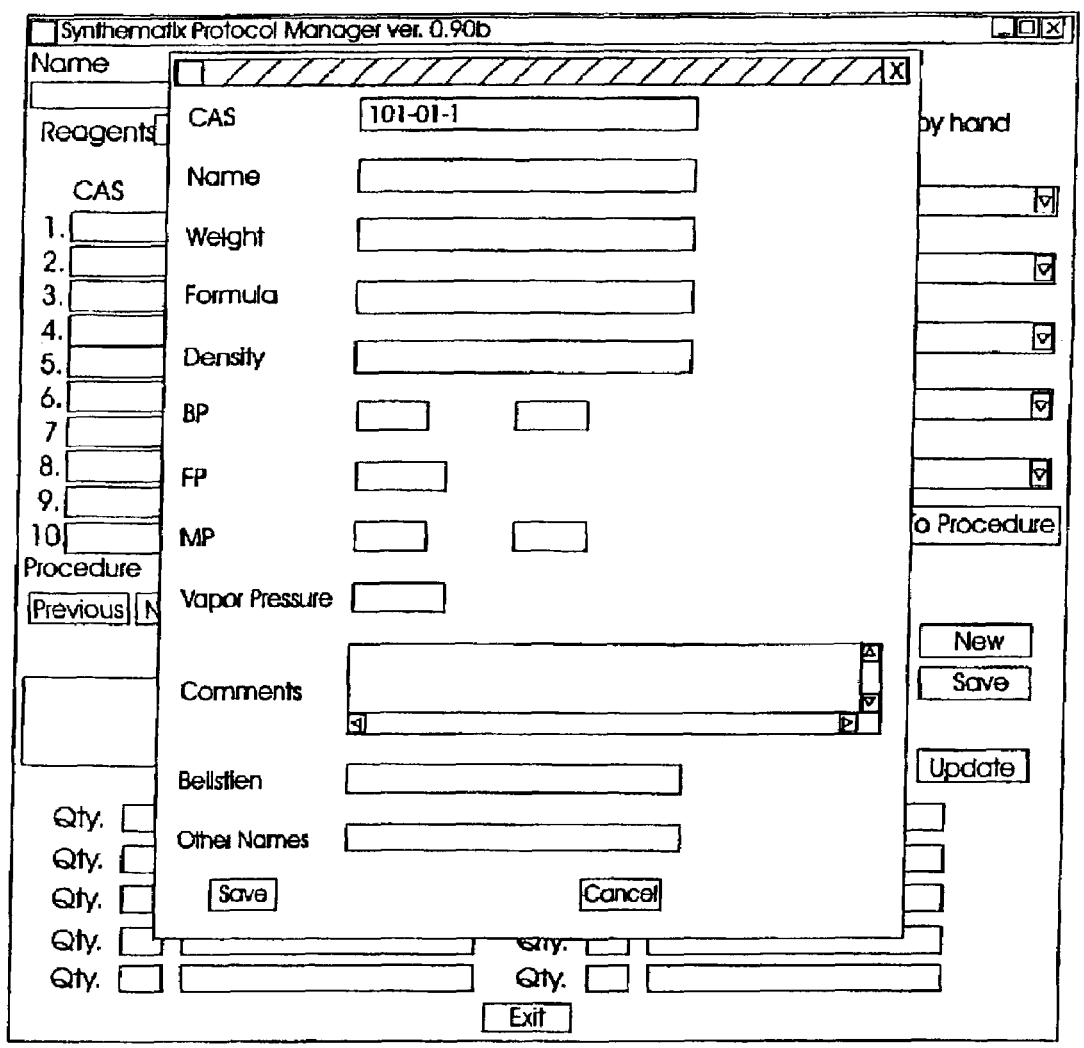

Referring to Block 314, the reagents for Step 1 are then entered. As shown in FIG. 5, reagents may be entered using a reagent lookup. Alternatively, as shown in FIG. 6, reagents may be entered via manual entry.

Figure 7:
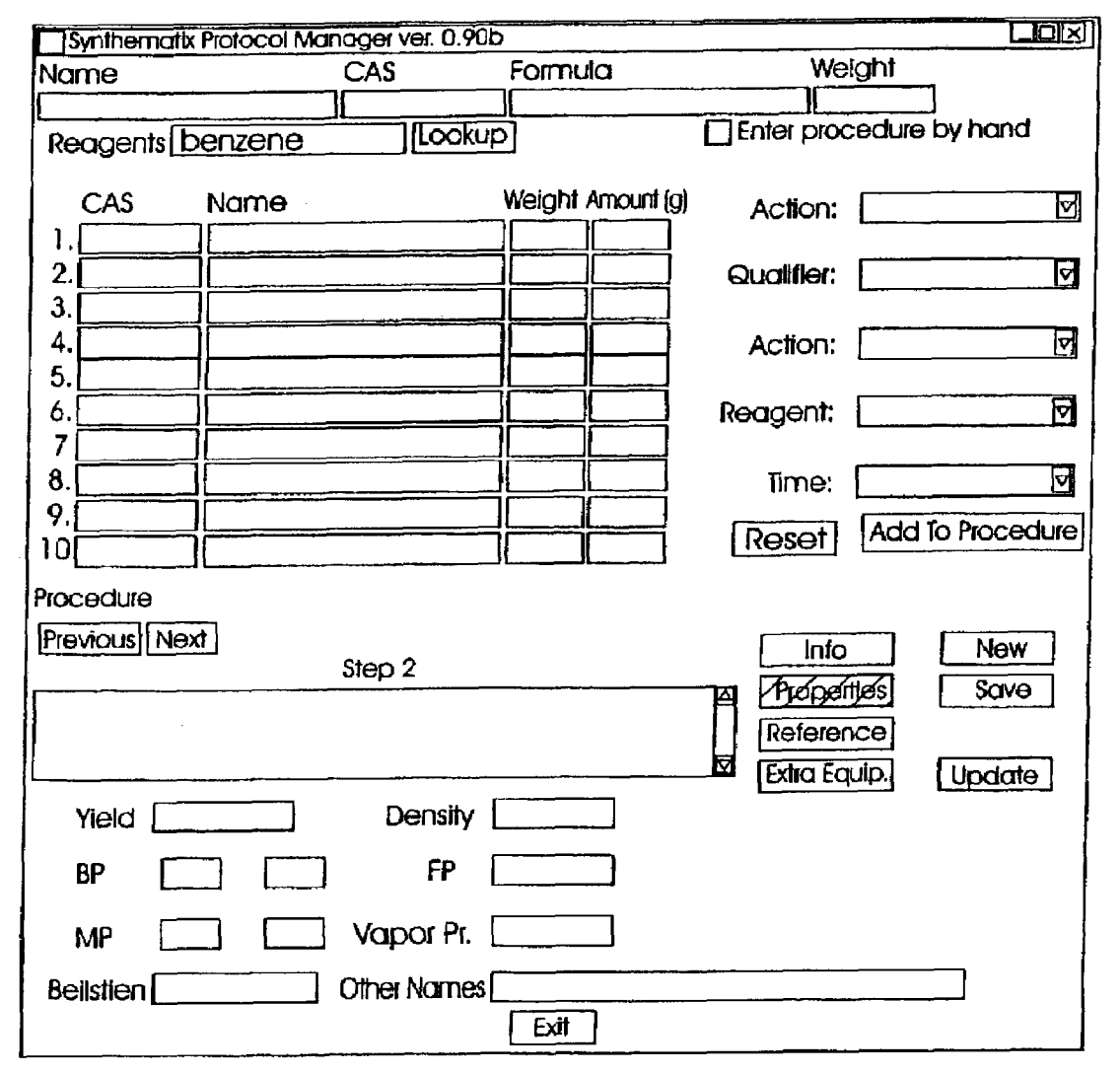

Then, referring to Block 316, various properties of the target chemical may be entered by selecting the Properties button of FIG. 7 and entering the properties shown at the bottom of FIG. 7. As shown, properties can include yield, density, boiling point (BP), flash point (FP), melting point (MP), vapor pressure, Beilstein number, other names and other properties.

Figure 8:
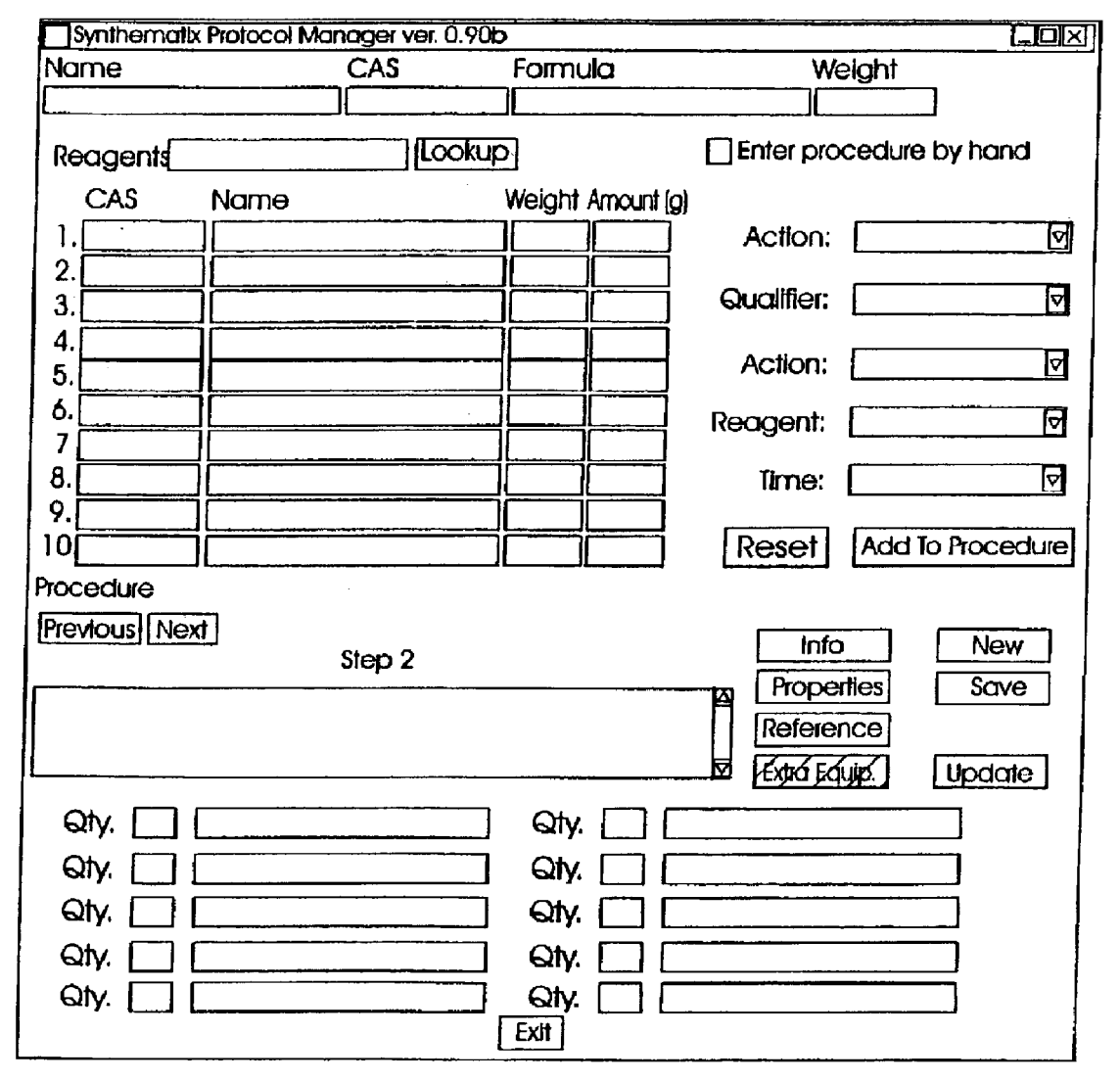
Figure 9:
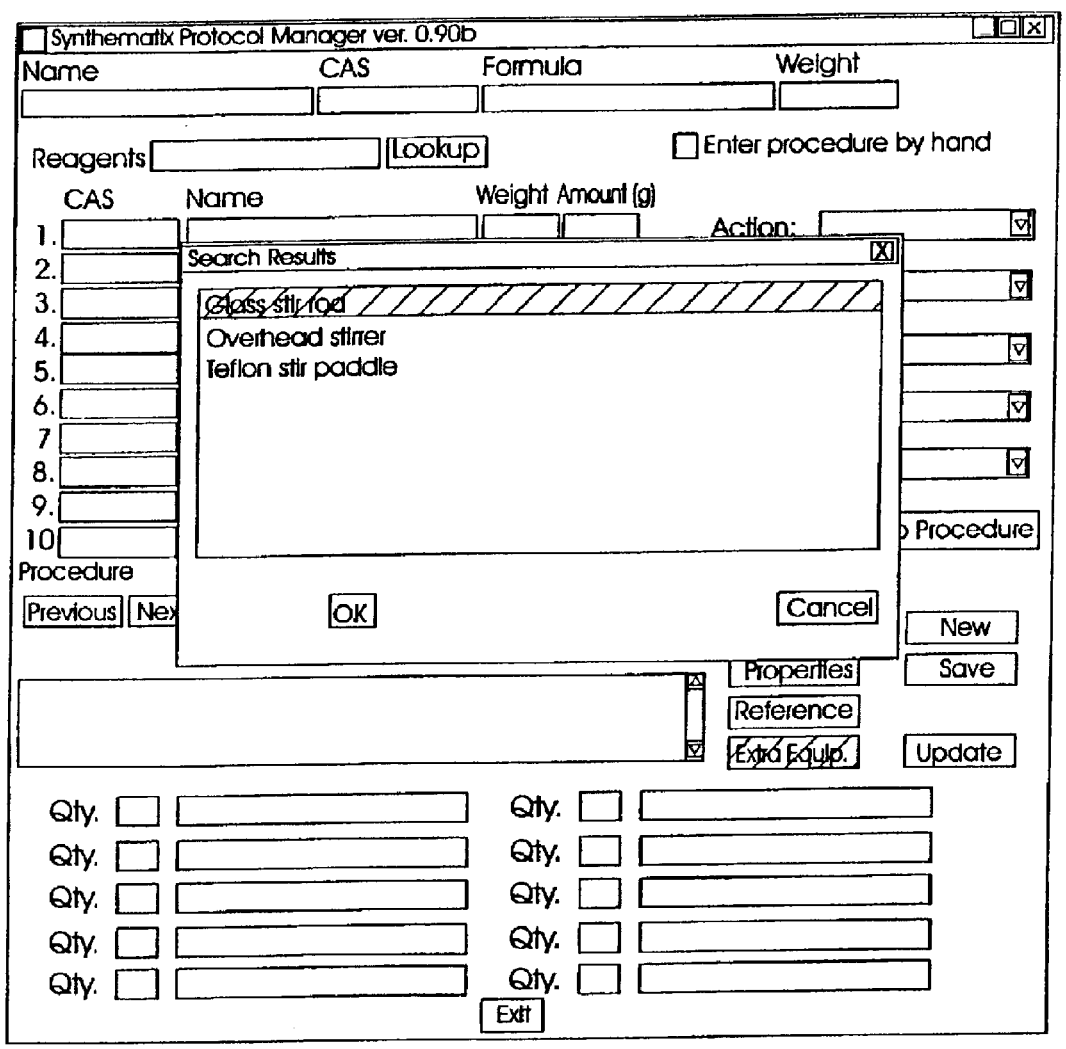

At Block 318, equipment then is entered, for example by manual entry on equipment lists as shown in FIG. 8 and/or by equipment lookup as shown in FIG. 9. It will be understood that the operations at Blocks 314, 316 and 318 may be performed in sequences that are different from that illustrated in FIG. 3.

Then, referring to Block 330, the narrative for the first step of the procedure can be generated interactively, for example using the first reagent and the starting equipment, as shown in FIG. 10. FIGS. 11 and 12 illustrate other examples of generation of a step of a procedure by selecting actions, qualifiers, reagents and times using pull-down menus.

Figure 14:
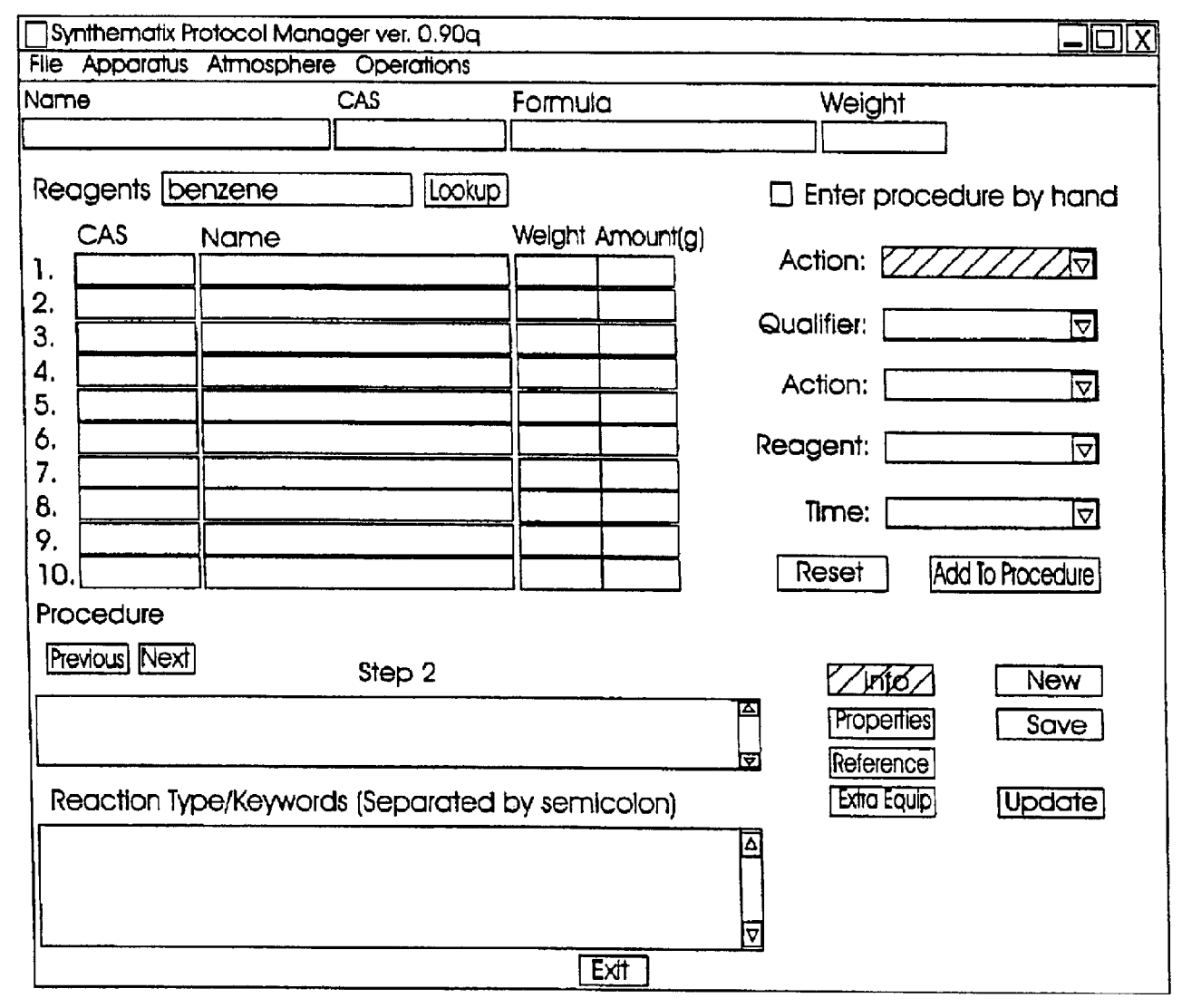

Assuming there is another step at Block 332, the next step may be selected (Block 334) by selecting the Next button as shown in FIG. 13. In particular, to generate the next step at Block 340, the equipment data is cleared and an action menu may be generated, as shown in FIG. 14. At Block 344, the runner is given the choice of entering the procedure manually or using the drop-down menu. If manually, then at Block 352, the procedure is typed in manually, and at Block 354, the reagent is entered from the reagent list by selection. Alternatively, if by drop-down menu, then the actions are selected from the drop-down menu at Block 356, for example as shown in FIG. 14.

For interactive entry, a common template for a procedure step may be provided, such as "into a _____ equipped with _____ is added _____". The runner can then supply the starting flask, equipment list and first reagent using pull-down menus and/or manual entries. The specific quantities may be provided using tags for molar quantities and gram quantities. These quantities may be scaled later, as will be described below.

Returning again to FIG. 3, when the last step has been entered at Block 332, the Save button (FIG. 4) may be selected and the data may be stored (Block 336) in the chemical database 216a and the equipment database 216b of FIG. 2. In particular, the target chemicals and the reagent chemicals may be stored in the chemical database 216a that was described in Table 1. The equipment may be entered into the equipment database 216b that was described in Table 2. Supplier data also may be entered into the supplier database 216c that was described in Table 3. Supplier data can be entered directly into the database 216c using the database server 215, and/or a graphical user interface may be provided to facilitate data entry.

The databases 216a may be populated as follows: The data may be read from a product data file and may be tab delimited. Complete entries may be separated by a new line. A call is made to a Java servelet located at the server Web site 212. The servelet accepts a connection and waits for the data. The runner site 219 sends the data and waits for a reply. The servelet at the server Web site 212 reads the data and inserts it into the database 216a at each new line, using the database server 215. The entry program also sends the date/time of the last time it updated. The servelet sends any new entries into the database since that time, and all entries in the database are timestamped. The servelet sends the current date/time and the entry program saves it to a file for the next time.

Figure 15:
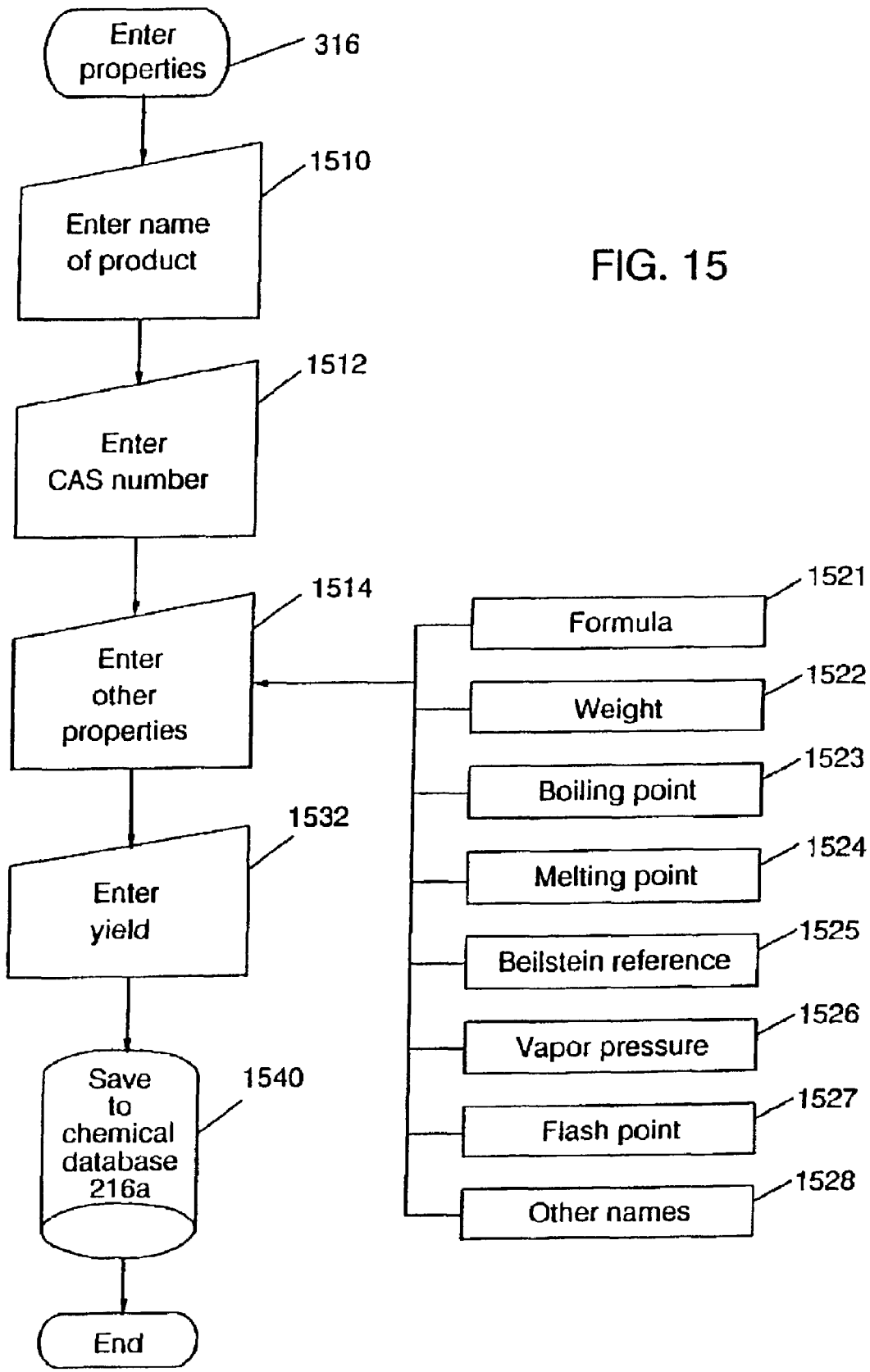
FIG. 15 is a flowchart of entering properties according to embodiments of the present invention.
Figure 16:
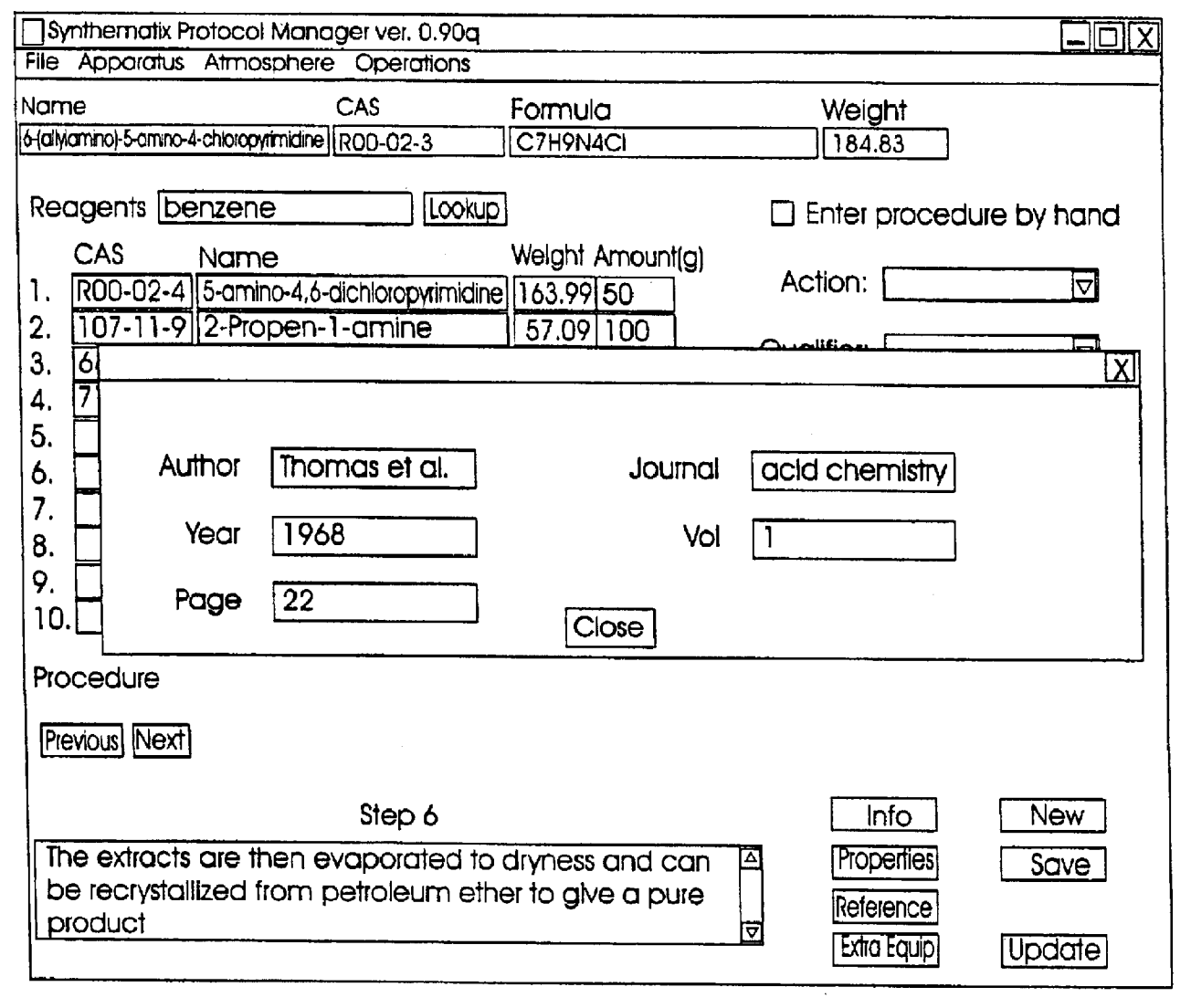

Referring now to FIG. 15, additional details for entering properties (Block 316 of FIG. 3), according to embodiments of the invention, now will be provided. As shown in FIG. 6, the name of the product can be entered in the "Name" field at Block 1510. The CAS number can be entered into the CAS field of FIG. 6 at Block 1512. Other properties may be entered at Block 1514. In particular, the formula (Block 1521) and weight (Block 1522) may be entered into the appropriate blocks of FIG. 6. The boiling point BP (Block 1523), melting point MP (Block 1524), Beilstein reference (Block 1525), vapor pressure (Block 1526), flash point (Block 1527) and other names (Block 1528) may be entered into the appropriate fields of FIG. 6. At Block 1532, the yield also may be entered into the appropriate block of FIG. 6. The Reference button of FIG. 4 also may be selected, and the reference to the publication where the procedure was obtained may be entered, for example using the pop-up window of FIG. 16. Then, at Block 1540, the information that was entered is saved into the appropriate fields of the chemical database 16a, for example using the format shown in Table 1 above.

Figure 17:
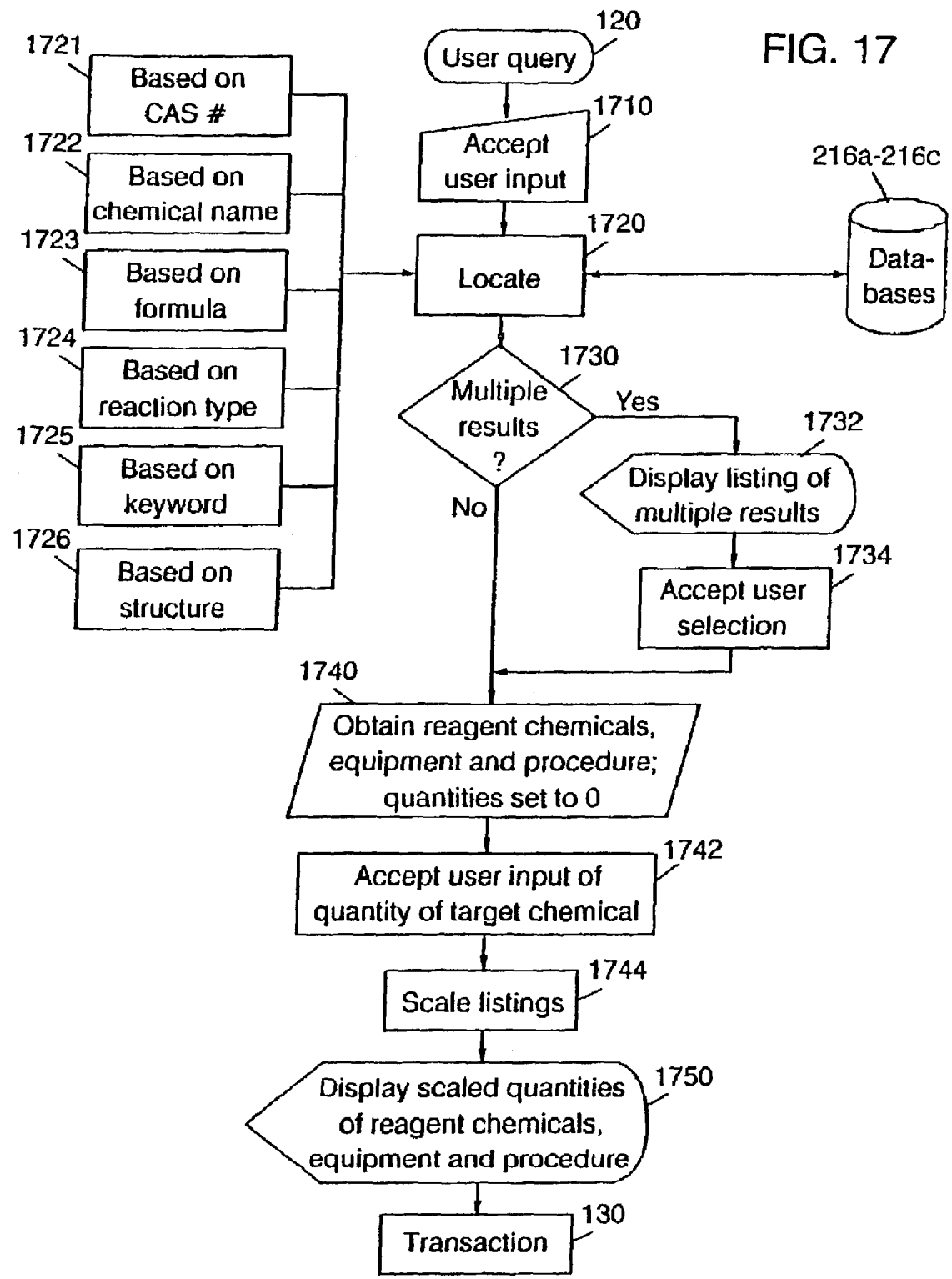
FIG. 17 is a flowchart of operations for performing user queries according to embodiments of the present invention.

Referring now to FIG. 17, operations for performing user queries (Block 120 of FIGS. 1A-1C and 1F) now will be described in detail. As shown at Block 1710, a user identification of a target chemical is accepted. At Block 1720, a listing of reagent chemicals that are used to synthesize the target chemical, a listing of equipment that is used to synthesize the target chemical and a listing of the procedure that is used to synthesize the target chemical by reacting the reagent chemicals in the equipment according to the procedure, is located and displayed.

As shown at Blocks 1721-1726, many different query techniques may be used to identify a target chemical. In particular, a user identification of a target chemical may be obtained based on CAS number (Block 1721), chemical name (Block 1722), chemical formula (Block 1723) or chemical structure (Block 1726). Moreover, at Block 1724, the user identification of a reaction type is accepted and a listing of target chemicals that are synthesized using the reaction type is displayed. Then, a user selection of a target chemical from the listing of target chemicals that are synthesized using the reaction type is accepted. Finally, at Block 1725, user identification of a keyword may be accepted and a listing of target chemicals that are synthesized using the keyword may be displayed. A user selection of a target chemical from a listing of target chemicals that are synthesized using the keyword then is obtained. Other query techniques also may be used.

Based on the input at Blocks 1721-1726, the locate operations of Block 1720 perform database searches of the databases 216a-216c of FIG. 2, for example via the database server 215.

Figure 18:

Additional details of the operations of Blocks 1710 and 1720-1726 now will be provided. FIG. 18 illustrates an example of a user display that may be displayed at a customer site 218 to accept user input at Block 1710. As shown in FIG. 18, the CAS number, chemical formula or compound name may be entered at field 1810. Upon entering data at field 1810 and activating the Locate! button, the processing of Block 1720 can first determine whether a valid CAS number is present. If yes, then a search of the databases 216a-216c may be performed based on the CAS field in Table 1. If a valid CAS number is not present, then a search may be performed on the name and formula fields of Table 1.

A user also may input a chemical structure (Block 1726) using conventional chemical drawing and/or other drawing programs. The chemical structure then may be searched by converting the chemical structure into an alphanumeric string that represents the chemical structure, for example using conventional conversion tools. For example, the SMILES tool kit, marketed by Daylight Chemical Information Systems, Inc., may be used to convert the chemical structure into an alphanumeric string using protocols that are described at www.daylight.com. In yet another alternative, an MDL tool, marketed by MDL Information Systems, Inc., may be used to convert the chemical structure into an alphanumeric string, as described at www.mdli.com. Other conversion tools may be used. A search then may be performed relative to the smiles and reagent smiles attributes of the chemical database 216a, as was described in Table 1.

Still referring to FIG. 18, alternatively, if the user does not know exactly what the user is searching for, an entry may be made at field 1820 based on reaction type (Block 1724) or any other keyword (Block 1725), and the Locate Action Type button can be pressed. A search then is performed on the info, name, equivalent, other_names or other fields of the chemical database 216a, to attempt to find a match.

Referring now to Block 1730 of FIG. 17, a search based on CAS number (Block 1721), chemical name (Block 1722) or formula (Block 1723) may produce a single result of a match or multiple results. If a single result is produced, then the single result is displayed at Block 1740. However, a search based on reaction type (Block 1724) or keyword (Block 1725) generally will provide multiple matches at Block 1730. If multiple results are present at Block 1730, a listing of the multiple results is displayed at Block 1732. An example of a display of multiple results is shown in FIG. 19 based on a search of the chemical name "bromo" in field 1810 of FIG. 18. A user selection of one of the matches from the list is then accepted at Block 1734, and the result is displayed at Block 1740.

When multiple results are found, a prioritized listing may be displayed, so that more likely desired results are displayed at the top of the listing. In particular, in response to a user input in field 1810 of FIG. 18, the name, other_names and info attributes of the chemical database 216a may be searched. The results may be displayed in a priority sequence as follows: exact matches in the name attribute; exact matches in the other_names attribute; partial matches in the name attribute; and, finally, partial matches in the other_names attribute. By prioritizing the display of results, the more likely user selections may be displayed at the top of the list in FIG. 19.

Figure 20A:
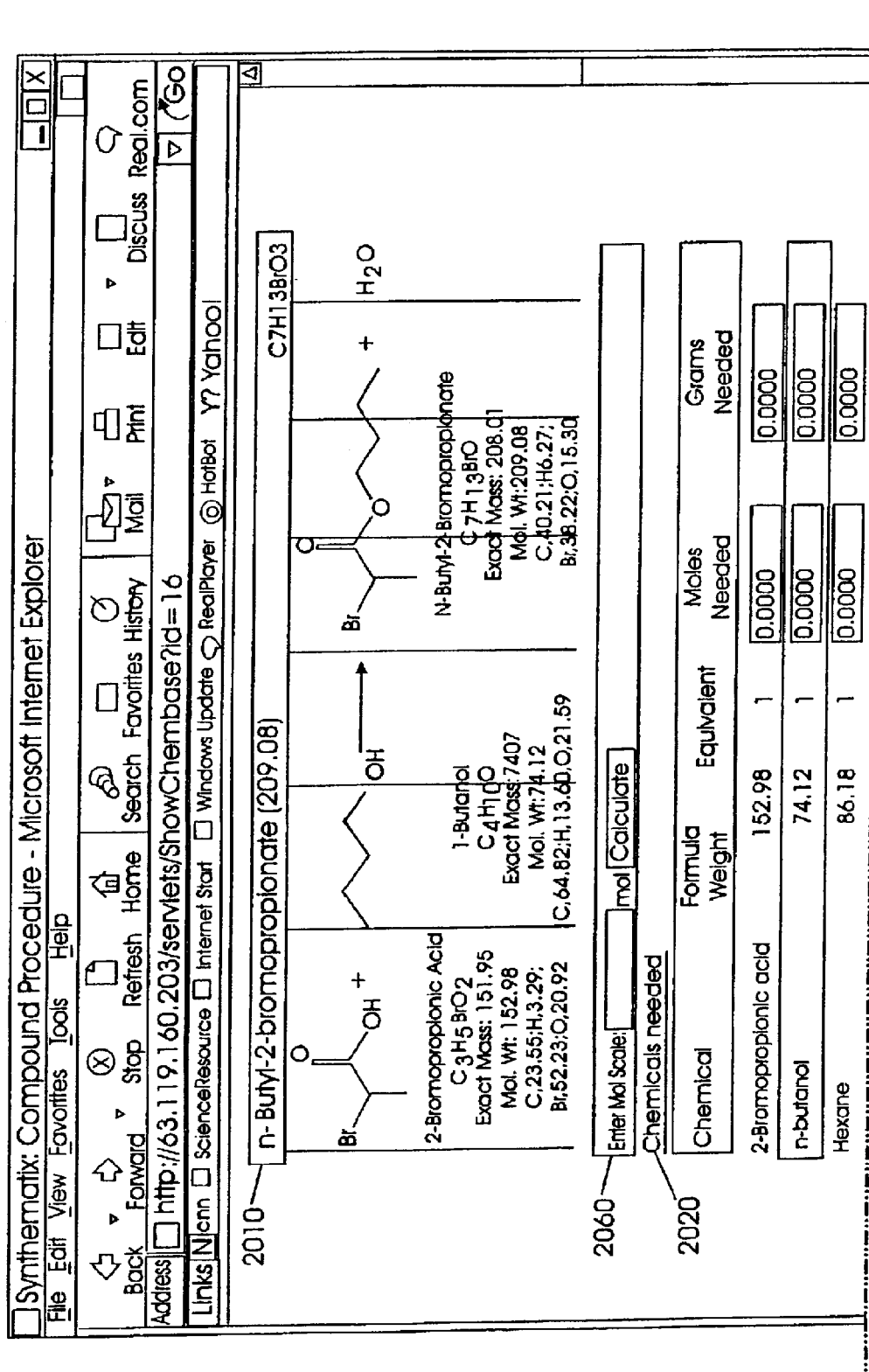
FIGS. 20 and 21 illustrate displays of listings of reagent chemicals, equipment and procedures according to embodiments of the present invention.

Referring now to Block 1740, a listing of the reagent chemicals, the corresponding equipment and the corresponding procedure is provided, for example as shown in FIG. 20. As shown in FIG. 20, the name of the chemical is displayed at 2010, the reagents are displayed at 2020, the equipment is displayed at 2030, the procedure is displayed at 2040, and the reference that was used to derive the procedure is displayed at 2050.

The operations of FIG. 17 that were described above can facilitate both forward searching and backward searching for target chemicals. In forward searching, a search can be made as to which chemical reactions include a chemical as a reagent. Thus, user identification of a chemical is accepted, and a listing of procedures that use the chemical as a reagent chemical is displayed. A user selection of the procedure from the listing of procedures that use the chemical as a reagent chemical then is accepted. In forward searching, the chemicals attribute of the chemical database 216a of Table 1 may be searched.

In contrast, in backward searching, a search may be made as to how a target chemical may be synthesized. As was described above, in response to selection of a target chemical, a listing of procedures can be displayed that can be used to synthesize the target chemical. A user selection of the procedure is then accepted. In backward searching, the name attribute of the chemical database 216a of Table 1 may be searched.

Figure 21A:
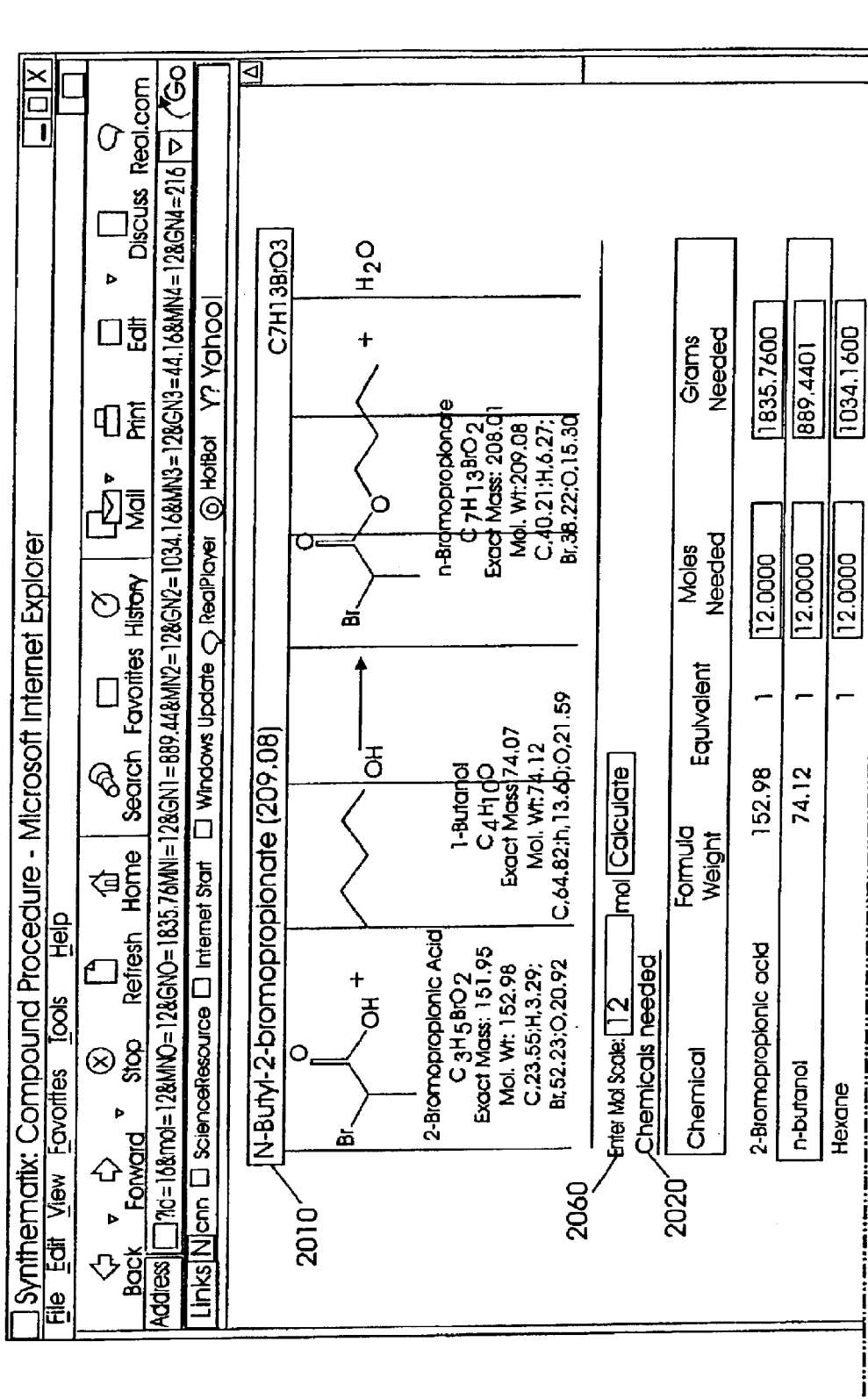

Referring again to FIG. 20, the initial display of FIG. 20 may default to 0 grams or 0 moles of the reagent chemicals and 0 quantities of the equipment. In order to allow synthesis of a desired amount of the target chemical, the user input of a number of moles of the chemical may be input at field 2060, as shown at Block 1742. At Block 1744, the listings of the reagent chemicals and equipment are scaled, so as to synthesize the desired quantity of the target chemical. Then, at Block 1750, a scaled listing of reagent chemicals that are used to synthesize the desired quantity of the target chemical, a listing of equipment that is used to synthesize the desired quantity of the target chemical and a listing of a procedure that is used to synthesize the desired quantity of the target chemical is displayed. FIG. 21 illustrates a display procedure that includes the desired quantities of reagents and equipment. Referring again to FIG. 17, if a customer desires to electronically order the target chemical, reagent chemicals and/or the equipment, the customer proceeds to transaction (Block 130 of FIGS. 1A, 1C-1D and 1G), as will be described in detail below.

Figure 22:
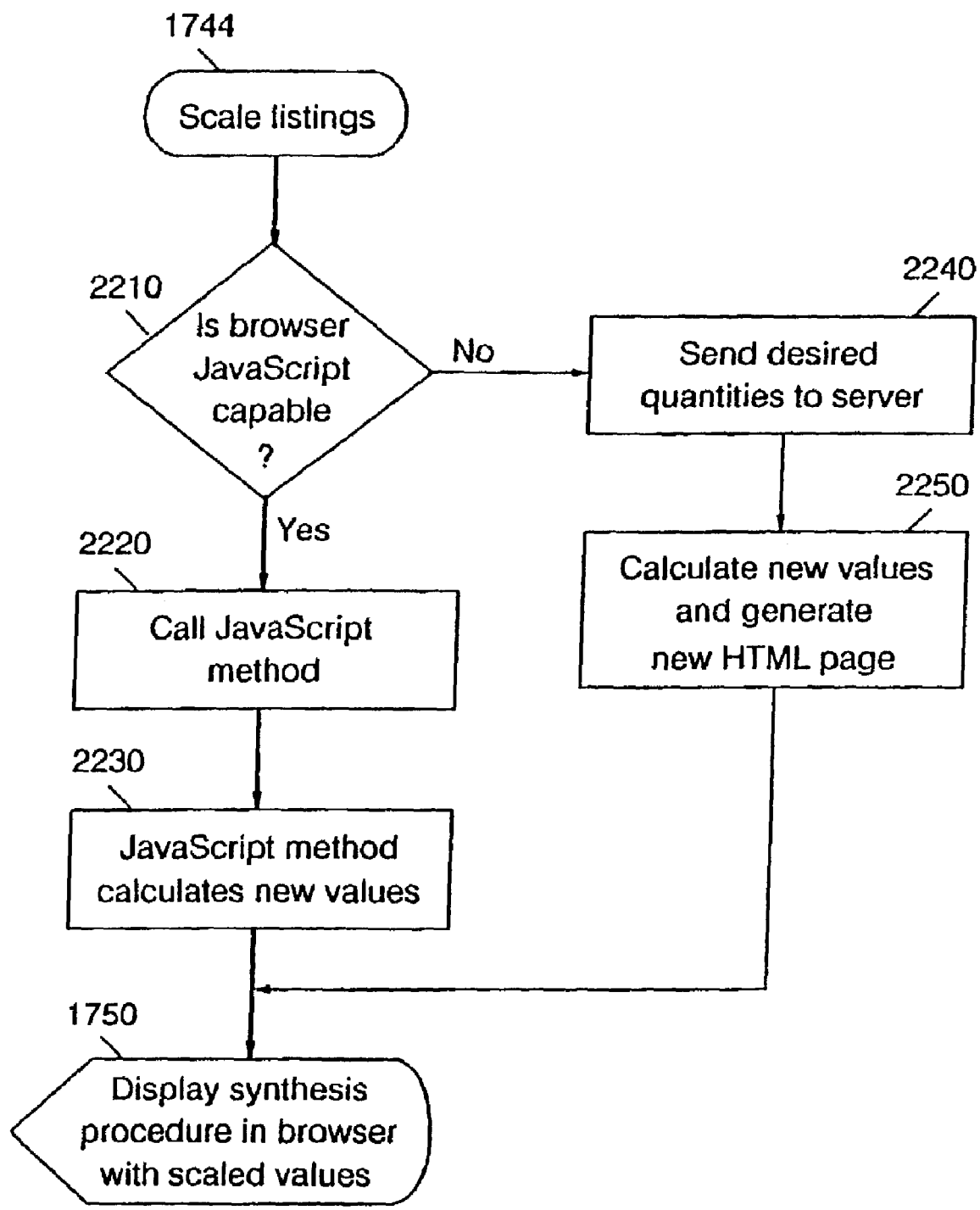
FIG. 22 is a flowchart of scaling of listings according to embodiments of the present invention.

Referring now to FIG. 22, additional details of scaling the listings (Block 1744 of FIG. 17) now will be described. As shown in FIG. 22, the desired quantities may be calculated at the customer site 218 using a browser and/or at the server Web site 212. In particular, as shown at Block 2210, if browser side scripting is supported, for example if the browser is JavaScript-capable, then at Block 2220, the JavaScript method that is specified in the onClick attribute of the Submit button is called. At Block 2230, this JavaScript method calculates the new values and displays them on the Web page at Block 1750. It can return false to stop further processing. It also can provide the values to the server Web site 212 as well.

Returning to Block 2210, if browser side scripting is not supported, then the desired quantity is sent to the server Web site 212 at Block 2240, for example by calling the Uniform Resource Locator (URL) specified in the action attribute of the form page. The server Web site 212 then calculates the new values at Block 2250 and generates a new HTML page at Block 2250, which then is sent back to the customer site 218 for display at Block 1750.

In a specific embodiment, a customer site (client side) JavaScript implementation of the scaler can use the onClick attribute of the HTML tag <input> when the tag also has the attribute type="submit". An example snippet is as follows:

```
<form action = http://someplace.com/formhandler>
<input type = "submit" onClick = "return doSomething( )">
</form>.
```

Prior to Netscape Navigator 2.0, the onClick attribute was undefined, so that clicking the Submit button would execute the form action. However, Netscape Navigator 2.0 can cause JavaScript code to be executed prior to calling the action URL defined in the <form>'s action attribute. In Navigator 3.0, the onClick attribute was evaluated for a Boolean (true/false) value. If the value was false, the action URL was not called. Thus, the behavior introduced in Netscape Navigator 3.0 can allow client side only calculation of the scaler value. The calculation can be defined in JavaScript, which is embedded in the HTML page, and referred to this calculation in the onClick attribute.

Figure 23:
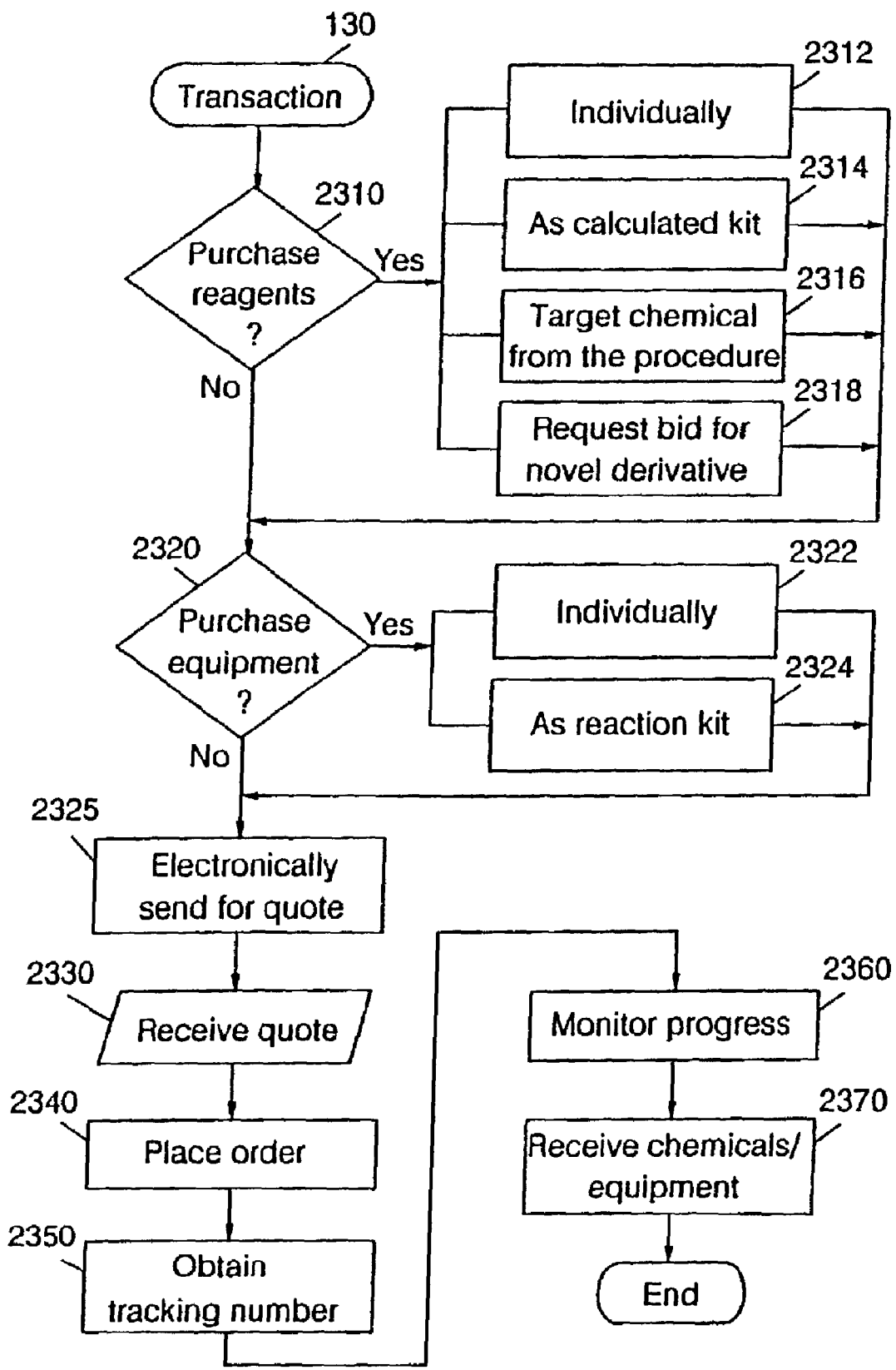
FIG. 23 is a flowchart of transactions according to embodiments of the present invention.

Referring now to FIG. 23, details of performing a transaction (Block 130 of FIGS. 1A, 1C-1D and 1G) now will be described in detail. In general, user input to order reagent chemicals and/or equipment is accepted and the reagent chemicals and/or equipment are electronically ordered. More specifically, as shown in Block 2310, a user input is accepted to purchase reagents. The reagents may be purchased individually (Block 2312) or as a calculated kit (Block 2314). Moreover, the target chemical itself may be purchased directly from a supplier at Block 2316. Finally, if a target chemical is not found in the database, but a derivative thereof is found, a request may be sent to bid on the novel derivative at Block 2318.

Equipment also may be purchased at Block 2320. The equipment may be purchased individually at Block 2322, or as a reaction kit at Block 2324. The supplier database 216c may be used to electronically request a quote at Block 2325 to the supplier sites 222 over the computer network 220 of FIG. 2. A quote then is received at Block 2330, and, if acceptable, an order is placed at Block 2340. The order may be placed by communication over the computer network 220 to the supplier sites 222. A tracking number may be obtained at Block 2350, and the progress of the order may be monitored at Block 2360, for example by providing a private Web page that is generated to match the tracking number of Block 2350. The chemicals and/or equipment then are received at Block 2370.

Other Embodiments

Figure 24:
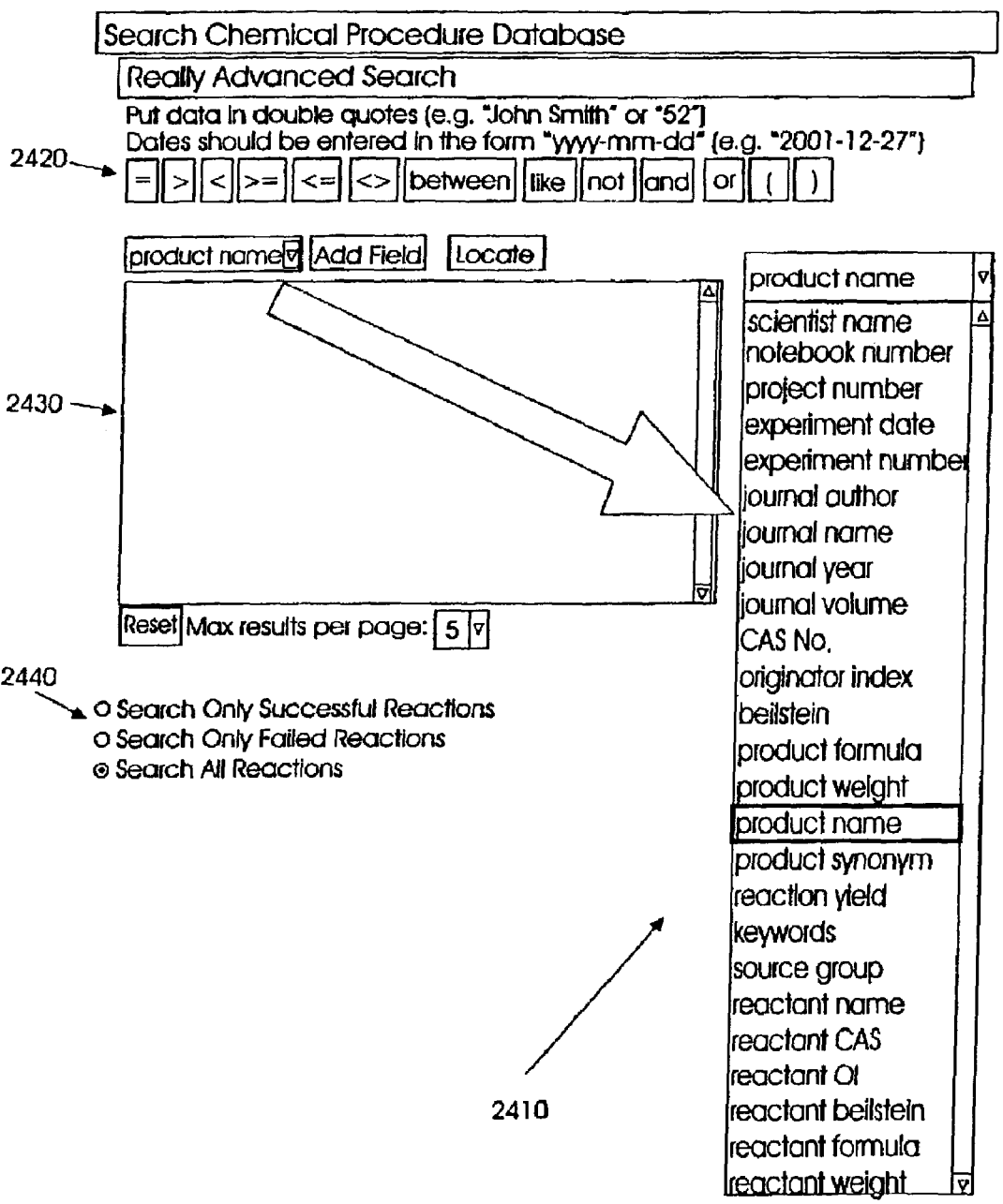
FIG. 24 illustrates a display that may be used for Boolean searching according to embodiments of the present invention.

As was described in FIG. 17, embodiments of the present invention may obtain a user identification of a target chemical based on CAS number, chemical name, formula, reaction type, keyword and/or chemical structure. FIG. 18 illustrated an embodiment of a user display that may be used to perform user queries. FIG. 24 illustrates another embodiment of a user display that may be used to accept a user identification of a target chemical by chemical formula, chemical structure, chemical substructure, chemical compound name, CAS number and/or successful/failed reaction according to embodiments of the present invention.

As shown in FIG. 24, a listing 2410 of query fields may be selected from a pull-down menu and a listing of Boolean operators 2420 may be used to build a Boolean query in a Boolean query window 2430. The listing of query fields 2410 may be modified by a user.

Moreover, as shown by selection area 2440, queries also may be performed based only on successful reactions (procedures), based only on failed reactions or based on all reactions. Failed reactions may be identified using the yield field of Table 1 where yield=0. It may be desirable to search only successful reactions in order to increase the likelihood that a selected procedure will provide the desired target chemical. It may be desirable to search only failed reactions in order to identify where prior researchers have been unable to synthesize a target chemical, to identify new areas for possible exploration.

Figure 25:
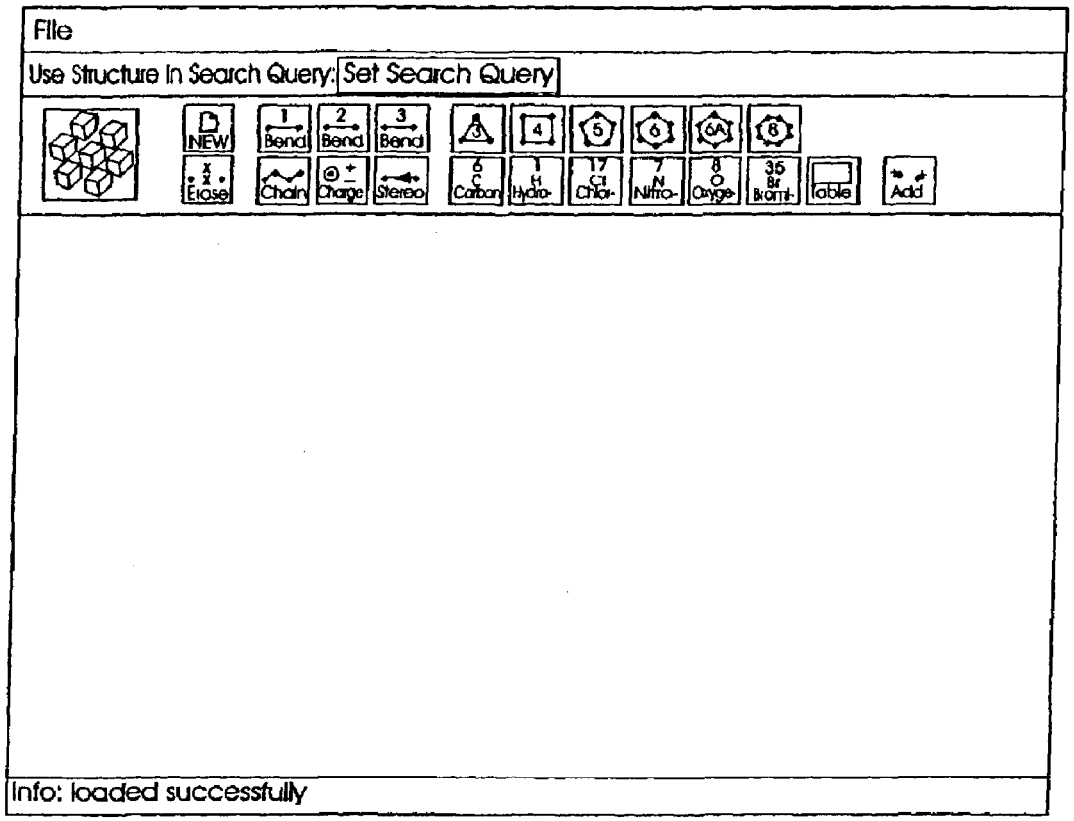
FIG. 25 illustrates a display that may be used for structure/substructure searching according to embodiments of the present invention.

Moreover, according to other embodiments, structures and/or substructures may be used as a search query, alone, in combination with the Boolean search query builder of FIG. 24 and/or in combination with the query display of FIG. 18. In particular, as shown in FIG. 25, a user display for a structure/substructure query can allow the structure/substructure to be drawn and searches of the chemical database 216a to be performed using this structure/substructure. Conventional chemical drawing programs also may be used for the structure/substructure search.

The structure/substructure query display may be based upon a drawing tool that is designed to be useful on a Personal Digital Assistant (PDA) device. It may be particularly useful to use a stylus to click once to obtain a structure. Moreover, highlighting of bonds may facilitate drawing and/or data entry using these types of devices. When used with a PDA, the drawing tool can save drawings at the server 212 for sharing and/or real time on-line collaboration (analogous to an online chemical white board) and/or to save locally.

Figure 26:
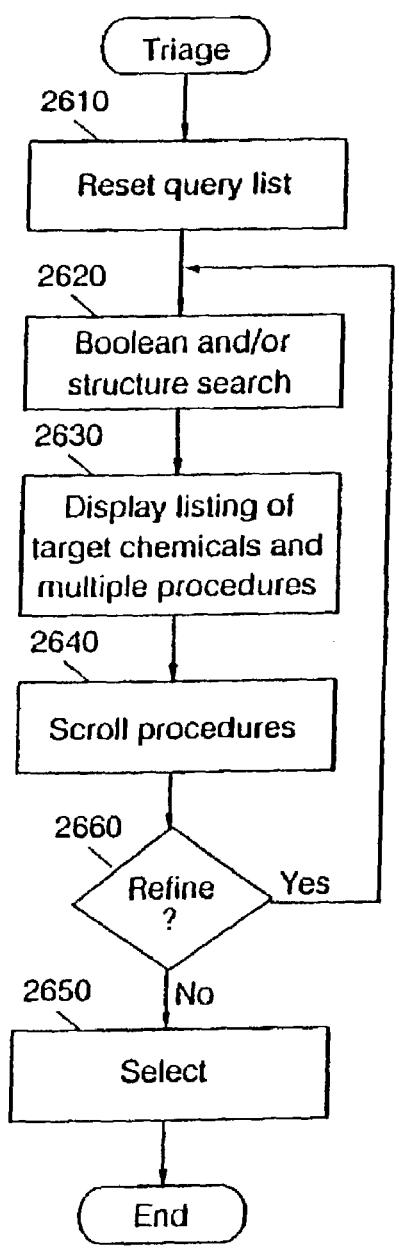
FIG. 26 is a flowchart of operations that may be used to perform reaction triage according to embodiments of the present invention.

FIGS. 26 and 27 illustrate operations for performing a "reaction triage" to allow rapid screening of large numbers of listings of target chemicals and/or procedures. In particular, these embodiments of the invention can display a list of target chemicals and an indication that a plurality of procedures may be used to synthesize at least one of the target chemicals. A user selection is accepted to scroll a plurality of procedures that may be used to synthesize at least one of the target chemicals. Finally, the user selection of a procedure from a plurality of procedures is accepted.

FIG. 26 is a flowchart illustrating operations for reaction triage according to some embodiments of the present invention. These operations may be used instead of and/or in addition to the locate operations 1720 of FIG. 17.

Referring now to FIG. 26, operations begin at Block 2610 by resetting a query list, if necessary. A Boolean and/or structure search is performed at Block 2620, for example, as was already described above in connection with FIGS. 24 and 25. Then, at Block 2630, a listing of target chemicals and multiple procedures is displayed. FIG. 27 is an example of a user display of a listing 2710 of target chemicals and an indication 2720 that a plurality of procedures (protocols) may be used to synthesize the associated target chemical. In FIG. 27, the number of procedures that may be used to synthesize the target chemical is indicated at 2720. However, other indications may be used. For example, an asterisk may be used to indicate that multiple procedures are available.

Referring again to FIG. 26, at Block 2640 a user selection is accepted to scroll the plurality of procedures that may be used to synthesize an associated target chemical. In particular, a user may click on a target chemical in the listing 2710 and then may click on the previous/next buttons 2730 to scroll through the plurality of procedures. As shown at Block 2660, clicking on the list of target chemicals 2710 and scrolling using the previous/next buttons 2730 may be repeatedly performed in order to refine the identification of a target chemical and a procedure until, at Block 2650, a final user selection of a procedure that can be used to synthesize a target chemical is accepted. The final selection of Block 2650 may take place for example, by selecting the target chemical in the product area 2740 of FIG. 27. Selecting the target chemical in the product area 2740 of FIG. 27 can move processing to the user display of FIG. 20. Moreover, the triage user display of FIG. 27 and the selections within it then can be required, for example, using the searching of FIGS. 24 and 25.

It also will be understood that displays of FIG. 20 and/or other user displays that are described herein can be printed for archival purposes. Moreover, embodiments of the invention can add time stamping, user stamping, signature and/or witness lines to the print-out for use in lab notebooks for archival and/or intellectual property protection purposes.

Embodiments of the invention that were described above, for example in connection with FIG. 20, can display the chemical reaction that may be used to synthesize the target chemical from the reagent chemicals as shown, for example, at 2010. Other embodiments of the invention will now be described that can display a reaction flowchart that can provide an overall view of a multi-step reaction to allow searching on connected reactions and/or related syntheses. Thus, according to these embodiments of the invention, a flowchart may be displayed that graphically illustrates first reagent chemicals that are used to synthesize the target chemical, second reagent chemicals that used to synthesize the first reagent chemicals, third reagent chemicals that are used to synthesize the second reagent chemicals, etc. The flowchart also can illustrate procedures that are used to synthesize the second reagent chemicals from the third reagent chemicals, the first reagent chemicals from the second reagent chemicals, the target chemical from the first reagent chemicals, etc. A reaction view therefore may be displayed that proceeds backwards from the target chemical to basic elements and/or proceeds forward from the target chemical to other reactions that use the target chemical.

Figure 28:
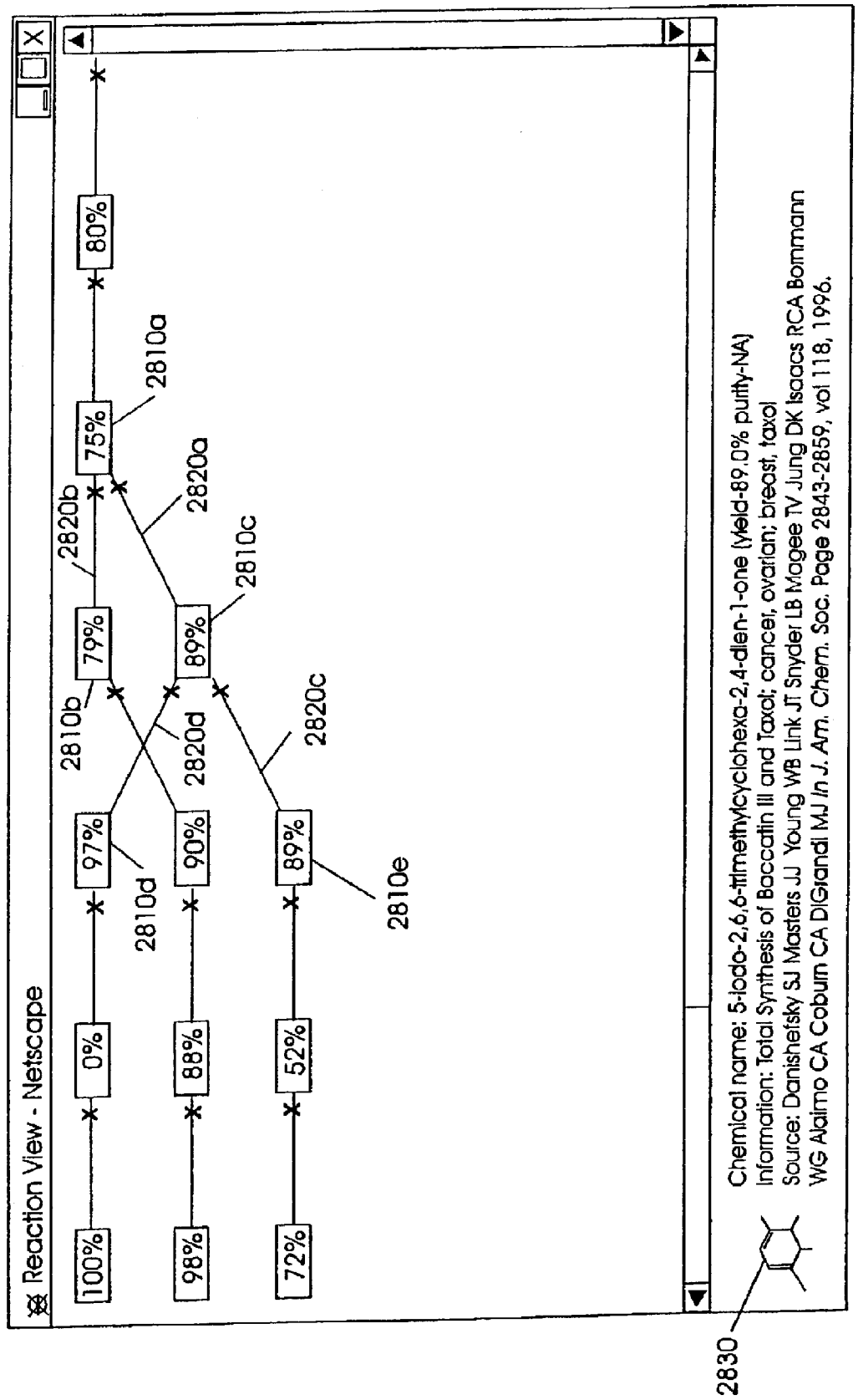
FIG. 28 illustrates a display of a reaction view flowchart according to embodiments of the present invention.

FIG. 28 illustrates an embodiment of a user display for a reaction view flowchart. This example illustrates a sequence of steps for the synthesis of Taxol. User displays of FIG. 28 may be accessed by selecting a "reaction view" button, for example, in FIG. 20.

As shown in FIG. 28, the flowchart comprises a plurality of nodes 2810a-2810e . . . that are linked by branches 2820a-2820d . . . . In some embodiments, the nodes correspond to chemicals and the branches correspond to procedures. Thus, in FIG. 28, the node 2810a can correspond to the target chemical, the nodes 2810b and 2810c can correspond to first reagent chemicals, the nodes 2810d and 2810e can correspond to a second reagent chemical, etc. The branches 2820a and 2820b correspond to procedures that are used to synthesize the target chemical 2810a. In other embodiments, the branches can correspond to the target chemical, the first reagent chemicals, the second reagent chemicals, the third reagent chemicals, etc., and the nodes can correspond to the procedures that are used to synthesize the target chemical, the first reagent chemicals, the second reagent chemicals, the third reagent chemicals, etc.

In FIG. 28, the numbers in the blocks indicate yields. A user can mouse over a node 2810 to display a drawing of the chemical and/or other useful information at window 2830. Selecting the window 2830 can move the user directly to a user display of FIG. 20.

In summary, reaction view flowcharts according to embodiments of the invention, such as are illustrated in FIG. 28, may provide flowcharts of nodes and branches wherein the nodes correspond to chemicals and the branches correspond to procedures or the branches correspond to chemicals and the nodes correspond to procedures. These multi-step reaction views can be used to find work-arounds around various portions of a multi-step reaction and/or connections that can be used to bypass various steps. The multi-step reaction view may be built by systems, methods and/or computer program products according to embodiments of the invention, by repeatedly looping over the chemical database 216a using the first pointers of Table 1 until no further records are pointed to.

Chemical data thereby can be visualized by moving forward and/or backward on a reaction tree. A user can navigate forward to see what the reaction product may be used for, and backward to see how the reagents may be made. By obtaining a high-level view of where a reaction lies in space relative to other linked reactions, users can visualize the reaction pathways and the connectivity of reactions.

Figure 29:
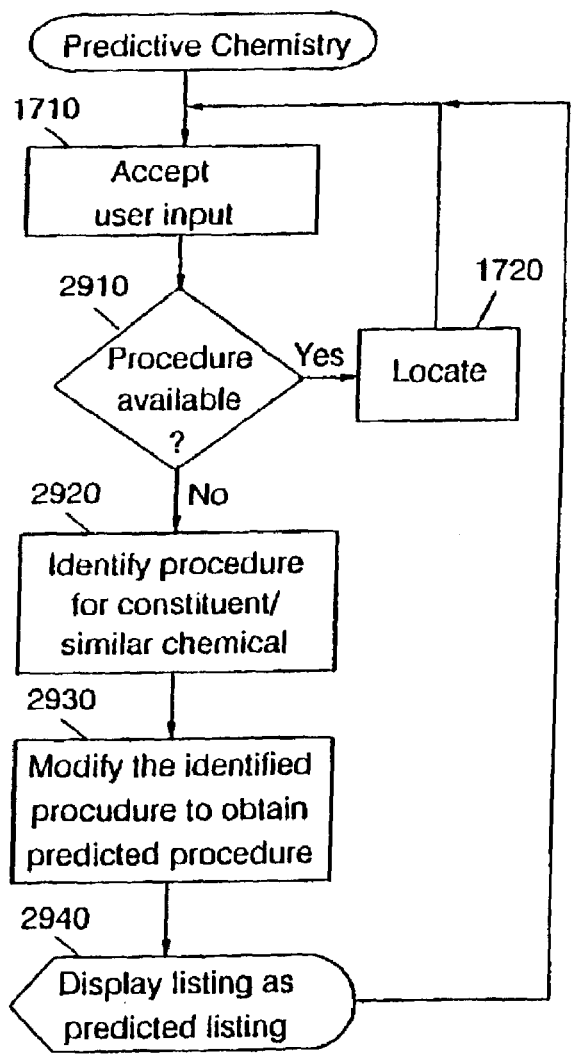
FIG. 29 is a flowchart of operations that may be used to perform predictive chemistry according to embodiments of the present invention.

Referring now to FIGS. 29-31, predictive or guide chemistry according to embodiments of the present invention now will be described. Predictive chemistry can provide systems, methods and/or computer program products for searching for similar reactions while allowing users to plan new reactions based on empirical data in the chemical database 216a. Reactions may be mapped based on similar transformations and/or other historical data. Thus, predictive chemistry may be used in the up-front planning portion of a synthetic procedure by a scientist. This can allow greater "synthetic memory" than may be currently possible.

Referring now to FIG. 29, at Block 1710 a user input of a target chemical is accepted, using any of the techniques that were described above. A determination is then made at Block 2910 as to whether the procedures for synthesizing the target chemical are available in the chemical database 216a. If yes, a locate operation 1720 is performed. However, if an exact match is not found at Block 2910, indicating that a procedure is not available for synthesizing the target chemical, then at Block 2920 a procedure that may be used to synthesize a constituent part of the target chemical and/or a chemical that is similar to the target chemical is identified. At Block 2930, the procedure that may be used to synthesize the constituent part of the target chemical and/or the chemical that is similar to the target chemical is modified to obtain a predicted procedure that may be used to synthesize the target chemical. At Block 2940 a listing of reagent chemicals that may be used to synthesize the target chemical, a listing of equipment that may be used to synthesize the target chemical and a listing of the predicted procedure that may be used to synthesize the target chemical by reacting the reagent chemicals in the equipment according to the predicted procedure, is displayed.

Figure 30A:
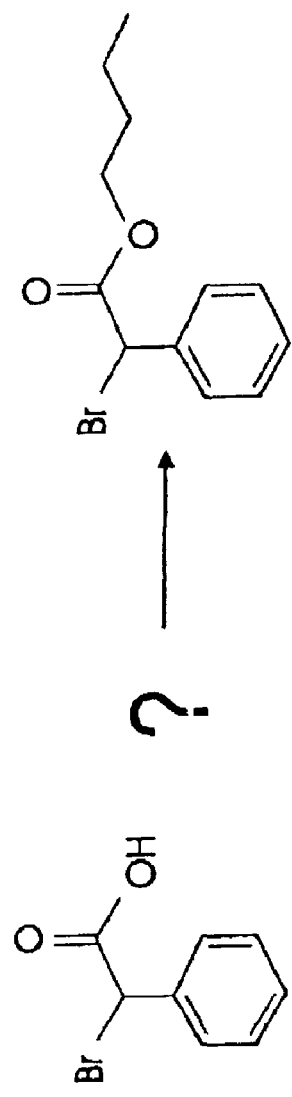
Figure 30B:
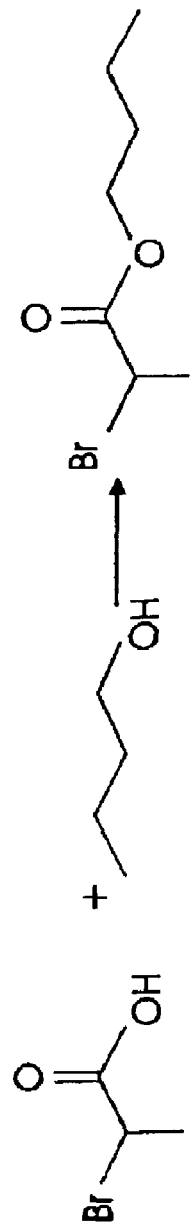
Figure 30C:
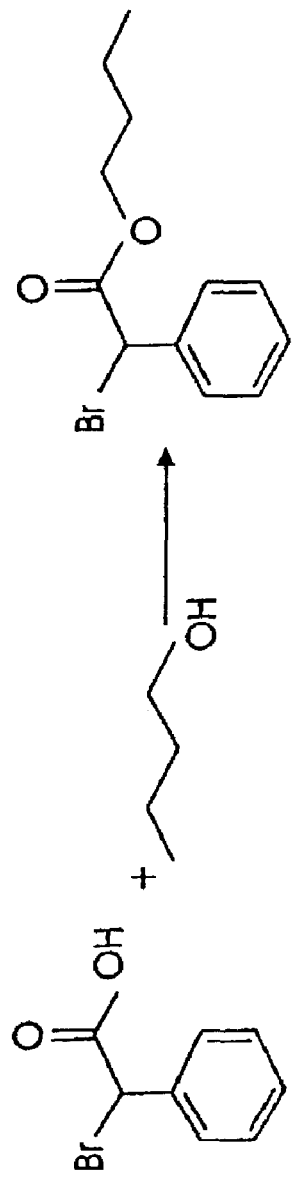

FIGS. 30A-30C illustrate an example of the use of predictive chemistry according to some embodiments of the present invention. As shown in FIG. 30A, an input may be provided by a user (Block 1710 of FIG. 29), for example, by drawing a potential reaction by which a known reagent chemical and an unknown reagent chemical may be used to synthesize a target chemical. If no match for the target chemical of FIG. 30A is found at Block 2910 of FIG. 29, then at Block 2920 of FIG. 29, searches may be made in background for similar structural and/or reactivity factors in the chemical database 216a for reactions that have been performed before. Moreover, if exact matches were found at Block 2910, the user also may be asked whether the user wishes to view other reactions as well.

As shown in FIG. 30B, to perform a similar reaction match, embodiments of the invention can use the same substructure system that is used in other searches. Thus, FIG. 30B illustrates a known procedure for synthesizing a target chemical having a structure that is similar to a substructure of the target chemical of FIG. 30A. FIG. 31 provides an example of how a query of reactants and/or products can identify procedures for constituent and/or similar chemicals. Finally, as shown in FIG. 30e, a functional group search and replacement may be made using known intermediates and suggested procedures based upon the data that is stored in the chemical database 216a to thereby modify the identified procedure to obtain a predicted procedure (Block 2930 of FIG. 29).

Thus, these embodiments of the invention can use the experimental procedure and the same reactant ratios as the empirical data. The drawing structures then can be copied over into the empirical template and the amounts can be recalculated. A new reaction is then suggested as a trial based upon the previous knowledge. The data stored in the chemical database 216a therefore may provide an institutional memory that can be used for predictive or guide chemistry to guide scientists to predict parameters for chemical synthesis of a target chemical where no such parameters exist in the chemical database 216a.

Additional Embodiments

Additional embodiments of predictive chemistry that were generally described in connection with FIGS. 29-31 will now be described. Predictive chemistry may also be referred to herein as a reaction template. A reaction template may be used when a user finds a reaction the user would like to repeat, modify and/or improve upon. In order to use a reaction template, a reaction first may be identified. In some embodiments, an identification number of a known reaction may be provided and used as a template. When a valid identification number is entered, the reaction matching that number can open in a reaction editor form. In this form, certain information may be nullified, such as the yield impurity of the product, the summary information, the notebook reference and the attachments associated with the reaction. For database differentiation, when the reaction is opened as a template, the identification associated with that reaction, a success or abandoned flag and a verified tag may be nullified so that, in essence, a new reaction is created that happens to have most of the synthetic information with it.

Reactions also may be opened as a template by running a search as was described above. The search results can then be used as a template. Reaction templates also may be created using a reaction view flowchart, as was already described in FIG. 28. In a reaction template mode, any node of the flowchart of FIG. 28 may be used to open a reaction template. Accordingly, a reaction template may be used when the target chemical is not one of the plurality of target chemicals in the database. However, a list of reagent chemicals that are predicted to synthesize the target chemical, a listing of equipment that is predicted to be used to synthesize the target chemical, and a listing of a procedure that is predicted to be used to synthesize the target chemical by reacting the predicted reagent chemicals in the predicted equipment according to the predicted procedure may be displayed.

Figure 41:
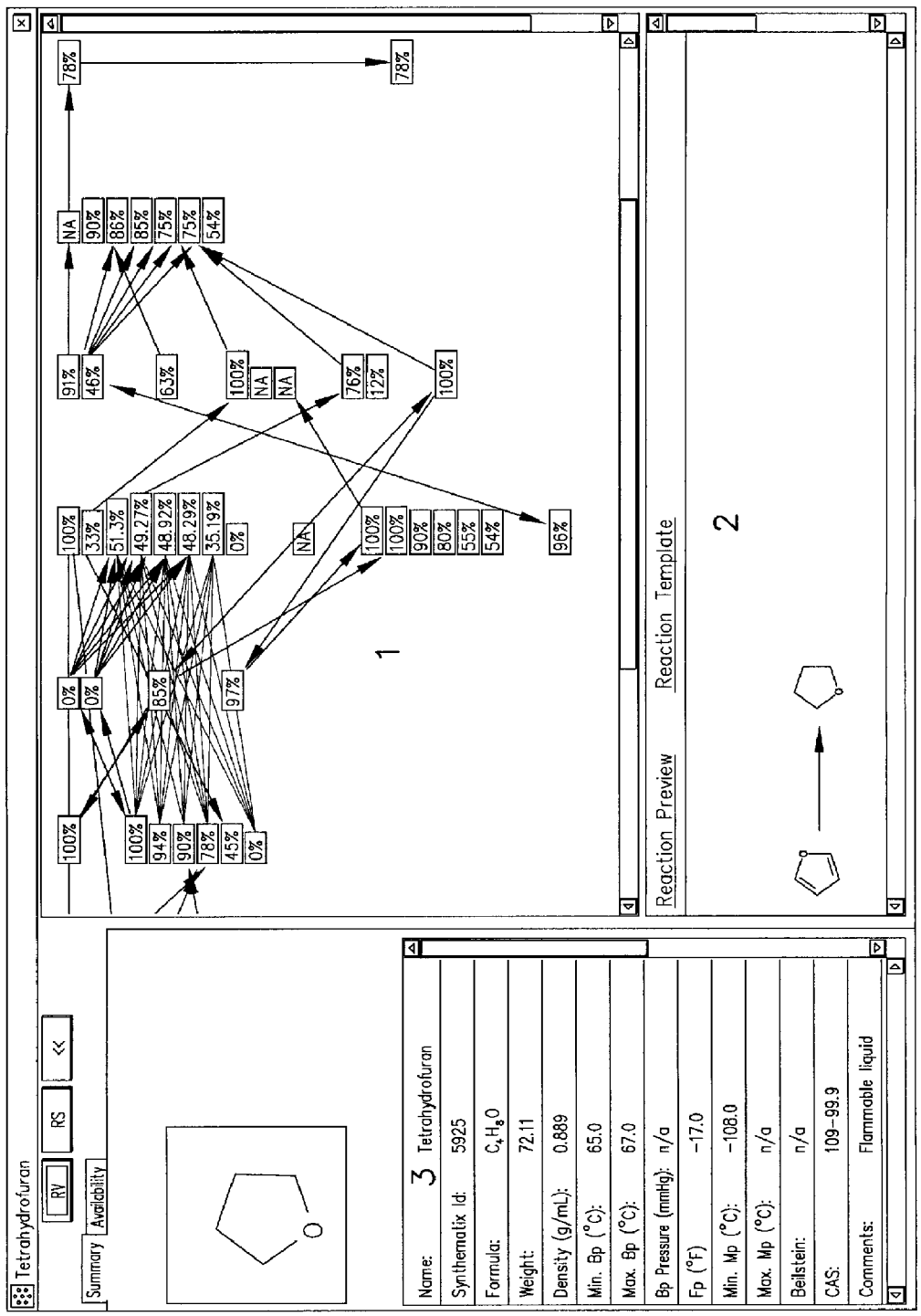
FIGS. 41-45 illustrate user displays that may be used to display target chemicals, reagent chemicals and additional chemicals in which the target chemical is a reagent chemical according to embodiments of the present invention.

Other embodiments of reaction view flowcharts, also referred to herein as a "Retro-Synthetic Tree", now will be described. In some embodiments, the Retro-Synthetic Tree user interface includes three main panels as shown in FIG. 41. The large upper right hand panel, labeled 1, shows the graph or flowchart created from the database. The panel located on the lower right hand side, labeled 2, provides basic information about any of the associated reactions and allows the user to jump to the reactions, for example via a Web link. The panel located on the left hand side, labeled 3, shows information about a substance that matches the property information stored in the database. All of these panels may be adjustable by clicking on the frames and dragging them to make the panels larger or smaller and/or to move their relative locations as desired.

When the Retro-Synthetic Tree is launched, the database is searched to find all the linked procedures used in making the precursors and reagents for the product of the target chemical. The left hand panel can always contain information about the product for which the graph was generated. If all of this information is not visible, the user can use the scroll on the right hand side of the panel to navigate through the information.

As also shown in FIG. 41, a graph is generated with nodes and lines connecting them. Each node may be a discrete reaction that can have any number of products and reactants associated with it. The number in each node represents the yield of the product in the reaction represented by that node. If there is more than one product associated with that reaction, both yields are shown with a comma separating the two. If a yield is not available, the abbreviation N/A is shown, to indicate that the information is not available.

A color coding scheme also may be used to differentiate the nodes in the graph or flowchart for ease of use. For example, a red box node can represent the product of the reactions that the graph originated from. If a substance has more than one procedure in which it is created, then the nodes are grouped together and may be shown in green. Nodes may be shown in white to identify discrete products and reactions. Nodes are movable so that the user can view the relationships more easily by reorganizing their groupings. Lines, such as green lines, can connect nodes that represent different reactions that have the same product. Arrows, such as blue arrows, can show that there is a synthetic path between the two products at either end.

The information provided on the lower right hand side of the display provides a diagram of the reaction scheme, the yield of each product, a list of the reagents used in the reaction that are not depicted in the reaction scheme, and/or the journal and/or notebook reference. To view all of this information, the user can use the scroll bar located at the right hand side of the panel. As also shown in this panel, a reaction preview link can open the reaction so that all of the information can be viewed, printed and/or opened as a template. The reaction template option allows the user to scale and/or customize the reaction before running the reaction.

As was described in connection with FIG. 3, in some embodiments of the present invention, operations for data entry may be performed by users, such as runners and/or other users, in order to enter procedures into a database. Embodiments of the invention that were described in connection with FIG. 3 employed a user interface that was described in connection with FIGS. 4-14. According to other embodiments of the invention that now will be described, an icon-based user interface may be provided to allow creation of a new procedure. This icon-based user interface is referred to herein as a "reaction editor", and may be used instead of, or in addition to, data entry procedures of FIGS. 3-14 by any user including a runner. The reaction editor includes a plurality of icons that correspond to a plurality of operations that may be selectively used to generate a procedure that is used to synthesize the target chemical by reacting the corresponding reagent chemicals in the corresponding equipment according to the procedure. User entry of selected ones of the icons from the reaction editor is sequentially accepted to build the procedure. In some embodiments, the plurality of icons further correspond to at least one of flasks, atmospheres, time or temperature that may be selectively used to generate a procedure that is used to synthesize a target chemical. In other embodiments, the plurality of icons that correspond to a plurality of operations comprise icons for at least some of the following operations: add, mix, dissolve, degas evacuate, heat, cool, reflux, stir, shake, extract, wash, distill, dry, filter, recrystallize, concentrate, chromatograph, titrate, titurate and rotovap.

Figure 32:
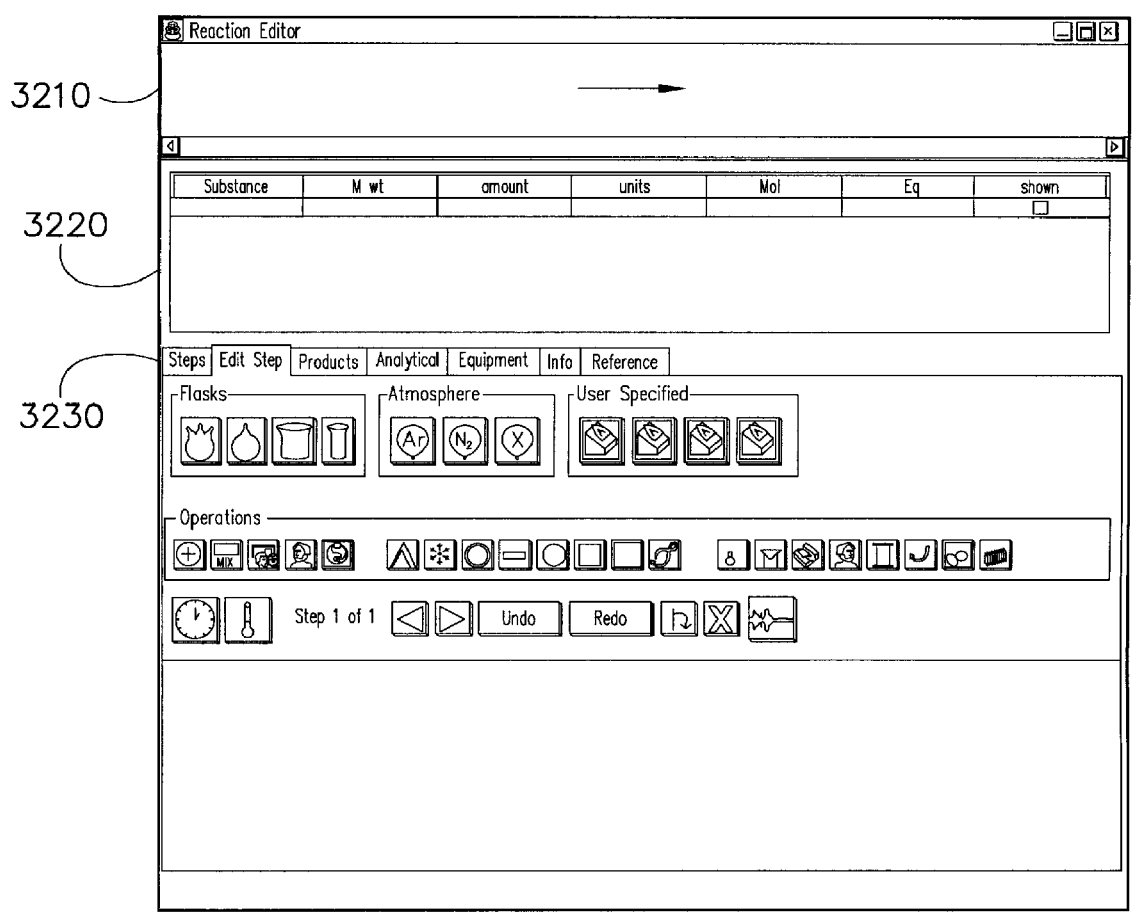
FIGS. 32-36 illustrate user displays that may be used for reaction planning according to embodiments of the present invention.

FIG. 32 illustrates an icon-based user display that may be used for reaction planning to create a new procedure according to some embodiments of the present invention. The overall layout of the user display of FIG. 32 can mirror the layout of the conventional lab notebook, to allow ease of navigation. As shown in FIG. 32, the user display can include a reaction editor portion 3210 in which the reaction is entered, a listing of substances at 3220, and a plurality of tabs 3230 that allow a user to generate one or more steps and to edit the steps to specify products, equipment, references and other parameters. These areas of the user display now will be described in detail.

Figure 33:
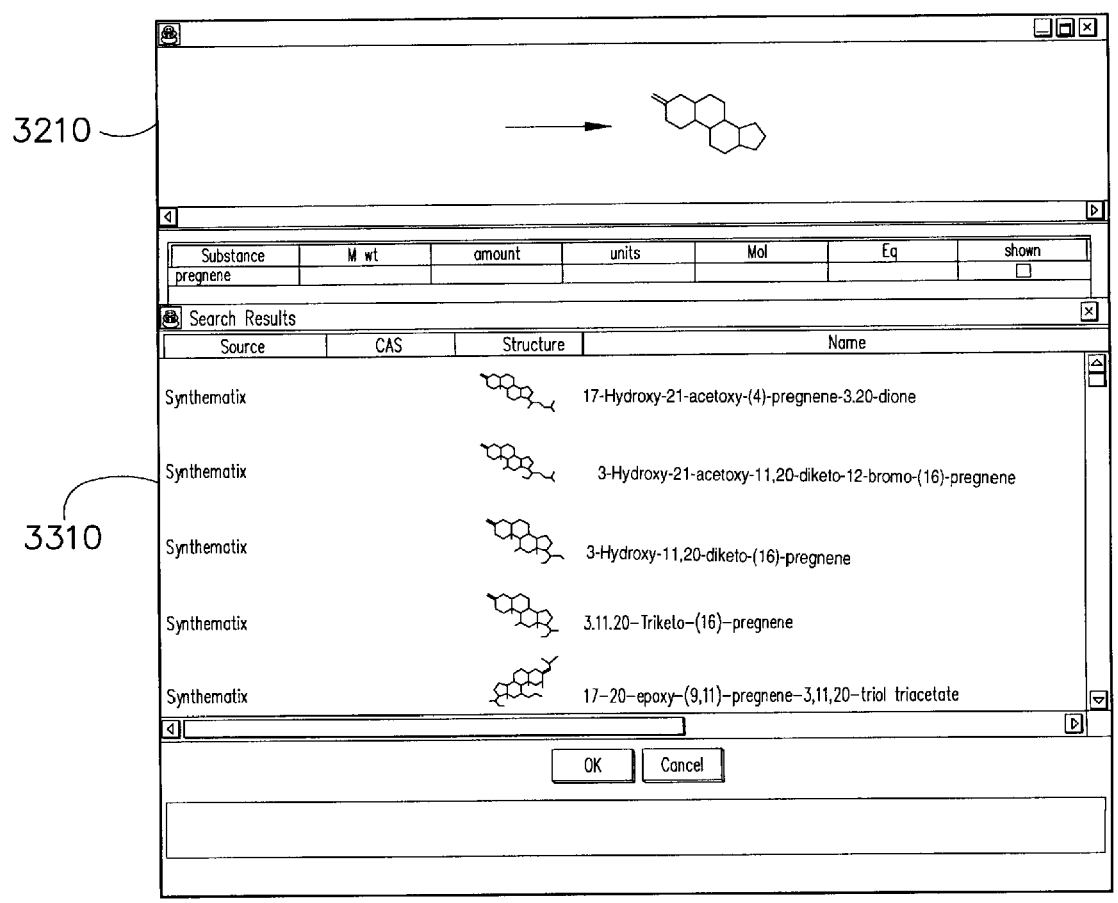

Referring now to FIG. 33, reagents may be drawn in the reaction editor 3210 by drawing and/or by lookup. In drawing, standard chemical drawing software and/or other drawing software may be used, as was already described. When performing a lookup, a search may be performed, as was already described, and the reagent may be selected from a list of search results, as shown in window 3310. The entry of the reagents at FIG. 33 may be analogous to the operations for entering reagents (Block 314 of FIG. 3).

Figure 34:
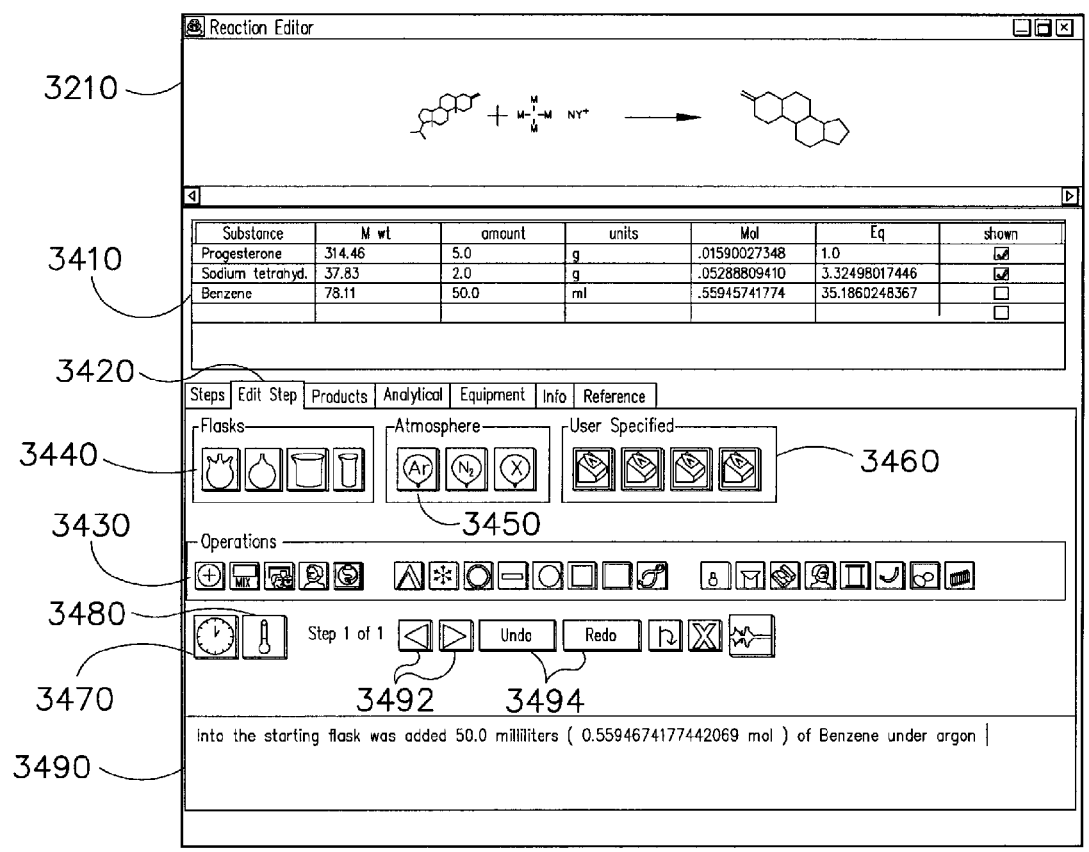

Referring now to FIG. 34, the entire reaction has been entered in window 3210, and a list of the reagents also is included in window 3410. In some embodiments, once the reagents are entered at window 3410, equivalent amounts may be back-calculated, so that the proper amounts of each reagent may be obtained based on, for example, a desired amount of one reagent that is to be used or generated. The edit step tab 3420 may be selected to allow the step to be generated. The operations to generate a step may be analogous to the operations of Block 330 of FIG. 3.

Referring again to FIG. 34, the edit step tab 3420 uses a plurality of icons in order to allow simplified generation of a step. For example, a plurality of operation icons 3430, flask icons 3440, atmosphere icons 3450, and user-specified icons 3460 may be provided. In addition, a time icon 3470 and a temperature icon 3480 also may be provided. The operation icons 3430 of FIG. 34 may correspond, from left to right, to the following operations: added, mixed, dissolved, degassed, evacuated, heated, cooled, refluxed, stirred, shaken, extracted, washed, distilled, dried, filtered, recrystallized, concentrated, chromatographed, titrated, triturated, and rotovap. Other icons for other standard operations also may be provided. It also will be understood that different illustrations may be provided from those shown, to symbolize the various operations.

Still referring to FIG. 34, the flask icons 3440 may allow selection of various flasks, and the atmosphere icons 3450 may allow selection of argon, nitrogen, and/or other atmospheres. The user-specified icons 3460 can allow a user to specify other operations that are not provided in the standard operations 3430, and can add a new icon as desired. The time icon 3470 can be used to specify a time and the temperature icon 3480 can be used to specify a temperature. Thus, the icons 3440-3480 can be selected in a desired sequence, in order to generate the step that is shown in window 3490. Thus, procedures can be built using the step editor. A user can move forward and backward using the forward and backward buttons 3492 and can undo or redo a step using the undo and redo buttons 3494. Accordingly, the language for the step may be generated from the icons, to allow simplified creation of a step.

Figure 35:
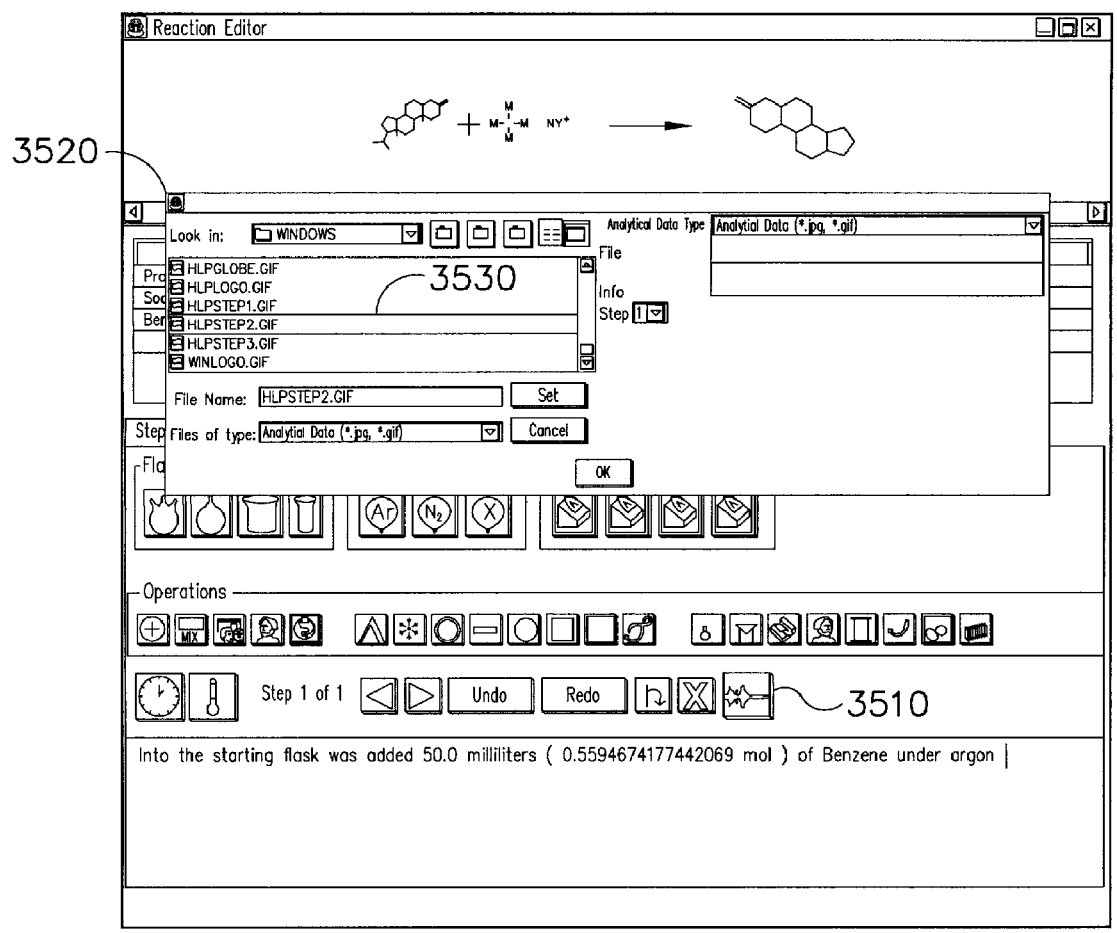

Referring now to FIG. 35, an analytical data icon 3510 also may be provided that allows attaching analytical data from external sources to that step. For example, as shown in FIG. 35, a window 3520 is created by searching an external network to obtain additional information about the step. The desired information may then be selected at 3530, and then stored in context with that step. Accordingly, external data capture may be provided.

Accordingly, embodiments of the invention that were described in connection with FIGS. 32-36 provide a user interface including a plurality of icons that correspond to at least one of operations, flasks, atmospheres, time or temperature that may be used to generate a procedure that is used to synthesize a target chemical by reacting a corresponding reagent chemical in the corresponding equipment according to the procedure. These embodiments also allow sequentially accepting user entry of selected ones of icons from the user interface to build the procedure.

Figure 36:
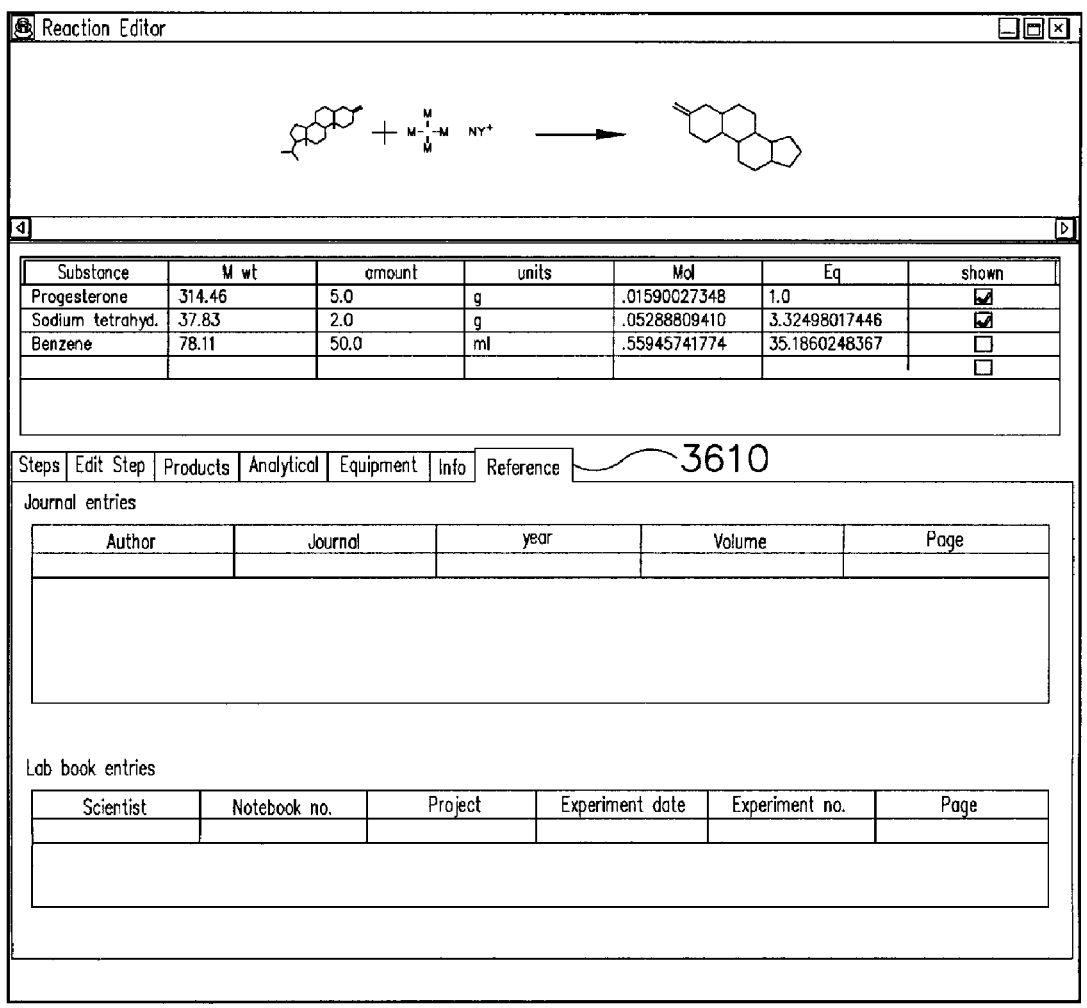

Referring now to FIG. 36, the reference tab 3610 also may be selected to add other data under various categories, such as journal entries and lab entries. Accordingly, an icon-based user interface may be used to enter a procedure.

As was described in FIGS. 17, 18, and 24-27, many embodiments of user displays may be provided according to the present invention, to allow user queries to be performed. Other embodiments of the present invention that will now be described, allow user queries to be formulated by presenting specific criteria choices that are based on the criteria that may be selected by a user. A context-sensitive Boolean query option generator may thereby be provided. In particular, these embodiments of the invention can allow reactions to be searched using an integrated search tool that allows for substructure/exact structure searching, combined with Boolean search options that can be set by the user.

Figure 37:
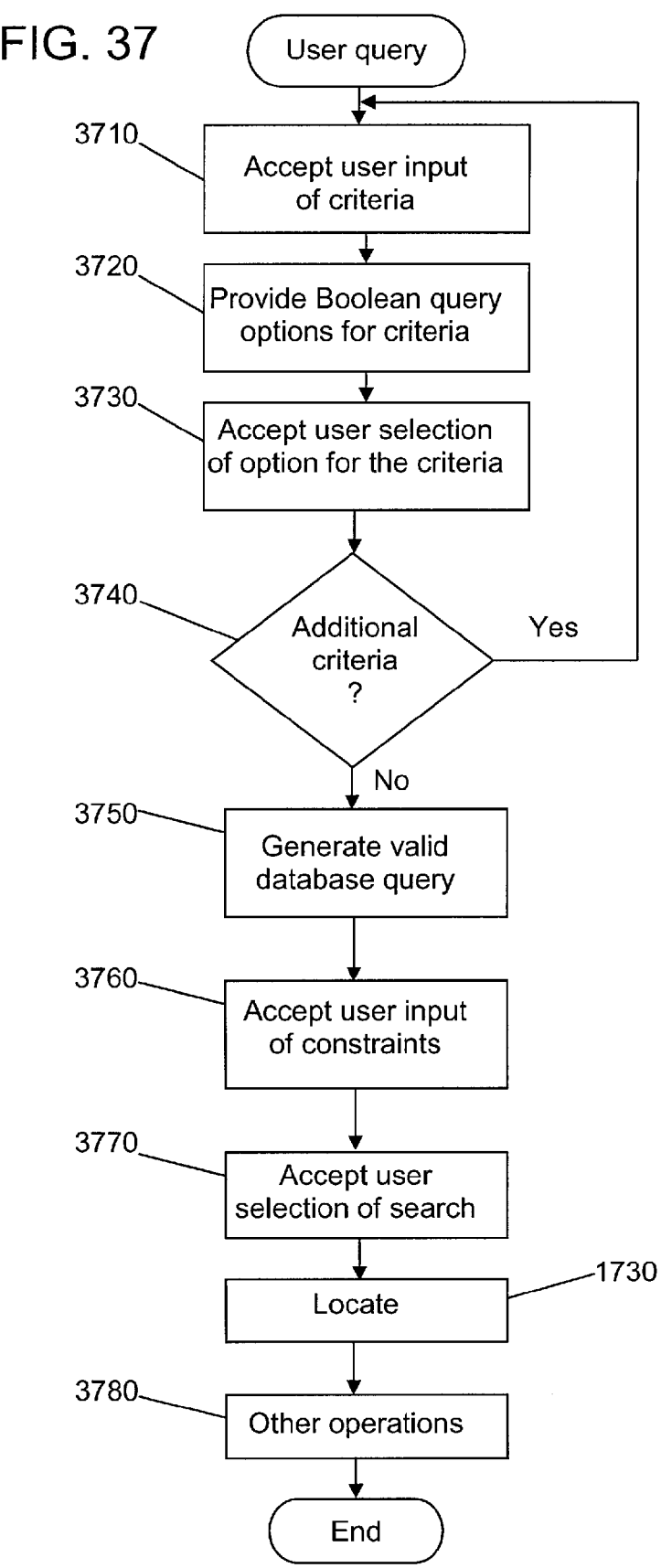
FIG. 37 is a flowchart of operations that may be used to perform a user query according to embodiments of the present invention.

Referring now to FIG. 37, operations for performing user queries according to these embodiments of the invention, now will be described. At Block 3710, a user input of a criteria to be searched is accepted. For example, FIG. 38 illustrates a user display screen which includes a criteria selection box 3810 that allows the user to select a criteria on which the user wishes to search.

Referring back to FIG. 37, at Block 3720, in response to the user input of the criteria, Boolean query options for that criteria are presented. For example, the search type selection box 3820 of FIG. 38 can allow a user to select the type of data the user wishes to search, and the Boolean operators 3830 of FIG. 38 allow a user to build a query using only the available operations that can be allowed. Thus, Boolean operator buttons 3830 may be selectively displayed based on the Boolean operators that are valid for the criteria that was selected in the criteria selection box 3810 and/or 3820.

Figure 38:
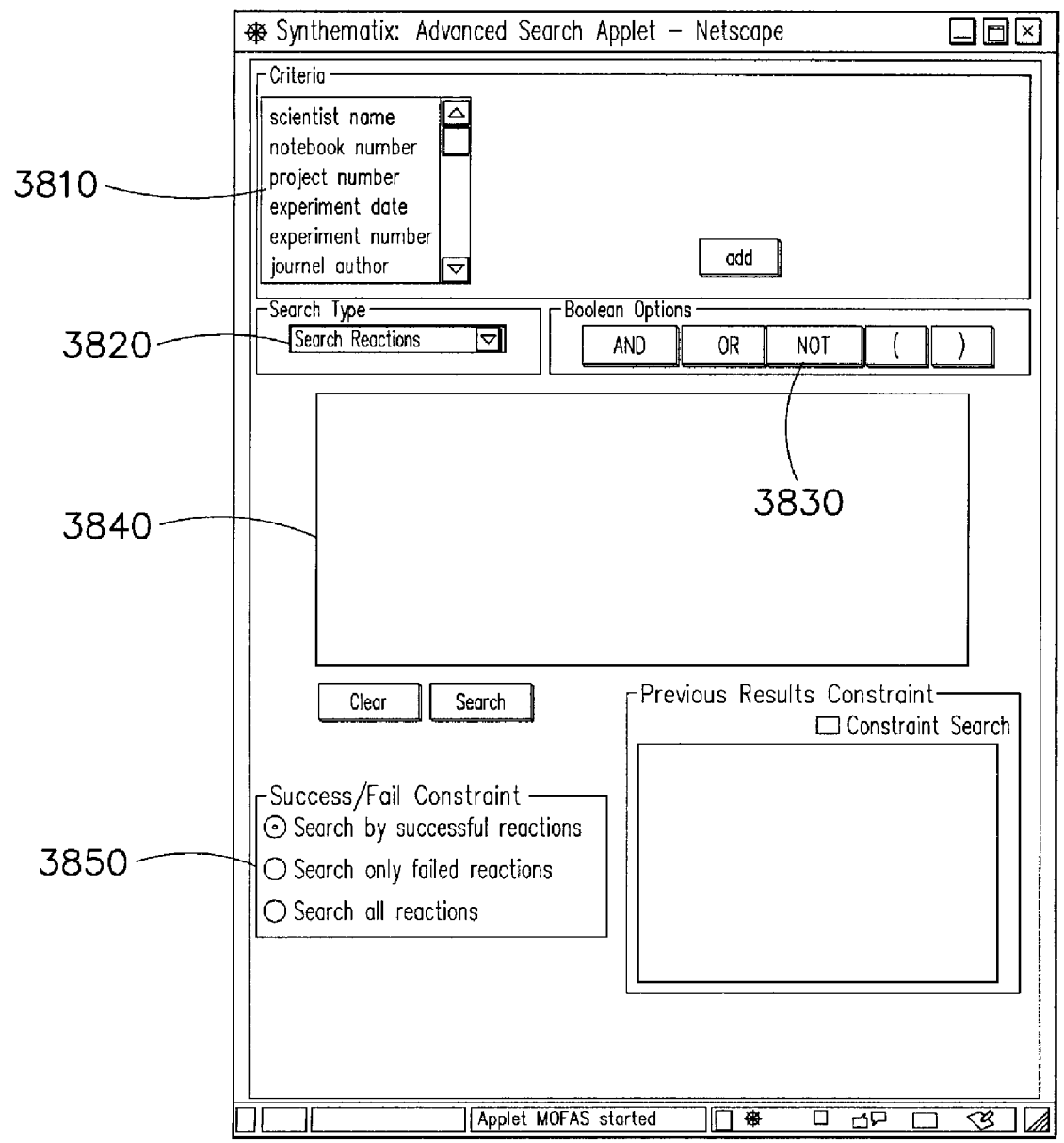
FIGS. 38-40 illustrate user displays that may be used to perform a query according to embodiments of the present invention.

Referring back to FIG. 37, at Block 3730, a user selection of the option for the criteria is accepted, for example by allowing the user to select one of the Boolean option buttons 3830 of FIG. 38. If additional criteria are desired by the user at Block 3740, then the operations of Blocks 3710, 3720 and 3730 can be repeatedly performed, to generate a complete user query, wherein only valid criteria are used, and wherein only valid Boolean options are used, so that a valid database query is generated at Block 3750. The actual database query may be displayed in the query field 3840. The query field 3840 also may permit a typed query to be entered.

Referring again to FIG. 37, at Block 3760, in some embodiments, user input of constraints is accepted, for example using the constraint selections 3850. As shown at 3850 of FIG. 38, searches may be performed by successful reactions, failed reactions or all reactions. Other constraints also may be used.

Referring again to FIG. 37, a locate operation 1730 that already was described in connection with FIG. 17 then may be performed to perform the query of the database, in response to acceptance of the user selection of the search (Block 3770), for example by selecting the search button of FIG. 38. Finally, at Block 3780, in response to the query being run, other operations 3780 may be performed, such as the operations of Blocks 1730-1750 of FIG. 17. In other embodiments, a reaction triage of FIGS. 26 and 27 also may be performed. Other operations also may be performed, as were described above.

Figure 39:
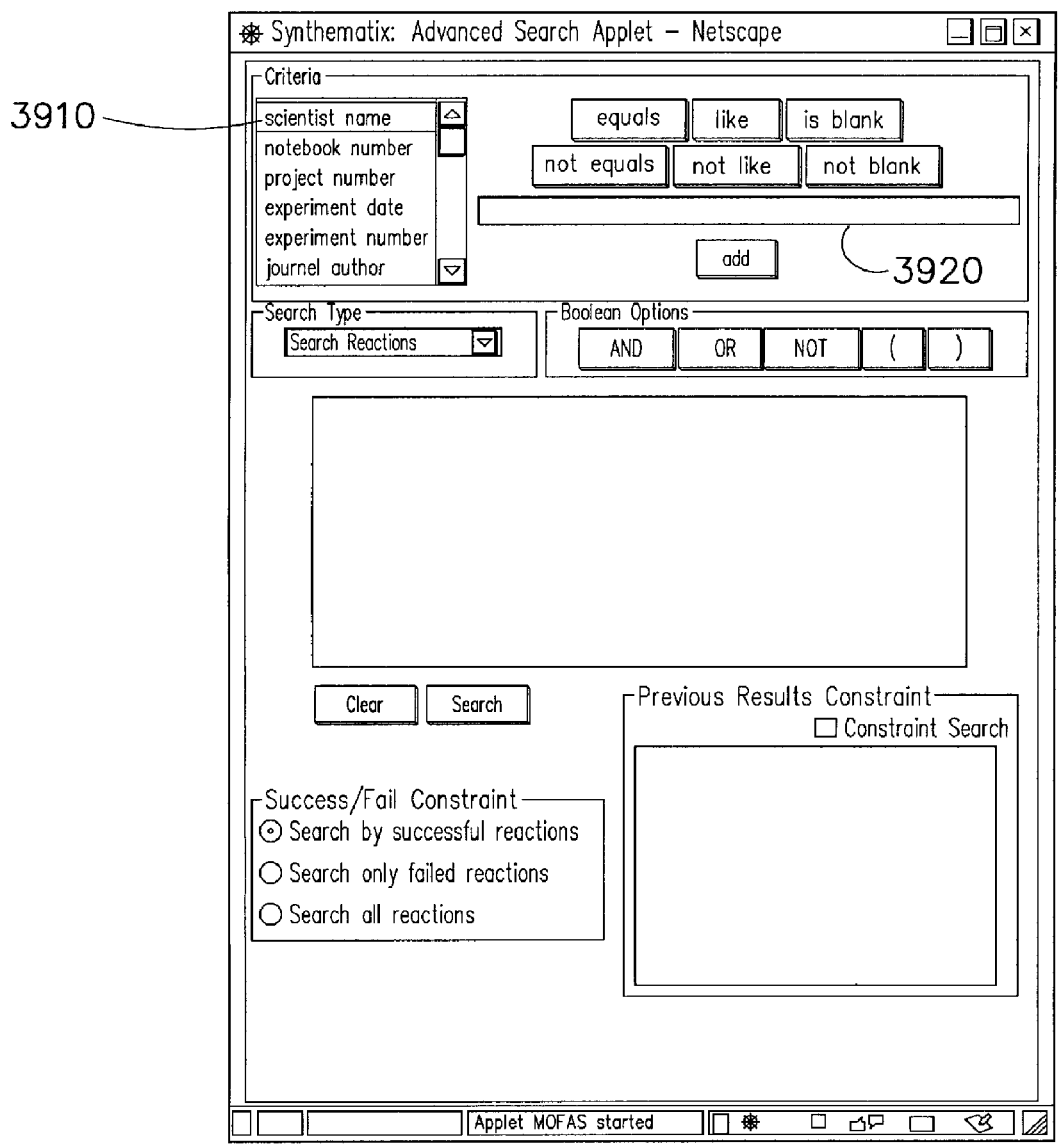
Figure 40:
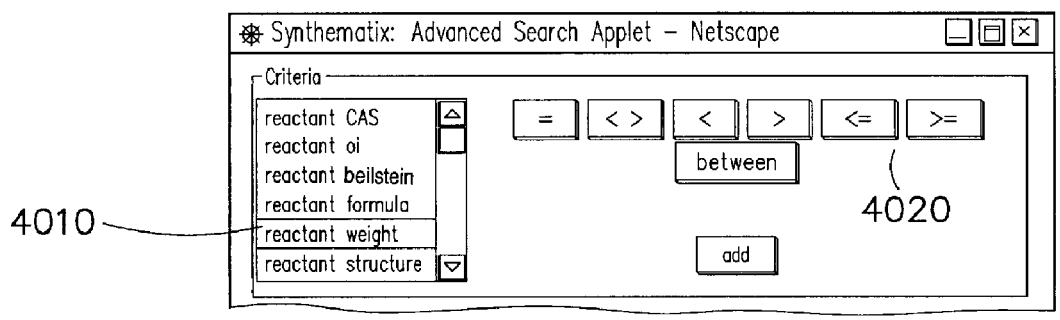

FIGS. 39 and 40 illustrate examples of providing Boolean query options for a specific criteria that was selected by a user (Block 3720 of FIG. 37) according to some embodiments of the present invention. In particular, in FIG. 39, the user has selected the scientist's name 3910 in the criteria selection box. In response, a selection of Boolean criteria buttons 3920 that is appropriate for performing Boolean searches on a scientist's name is displayed. In FIG. 40, the user has selected reactant weight 4010 in the criteria selection box. An array of buttons 4020 for permissible Boolean operations that may be used with reactant weight is displayed at 4020.

Accordingly, these embodiments of the invention can allow a user to select a valid choice of Boolean operators based on a criteria that is selected for a user. A complex search query may thereby be built, while increasing or maximizing the likelihood that a valid query is generated. Thus, these embodiments accept a user criterion for identifying a target chemical and display Boolean query options to the user that apply to the user criterion that was accepted. The accepting of a user criterion and the displaying of Boolean query options are repeated, to build a query of the database. A user query of the database thereby may be built and run.

Other embodiments of the present invention, referred to herein as a "reaction relay", display a target chemical as a hub (node), reagent chemicals that are used to synthesize the target chemical as spokes (branches) leading to the hub and additional chemicals in which the target chemical is a reagent chemical as spokes emerging from the hub. This display can provide one degree of separation from the target chemical. Multiple degrees of separation also may be provided by further displaying additional reagent chemicals that are used to synthesize the reagent chemicals, as spokes leading to the reagent chemicals, and by further displaying chemicals in which the additional chemicals are reagent chemicals, as spokes emerging from the additional chemicals.

Figure 42:
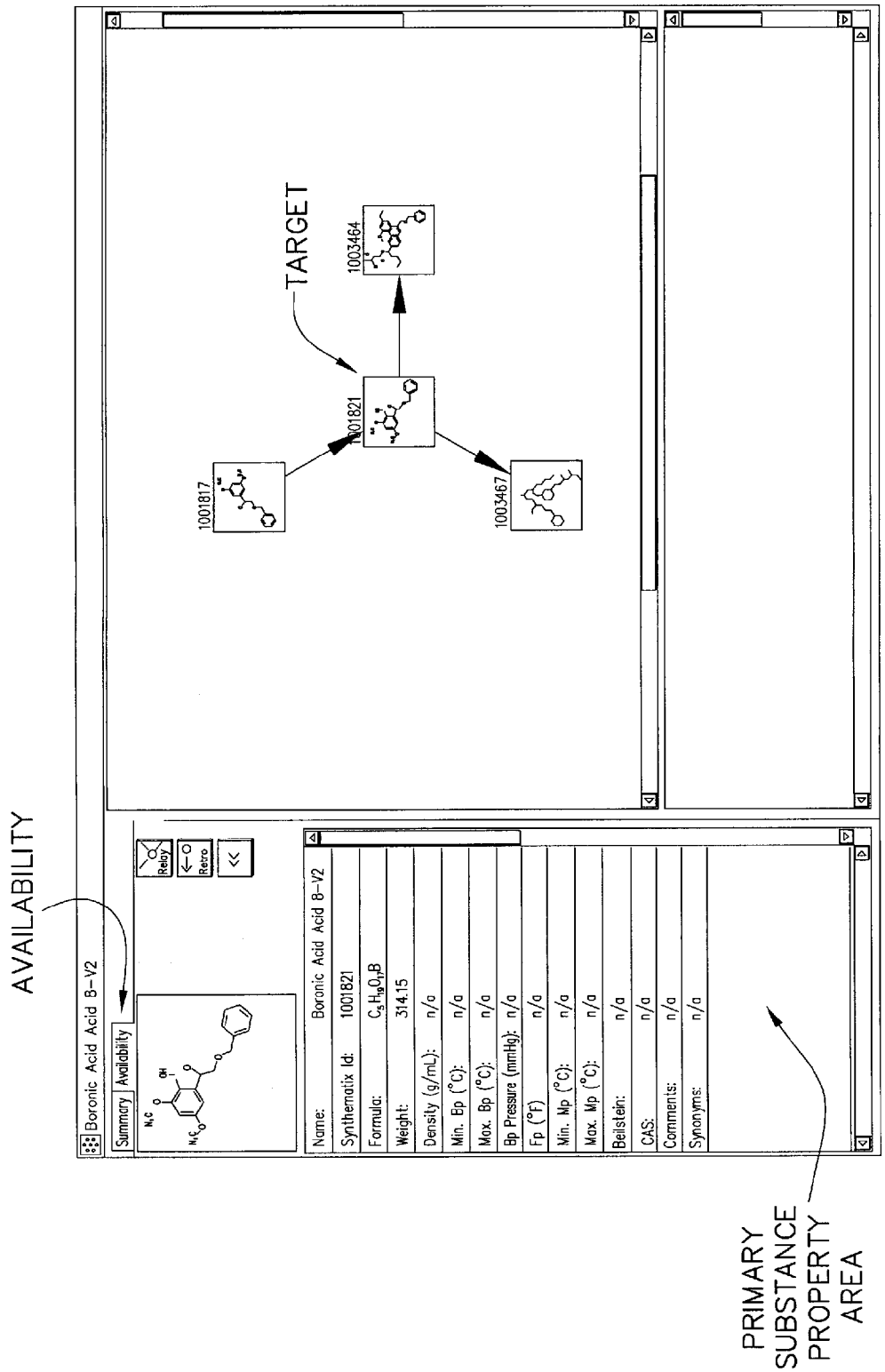

FIG. 42 shows an example of a graphical user interface for a reaction relay. This graphical user interface can allow users to obtain a unique graphical view of a database query on what a particular target chemical can possibly make and what other particular reagents can make the target chemical. The display may be filtered using primary reactants as a criterion, but other filters such as source, author, yield, safety, cost, scientist, project, substructure and/or other criteria can be used to reduce the explosion of data that may result. Accordingly, these embodiments of the present invention can allow a chemist to see a colleague's data in a hub and spoke graphical user interface. The data can then be modified or templated as was already described.

FIG. 42 illustrates a one degree of separation graphical user interface that displays a target chemical as a hub, reagent chemicals that are used to synthesize the target chemical as spoke's leading to the hub (indicated by an arrow leading to the hub), and additional chemicals in which the target chemical is a reagent chemical as spokes emerging from the hub (indicated by arrows emerging from the hub). In some embodiments, the display can be caused to stop with one degree of separation from the target chemical as shown in FIG. 42. The user can then navigate and reinitiate the query by double-clicking any chemical. By clicking once on a substance, the target is loaded into the primary substance property area, shown as the left panel of FIG. 42. From this area, a user can select a reaction relay and/or retro-synthetic views as was already described.

Figure 43:
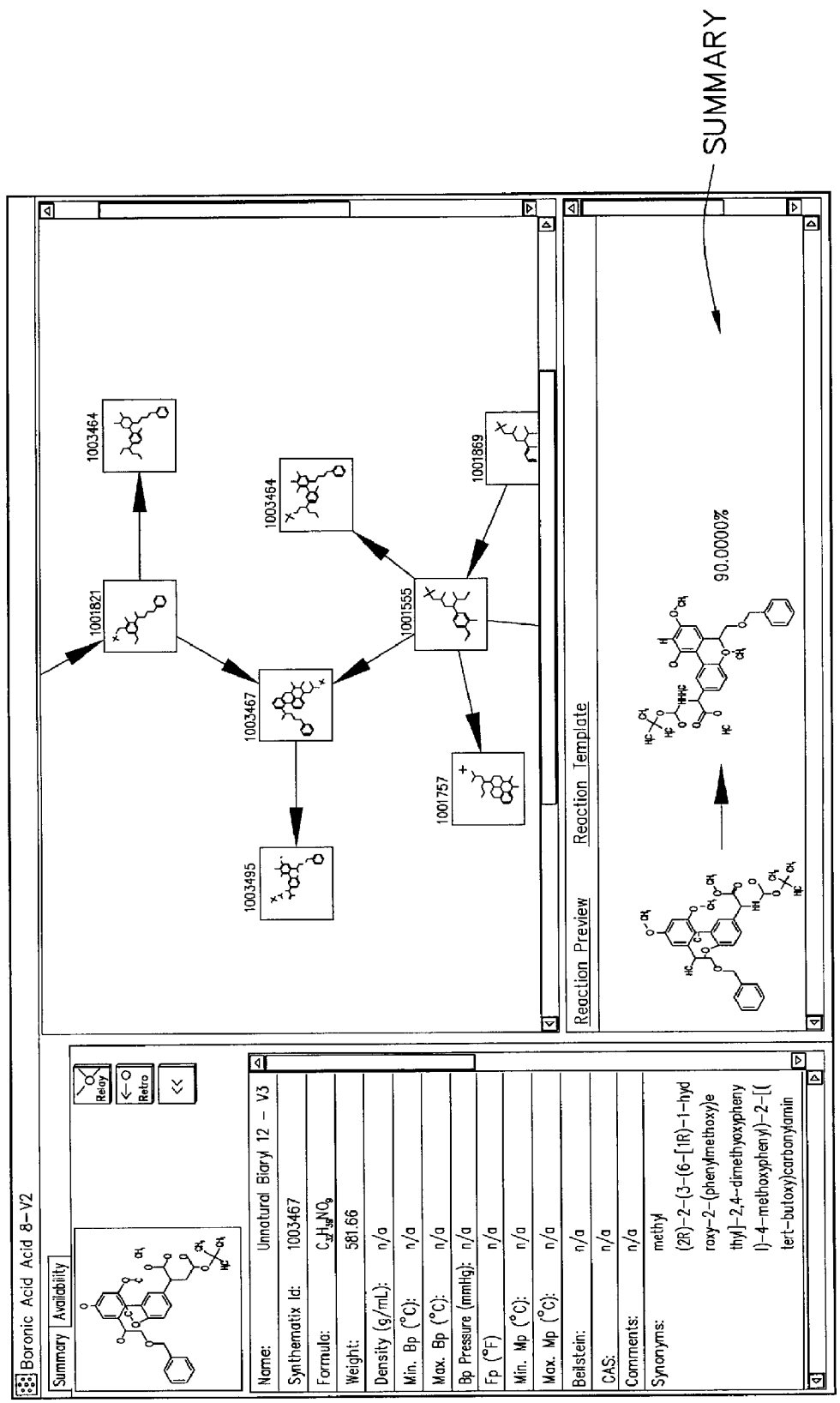

FIG. 43 illustrates a reaction relay interface that has more than one degree of separation. In particular, as shown in FIG. 43, a further display is provided of additional reagent chemicals that are used to synthesize the reagent chemicals, as spokes leading to the reagent chemicals, and a further display of chemicals in which the additional chemicals are reagent chemicals, as spokes emerging from the additional chemicals. FIG. 43 also illustrates a reaction summary in the bottom right panel. This may be displayed by the user clicking on an arrow in the reaction relay of the upper right panel. The arrows have numbers that represent how many possible ways or procedures that a particular reaction has been attempted. From this panel, users can then invoke templates to modify and/or model any reaction that is contained within the database.

Additional description of the reaction relay user interface of FIGS. 42 and 43 will now be provided. As was noted above, the user interface may be divided into three main areas. The largest section, located at the upper right hand panel of FIGS. 42 and 43, illustrates the hub/spoke arrangement as a user, via a series of selections or clicks, builds it. The panel located at the left side of FIGS. 42 and 43 shows information about a substance that matches the property information stored in the database. The panel located at the bottom right of the user interface of FIGS. 42 and 43 provides basic information about any of the associated reactions and allows the user to jump to the reactions. All of the panels may be adjustable by clicking on the divider lines and dragging them to make the frames bigger or smaller or to change their locations as desired.

Once launched, the reaction relay runs dynamically against the information stored in the database and graphs out all of the possibilities of what a target chemical makes and what can make it, using the hub and spoke arrangement. Clicking each block once can provide the substance property information in the left hand panel. Double-clicking a block can run the search out again and expand the display to show all of the paths to and from the chemical by one degree of separation. By double-clicking on a block, the block can center itself so that all the items that are branched off it are shown in the panel. If the display is too big for the panel, the navigation bars at the bottom and side of the panel can be used to view all of the results. Once a desired path has been created, the user can then navigate among the hubs and spokes until familiar structures are seen. If the user wishes to collapse any of the hubs and spokes to avoid confusion or because they do not contain data that is useful to the user, the user can double-click on the central hub, and the spokes not associated with the direct path will disappear. All of the blocks also are movable, so if the user wishes to move one item or an entire tree using the center block, the desired block may be clicked on and dragged to a new location. Thus, a path can be sorted without collapsing any hubs and spokes.

If the information in the left hand panel is not completely visible, the scrolling bar at the right hand side of the panel can be used to view all of the information. The availability and primary substance properties in the left hand panel can change to match the most recently selected chemical as a user navigates around the reaction relay.

The spokes (arrows) leading to and from each block also can connect the user to useful information. Each arrowhead contains a number. This number indicates how many reactions are associated with that reaction path. Double-clicking each arrowhead can provide reaction summary information in the bottom panel. The reaction summary can provide a diagram of the reaction scheme, the yield of each product, a list of other reagents used in the reaction that are not depicted in the reaction scheme, and the journal and/or notebook reference. If there is more than one reaction associated with the selected target chemical, the previous and next links may be available to allow user navigation through the reactions to determine which one is most appropriate for the user's research. Once a reaction is located, a view details link can be selected to jump to the run sheets as was already described.

Figure 44:
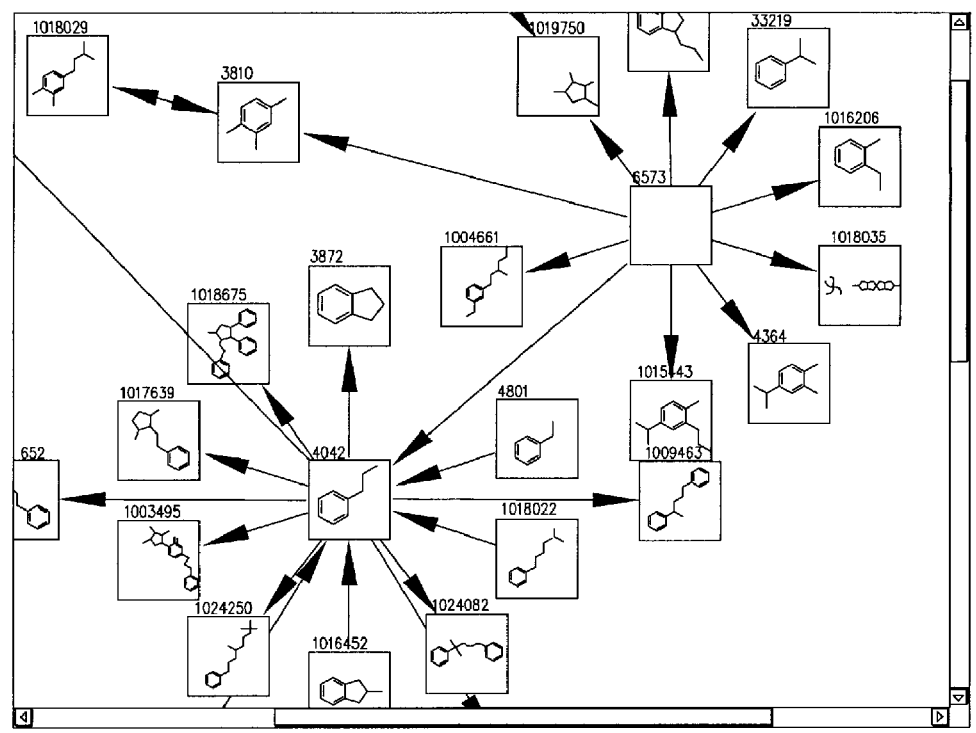
Figure 45:
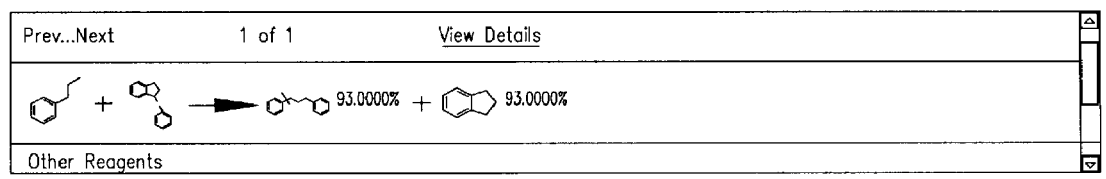

FIG. 44 provides another example of a reaction relay graphical user interface. FIG. 45 provides another example of a reaction summary panel for this interface.

In the drawings and specification, there have been disclosed embodiments of the invention and, although specific terms are employed, they are used in a generic and descriptive sense only and not for purposes of limitation, the scope of the invention being set forth in the following claims.

What is claimed is:

1. A computerized method of determining parameters for chemical reactions, comprising:
   accepting user input identifying a target chemical;
   searching a computer-readable database to identify chemical reactions in which the identified target chemical is a product;
   generating a visual representation of the identified chemical reactions, the visual representation including a flowchart having a plurality of nodes and a plurality of branches, the plurality of nodes including a first node representing the target chemical and a plurality of second nodes representing first reagent chemicals used to synthesize the target chemical and second reagent chemicals used to synthesize the first reagent chemicals, the plurality of branches including a plurality of first branches connecting the first node and the plurality of second nodes, each of the first branches representing a reaction path in which the target chemical is synthesized from the corresponding first reagent chemical, and a plurality of second branches connecting one or more of the second nodes to one or more other of the second nodes, each of the second branches representing a reaction path in which one of the first reagent chemicals is synthesized from a corresponding one of the second reagent chemicals; and
   displaying the visual representation.

2. The method of claim 1, wherein:
   searching the database to identify chemical reactions in which the identified target chemical is a product further includes identifying procedures used to synthesize the target chemical.

3. The method of claim 1, wherein:
   searching the database to identify chemical reactions in which the identified target chemical is a product further includes identifying the first reagent chemicals used to synthesize the target chemical.

4. The method of claim 3, further comprising:
   searching the database to identify chemical reactions in which the first reagent chemicals are products.

5. The method of claim 4, wherein:
   searching the database to identify chemical reactions in which the first reagent chemicals are products includes identifying procedures used to synthesize the first reagent chemicals.

6. The method of claim 4, wherein:
   searching the database to identify chemical reactions in which the first reagent chemicals are products further includes identifying the second reagent chemicals used to synthesize the first reagent chemicals.

7. The method of claim 1, wherein:
   the plurality of nodes further includes a plurality of third nodes representing third reagent chemicals used to synthesize the second reagent chemicals; and
   the plurality of branches includes a plurality of third branches connecting one or more of the second nodes to one or more of the plurality of third nodes, each of the second branches representing a reaction path in which one of the second reagent chemicals is synthesized from a corresponding one of the third reagent chemicals.

8. The method of claim 7, further comprising:
   searching the database to identify chemical reactions in which the second reagent chemicals are products.

9. The method of claim 8, wherein:
   searching the database to identify chemical reactions in which the second reagent chemicals are products further includes identifying procedures used to synthesize the second reagent chemicals.

10. The method of claim 8, wherein:
    searching the database to identify chemical reactions in which the second reagent chemicals are products further includes identifying the third reagent chemicals used to synthesize the second reagent chemicals.

11. The method of claim 7, further comprising:
    accepting user input selecting one or more of the second and third nodes in the visual representation; and user input
    to navigate forward or backward in the flowchart.

12. A computer-readable storage medium encoded with instructions for determining parameters for chemical reactions by causing a data processing apparatus to perform operations including:
    accepting user input identifying a target chemical;
    searching a database to identify chemical reactions in which the identified target chemical is a product;
    generating a visual representation of the identified chemical reactions, the visual representation including a flowchart having a plurality of nodes and a plurality of branches, the plurality of nodes including a first node representing the target chemical and a plurality of second nodes representing first reagent chemicals used to synthesize the target chemical and second reagent chemicals used to synthesize the first reagent chemicals, the plurality of branches including a plurality of first branches connecting the first node and the plurality of second nodes, each of the first branches representing a reaction path in which the target chemical is synthesized from the corresponding first reagent chemical, and a plurality of second branches connecting one or more of the second nodes to one or more other of the second nodes, each of the second branches representing a reaction path in which one of the first reagent chemicals is synthesized from a corresponding one of the second reagent chemicals; and
    displaying the visual representation.

13. The computer readable storage medium of claim 12, wherein:
    the instructions operable to cause the data processing apparatus to search the database to identify chemical reactions in which the identified target chemical is a product further include instructions operable to cause the data processing apparatus to identify procedures used to synthesize the target chemical.

14. The computer readable storage medium of claim 12, wherein:
the instructions operable to cause the data processing apparatus to search the database to identify chemical reactions in which the identified target chemical is a product further include instructions operable to cause the data processing apparatus to identify the first reagent chemicals used to synthesize the target chemical.

15. The computer readable storage medium of claim 14, further comprising:
instructions operable to cause the data processing apparatus to search the database to identify chemical reactions in which the first reagent chemicals are products.

16. The computer readable storage medium of claim 15, wherein:
the instructions operable to cause the data processing apparatus to search the database to identify chemical reactions in which the first reagent chemicals are products include instructions operable to cause the data processing apparatus to identify procedures used to synthesize the first reagent chemicals.

17. The computer readable storage medium of claim 15, wherein:
the instructions operable to cause the data processing apparatus to search the database to identify chemical reactions in which the first reagent chemicals are products further include instructions operable to cause the data processing apparatus to identify the second reagent chemicals used to synthesize the first reagent chemicals.

18. The computer readable storage medium of claim 12, wherein:
the plurality of nodes further includes a plurality of third nodes representing third reagent chemicals used to synthesize the second reagent chemicals; and
the plurality of branches includes a plurality of third branches connecting one or more of the second nodes to one or more of the plurality of third nodes, each of the second branches representing a reaction path in which one of the second reagent chemicals is synthesized from a corresponding one of the third reagent chemicals.

19. The computer readable storage medium of claim 18, further comprising:
instructions operable to cause the data processing apparatus to search the database to identify chemical reactions in which the second reagent chemicals are products.

20. The computer readable storage medium of claim 19, wherein:
the instructions operable to cause the data processing apparatus to search the database to identify chemical reactions in which the second reagent chemicals are products further include instructions operable to cause the data processing apparatus to identify procedures used to synthesize the second reagent chemicals.

21. The computer readable storage medium of claim 19, wherein:
the instructions operable to cause the data processing apparatus to search the database to identify chemical reactions in which the second reagent chemicals are products further include instructions operable to cause the data processing apparatus to identify the third reagent chemicals used to synthesize the second reagent chemicals.

22. The computer readable storage medium of claim 18, further comprising instructions operable to cause the data processing apparatus to perform operations including:
accepting user input selecting one or more of the second and third nodes in the visual representation; and user input
to navigate forward or backward in the flowchart.

23. A programmable data processing apparatus, configured to determine parameters for chemical reactions, the apparatus comprising:
a processor; and a
memory, on which are stored a database and instructions operable to cause the data processing apparatus to:
accept a user input identifying a target chemical;
search the database to identify chemical reactions in which the identified target chemical is a product;
generate a visual representation of the identified chemical reactions, the visual representation including a flowchart having a plurality of nodes and a plurality of branches, the plurality of nodes including a first node representing the target chemical and a plurality of second nodes representing first reagent chemicals used to synthesize the target chemical and second reagent chemicals used to synthesize the first reagent chemicals, the plurality of branches including a plurality of first branches connecting the first node and the plurality of second nodes, each of the first branches representing a reaction path in which the target chemical is synthesized from the corresponding first reagent chemical, and a plurality of second branches connecting one or more of the second nodes to one or more other of the second nodes, each of the second branches representing a reaction path in which one of the first reagent chemicals is synthesized from a corresponding one of the second reagent chemicals; and
display the visual representation.

24. The data processing apparatus of claim 23, wherein:
the instructions operable to cause the apparatus to search the database to identify chemical reactions in which the identified target chemical is a product further include instructions operable to cause the apparatus to identify procedures used to synthesize the target chemical.

25. The data processing apparatus of claim 23, wherein:
the instructions operable to cause the apparatus to search the database to identify chemical reactions in which the identified target chemical is a product further include instructions operable to cause the apparatus to identify the first reagent chemicals used to synthesize the target chemical.

26. The data processing apparatus of claim 25, further comprising:
instructions operable to cause the apparatus to search the database to identify chemical reactions in which the first reagent chemicals are products.

27. The data processing apparatus of claim 26, wherein:
the instructions operable to cause the apparatus to search the database to identify chemical reactions in which the first reagent chemicals are products include instructions operable to cause the apparatus to identify procedures used to synthesize the first reagent chemicals.

28. The data processing apparatus of claim 26, wherein:
the instructions operable to cause the apparatus to search the database to identify chemical reactions in which the first reagent chemicals are products further include instructions operable to cause the apparatus to identify the second reagent chemicals used to synthesize the first reagent chemicals.

29. The data processing apparatus of claim 23, wherein:
the plurality of nodes further includes a plurality of third nodes representing third reagent chemicals used to synthesize the second reagent chemicals; and
the plurality of branches includes a plurality of third branches connecting one or more of the second nodes to one or more of the plurality of third nodes, each of the second branches representing a reaction path in which one of the second reagent chemicals is synthesized from a corresponding one of the third reagent chemicals.

30. The data processing apparatus of claim 29, further comprising:
instructions operable to cause the apparatus to search the database to identify chemical reactions in which the second reagent chemicals are products.

31. The data processing apparatus of claim 30, wherein:
the instructions operable to cause the apparatus to search the database to identify chemical reactions in which the second reagent chemicals are products further include instructions operable to cause the apparatus to identify procedures used to synthesize the second reagent chemicals.

32. The data processing apparatus of claim 30, wherein:
the instructions operable to cause the apparatus to search the database to identify chemical reactions in which the second reagent chemicals are products further include instructions operable to cause the apparatus to identify the third reagent chemicals used to synthesize the second reagent chemicals.

33. The data processing apparatus of claim 29, further comprising instructions operable to cause the apparatus to perform operations including:
accepting user input selecting one or more of the second and third nodes in the visual representation; and user input to navigate forward or backward in the flowchart.

* * * * *